(12) United States Patent
Guindon

(10) Patent No.: US 8,361,988 B2
(45) Date of Patent: Jan. 29, 2013

(54) NUCLEOSIDE AND NUCLEOTIDE ANALOGUES WITH QUATERNARY CARBON CENTERS AND METHODS OF USE

(75) Inventor: Yvan Guindon, Montreal (CA)

(73) Assignee: Institut de Recherches Cliniques de Montreal, Montreal, Quebec (CA)

( * ) Notice: Subject to any disclaimer, the term of this patent is extended or adjusted under 35 U.S.C. 154(b) by 558 days.

(21) Appl. No.: 12/523,193

(22) PCT Filed: Jan. 17, 2008

(86) PCT No.: PCT/IB2008/000697
§ 371 (c)(1),
(2), (4) Date: Dec. 23, 2009

(87) PCT Pub. No.: WO2008/087558
PCT Pub. Date: Jul. 24, 2008

(65) Prior Publication Data
US 2010/0093737 A1    Apr. 15, 2010

Related U.S. Application Data

(60) Provisional application No. 60/881,043, filed on Jan. 17, 2007.

(51) Int. Cl.
| | |
|---|---|
| *C07H 19/056* | (2006.01) |
| *C07H 19/073* | (2006.01) |
| *C07H 19/173* | (2006.01) |
| *A61K 31/7012* | (2006.01) |
| *A61K 31/7056* | (2006.01) |
| *A61K 31/706* | (2006.01) |
| *A61K 31/7064* | (2006.01) |
| *A61K 31/7068* | (2006.01) |
| *A61K 31/7072* | (2006.01) |
| *A61K 31/7076* | (2006.01) |
| *A61K 31/708* | (2006.01) |

(52) U.S. Cl. ............... 514/45; 514/46; 514/47; 514/48; 514/49; 514/50; 514/51; 514/52; 536/26.7; 536/26.8; 536/27.3; 536/28.51; 536/28.52; 536/28.53; 536/28.54; 536/28.55

(58) Field of Classification Search .................. None
See application file for complete search history.

(56) References Cited

U.S. PATENT DOCUMENTS
| | | | |
|---|---|---|---|
| 6,914,054 B2 * | 7/2005 | Sommadossi et al. | .......... 514/49 |
| 7,056,704 B2 | 6/2006 | Tuschl et al. | |
| 2011/0092451 A1 * | 4/2011 | Guindon | .................. 514/46 |

FOREIGN PATENT DOCUMENTS
WO        02/32920 A2    4/2002

OTHER PUBLICATIONS

The Merck Manual of Diagnosis and Therapy, published 1999 by Merck Research Laboratories, pp. 397, 398, 948, 949, 973-995, 1085-1088, 1276-1283, 1916, and 1979-1981.*

Zhong et al., "Photochemistry on Soluble Polymer Supports: Synthesis of Nucleosides" Organic Letters, (2002) vol. 4, No. 25, pp. 4415-4417.*

Hamilton et al., "A Species of Small Antisense RNA in Post-transcriptional Gene Silencing in Plants", Science, 1999, 286:950-952.

Elbashir et al., "Duplexes of 21-nucleotide RNAs mediate RNA interference in cultured mammalian cells", Nature, May 24, 2001, 411:494-498.

Berge et al., "Pharmaceutical Salts", J. Pharm. Sci., Jan. 1977, 66(1):1-19.

Stella V., "Pro-drugs: An Overview and Definition", in Pro-drugs as Novel Drug Delivery Systems, eds. T Higuchi, V Stella, ACS Symposium Series, American Chemical Society, Washington, DC, 1975, pp. 1-115.

Cardinal-David et al., "Synthesis of Tertiary and Quaternary Stereogenic Centers: A Diastereoselective Tandem Reaction Sequence Combining Mukaiyama and Free Radical-Based Allylation", J. Org. Chem., 2005, 70(3):776-784.

Mosmann, "Rapid Colorimetric Assay for Cellular Growth and Survival: Application to Proliferation and Cytotoxicity Assays", J. Immunol. Methods, Dec. 16, 1983, 65(1-2):55-63.

Munch-Petersen et al., "Functional Expression of a Multisubstrate Deoxyribonucleoside Kinase from *Drosophila melanogaster* and Its C-terminal Deletion Mutants", J. Biol. Chem., Mar. 3, 2000, 275(9):6673-6679.

Schelling et al., "A Spectrophotometric Assay for Quantitative Determination of kcat of Herpes Simplex Virus Type 1 Thymidine Kinase Substrates", Anal. Biochem., 2001, 295:82-87.

Pollex et al., "Ester Dienolate [2,3]-Wittig Rearrangement in Natural Product Synthesis: Diastereoselective Total Synthesis of the Triester of Viridiofungin A, A2, and A4", J. Org. Chem., 2005, 70:5579-5591.

Ley et al., "Microencapsulation of Osmium Tetroxide in Polyurea", Org. Lett., 2003, 5(2):185-187.

Zhong et al., "Efficient and Facile Glycol Cleavage Oxidation Using Improved Silica Gel-Supported Sodium Metaperiodate", J. Org. Chem., 1997, 62:2622-2624.

Whittingham et al., "Syntheses Relevant to Vitamin B12 Biosynthesis: the Malate Route to (−)-Ring-B Imide and Synthesis of the 2,7,20-Trimethylisobacteriochlorin", J. Chem. Soc., Chem. Commun., 1989, 1116-1119.

(Continued)

*Primary Examiner* — Eric S Olson
(74) *Attorney, Agent, or Firm* — McDonnell Boehnen Hulbert & Berghoff LLP

(57) ABSTRACT

The present invention comprises compounds useful as antiviral or antitumor agents. The compounds comprise nucleotide analogues that comprise tetrahydrofuranyl or tetrahydrothienyl moeities with quaternary centers at the 3' position. The nucleotide analogues can be used to inhibit cancer or viruses. Accordingly, the compounds of the present invention are useful for treating, preventing, and/or inhibiting diseases or conditions associated with cancers and viruses. Thus, the present invention also comprising pharmaceutical formulations comprising the compounds and methods of using the compounds and formulations to inhibit viruses or tumors and treat, prevent, or inhibit the foregoing diseases.

17 Claims, No Drawings

OTHER PUBLICATIONS

Bioreversible Carriers in Drug Design, Theory and Application, ed. Edward B. Roche, American Pharmaceutical Association and Pergamon Press, 1987.

Remington's Pharmaceutical Sciences, 18th ed., Mack Publishing Company, Easton, PA, 1990.

* cited by examiner

NUCLEOSIDE AND NUCLEOTIDE ANALOGUES WITH QUATERNARY CARBON CENTERS AND METHODS OF USE

CROSS-REFERENCE TO RELATED APPLICATIONS

This application is a National Entry Application of PCT application no PCT/IB02008/000697 filed on Jan. 17, 2008 and published in English under PCT Article 21(2), which itself claims priority on U.S. provisional application Ser. No. 60/881,043, filed on Jan. 17, 2007. All documents above are incorporated herein in their entirety by reference.

FIELD OF THE INVENTION

This invention relates to the field of nucleoside and nucleotide analogues useful as antiviral and antitumor agents. In particular, the invention relates to compounds comprising tetrahydrofuranyl or tetrahydrothienyl moeities with quaternary carbon centers at the 3' position.

BACKGROUND OF THE INVENTION

Nucleosides and nucleotides are one of the most important cellular metabolites. Nucleosides are found primarily as the monomeric units comprising the major nucleic acids of the cell, RNA and DNA. However, they also are required for numerous other important functions within the cell. These functions include energy stores in phosphate transfer reactions (ATP); as coenzymes (for example, NAD+, NADP+, FAD and coenzyme A); mediators cellular processes (such as cyclic-AMP); allosteric effector on enzyme activity; and activated intermediates (S-adenosylmethionine).

Nucleoside analogues are chemically synthesized and used as therapeutics. Nucleoside analogues can be utilized to inhibit specific enzymatic activities, for example, as antitumor agents that interfere with the synthesis of DNA and thereby preferentially kill rapidly dividing cells such as tumor cells. Some commonly used nucleoside analogues in chemotherapy are 6-mercaptopurine, 5-fluorouracil, 5-iodo-2'-deoxyuridine and 6-thioguanine Synthesis of DNA is disrupted because the nucleotide analogues prevent correct Watson-Crick base-pairing.

Nucleoside analogues are also used as antiviral agents. Examples are abacavir, didanosine, emtricitabine, lamivudine, stavudine, tenofovir, zalcitabine, and zidovudine. For example, AZT (azidothymidine) and ddI (dideoxyinosine) are use to inhibit replication of HIV. Purine-containing nucleotide analogues are used to treat gout, for example, allopurinol that inhibits the activity of xanthine oxidase, an enzyme involved in de novo purine biosynthesis. Additionally, nucleoside analogues are used to suppress the immune system after organ transplantation and reduce transplant rejection.

Nucleotide analogues, in their phosphorylated form, are also included in small polymeric sequences used as antisense RNA, siRNA (small interfering RNA) or miRNA (micro RNA) to control the transcription and translation of genes related to cancer or viral infections.

Antisense mRNA is an mRNA transcript that is complementary to endogenous mRNA, that is, the noncoding strand complement to the coding strand. A strategy to block expression of a gene of interest is to introduce a transgene coding for antisense mRNA. Analogous molecules with modified backbones using nucleotide analogues have been designed which change various characteristics of antisense RNA, such as instability to degradative enzymes or ability to form stable double strands with the complementary sense RNA. Some alternative antisense molecules include phosphorothioate, morpholino, PNA (peptide nucleic acid), LNA (locked nucleic acid), and 2'-O alkyl oligos.

Small interfering RNA (siRNA), sometimes known as short interfering RNA or silencing RNA, are a class of 20-25 nucleotide-long RNA molecules that play a variety of roles. SiRNAs have a well defined structure that consist of a short, usually 21-nt, double-strand of RNA with 2-nt 3' overhangs on either end. Most notably, siRNA is involved in the RNA interference pathway (RNAi) where the siRNA interferes with the expression of specific genes. In addition, siRNAs also act in RNAi-related pathways, e.g. as an antiviral mechanism or in shaping the chromatin structure of a genome; the complexity of these pathways is only now being elucidated. SiRNAs were first discovered as part of post-transcriptional gene silencing (PTGS) in plants (see U.S. Pat. No. 7,056,704 and Hamilton and Baulcombe, Science, 1999, 286, 950-952). Synthetic siRNAs have also been shown to induce RNAi in mammalian cells (see Elbashir et al., Nature, 2001, 411, 494-498) with led to interest in harnessing RNAi for biomedical research and drug development.

Micro RNA (miRNA) are small ribonucleaic acid chains, about 22 nt long that are implicated in cell growth and apoptosis, embrionic development, neuronal plasticity and remodeling, and even insulin secretion. An overabundance of miRNA has been reported in cases of Fragile X Mental Retardation while some cancers have been reported to have down-regulated miRNA genes.

Antisense RNA, siRNA and miRNA are being experimentally applied as antisense therapy or to create knockout organisms to study gene function. For example, the suppression of protein synthesis by introducing antisense RNA, siRNA or miRNA into a cell may be useful to inhibit a number of infections or diseases in both plants and animals. A gene encoding the antisense RNA, siRNA or miRNA can be introduced fairly easily into organisms by using a plasmid vector or using a gene gun that shoots microscopic tungsten pellets coated with the gene into cells. Once the antisense RNA, siRNA or miRNA is introduced, it will specifically inhibit the synthesis of the target protein by binding to mRNA. Antisense RNA, siRNA or miRNA can be use in therapy, for example, for treating B-cell lymphomas and leukemias, treating HIV-1, cytomegalovirus, herpesvirus, asthma and cancers. Antisense RNA, siRNA or miRNA can also be used for commercial food production, for example, disease control and produce preservation. For example, siRNAs may be used as important tools for transcriptional modulating in silencing of mammalian genes by guiding DNA methylation.

Thus, an object of this invention is the identification of novel nucleoside analogues that can be used as antiviral or antitumor agents to inhibit diseases and conditions associated viruses and cancers.

SUMMARY OF THE INVENTION

The invention comprises compounds and pharmaceutical compositions of the compounds useful as antiviral or antitumor agents. The compounds of the invention comprise nucleoside analogues that comprise 2'-deoxy tetrahydrofuranyl or tetrahydrothienyl moeities with quaternary carbon centers at the C-3' position.

The first aspect of the invention provides compounds that are antiviral or antitumor agents. The compounds are exemplified by formulae I-XXVI.

In a second aspect, the invention comprises pharmaceutical compositions comprising a pharmaceutically acceptable carrier, excipient, or diluent and compounds according to formula I-XXVI or pharmaceutically acceptable salts thereof.

In a third aspect, the invention comprises methods for inhibiting a virus or tumor comprising contacting a cell in which inhibition is desired with a compound according to formula I-XXVI or a pharmaceutical composition according to the second aspect of the invention.

In a fourth aspect, the invention comprises methods for inhibiting a virus or tumor in a patient comprising administering to the patient a pharmaceutical composition according to formula I-XXVI.

In a fifth aspect, the invention comprises methods for treating a disease or condition in a patient, wherein the disease or condition involves a virus or is a tumor, comprising administering to the patient a pharmaceutical composition according to the second aspect of the invention. The disease or condition may be selected from ovarian cancer, cervical cancer, breast cancer, skin cancer, brain cancer, colorectal cancer, lung cancer, bone cancer, glioblastomas, influenza, or diseases caused by HPV, HIV, or HCV.

The foregoing only summarizes certain aspects of the invention and is not intended to be limiting in nature. These aspects and other aspects and embodiments are described more fully below. All references any sort referred to in this specification are hereby incorporated by reference in their entirety. In the event of a discrepancy between the express disclosure of this specification and the references incorporated by reference, the express disclosure of this specification shall control.

DETAILED DESCRIPTION OF THE INVENTION

The first aspect of the invention provides compounds of the formula

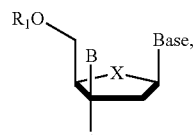

I

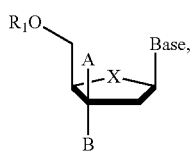

II

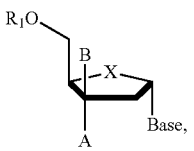

III

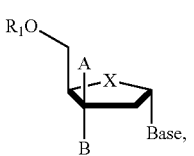

IV

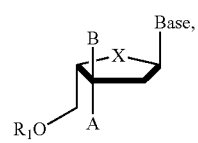

V

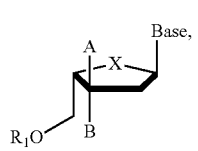

VI

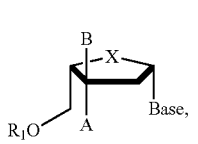

VII

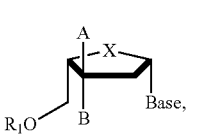

VIII

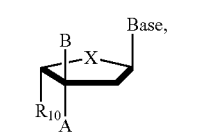

IX

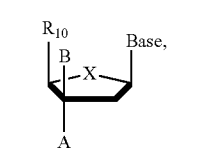

X

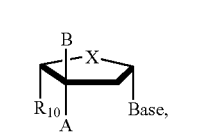

XI

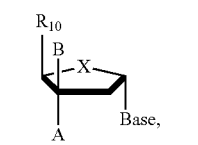

XII

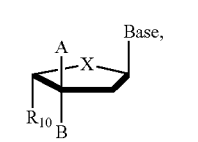

XIII

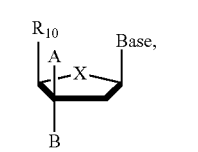

XIV

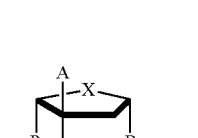

XV

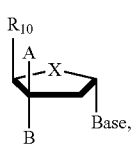

XVI

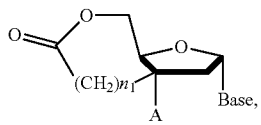

XVII

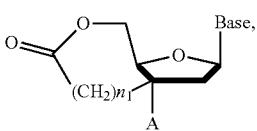

XVIII

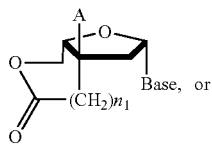

XIX

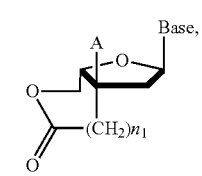

XX or pharmaceutically acceptable salts thereof, wherein

A and B are independently $C_1$-$C_6$ alkyl, $C_2$-$C_6$ alkenyl, $C_2$-$C_6$ alkynyl, mono- to per-halo $C_1$-$C_6$ alkyl, —C(O)—NR$_4$R$_{4a}$, —C(O)OR$_2$, (CH$_2$)$_{n1}$C(O)OR$_2$, —C(O)—R$_3$, or —(CH$_2$)$_n$M;

M is —OR$_1$, halo, mono- to per-halo $C_1$-$C_6$ alkyl, —SR$_1$, aryl, —CO$_2$R$_2$, —COR$_3$, heterocyclyl, heteroaryl, —NH(CO)R$_5$, —NR$_6$R$_{6a}$, —CONR$_4$R$_{4a}$, —NHSO$_2$R$_7$, —CO—CH$_2$OH, —SOR$_8$, —SO$_2$NR$_5$R$_{5a}$, —O(CO)R$_3$, —N$_3$, or $C_2$-$C_6$ alkynes, wherein each of the alkyl, heterocyclyl, aryl and heteroaryl is optionally substituted with one or more groups selected from $C_1$-$C_6$ alkyl, halo, —CN, —C(O)OR$_3$, —$C_1$-$C_6$ alkyl-C(O)OR$_3$, $C_1$-$C_6$ alkoxy, and mono- to per-halo $C_1$-$C_6$ alkyl;

n is 1 to 3;

$n_1$ is 0 to 3

R$_1$ is —H, —CH$_2$—P(O)(OH)$_2$, —P(O)(OH)$_2$, $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —C(O)OR$_3$, —$C_1$-$C_6$ alkyl-C(O)OR$_3$, $C_1$-$C_6$ alkoxy, and mono- to per-halo $C_1$-$C_6$ alkyl;

R$_2$ is —H, aryl, —$C_1$-$C_6$ alkylaryl, or $C_1$-$C_6$ alkyl;

R$_3$ is —H, $C_1$-$C_6$ alkyl, —(CH$_2$)$_m$C(O)OR$_2$ wherein m is 0 to 4, mono- to per-halo $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —C(O)OR$_3$, —$C_1$-$C_6$ alkyl-C(O)OR$_3$, $C_1$-$C_6$ alkoxy, and mono- to per-halo $C_1$-$C_6$ alkyl;

R$_4$ and R$_{4a}$ are independently —H, $C_1$-$C_6$ alkyl, —(CH$_2$)$_m$C(O)OR$_2$ wherein m is 0 to 4, mono- to per-halo $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —C(O)OR$_3$, —$C_1$-$C_6$ alkyl-C(O)OR$_3$, $C_1$-$C_6$ alkoxy, and mono- to per-halo $C_1$-$C_6$ alkyl; or R$_4$ and R$_{4a}$ together with the nitrogen to which they are attached form -(AA)$_x$, wherein x is 1 to 5, and AA is a natural, non-natural, D- or L-amino acid, wherein -(AA)$_x$ comprises a terminal —COOR$_3$ group wherein the carbonyl is protected or unprotected;

R$_5$ and R$_{5a}$ are independently —H, aryl, $C_1$-$C_6$ alkylaryl, $C_1$-$C_6$ alkyl, $C_1$-$C_6$ alkoxy;

R$_6$ and R$_{6a}$ are independently —H, aryl, $C_1$-$C_6$ alkylaryl, or $C_1$-$C_6$ alkyl;

R$_7$ is $C_1$-$C_6$ alkyl, aryl, $C_1$-$C_6$ alkylaryl, or mono- to per-halo $C_1$-$C_6$ alkyl;

R$_8$ is $C_1$-$C_6$ alkyl, aryl, $C_1$-$C_6$ alkylaryl, or mono- to per-halo $C_1$-$C_6$ alkyl;

R$_{10}$ is —C(O)OR$_3$, —CH$_2$—C(O)OR$_3$, —CONR$_4$R$_{4a}$, —CH$_2$—P(O)(OH)$_2$, —P(O)(OH)$_2$, $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —C(O)OR$_3$, —$C_1$-$C_6$ alkyl-C(O)OR$_3$, $C_1$-$C_6$ alkoxy, and mono- to per-halo $C_1$-$C_6$ alkyl;

X is O or S; and

Base is a purine derivative or a pyrimidine derivative.

Compounds of Formula XVII-XX are cyclic esters or lactones. The cyclic esters may undergo hydrolysis to yield the corresponding hydroxy carboxylic acid derivative. Thus, such cyclic ester compounds may function as prodrugs.

Embodiment A provides compounds according to Formula I-VIII, wherein

A and B are independently $C_1$-$C_4$ alkyl, mono- to per-halo $C_1$-$C_3$ alkyl, or —(CH$_2$)$_n$M;

M is mono- to per-halo $C_1$-$C_3$ alkyl, heterocyclyl, heteroaryl, or aryl optionally substituted with one or more groups selected from $C_1$-$C_6$ alkyl, halo, —CN, —C(O)OR$_3$, —$C_1$-$C_6$ alkyl-C(O)OR$_3$, $C_1$-$C_6$ alkoxy, and mono- to per-halo $C_1$-$C_6$ alkyl;

n is 1 to 3;

R$_1$ is —H, —CH$_2$—P(O)(OH)$_2$, —P(O)(OH)$_2$, $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —C(O)OR$_3$, —$C_1$-$C_6$ alkyl-C(O)OR$_3$, $C_1$-$C_6$ alkoxy, and mono- to per-halo $C_1$-$C_6$ alkyl;

R$_2$ is aryl or —$C_1$-$C_3$ alkylaryl;

R$_3$ is mono- to per-halo $C_1$-$C_6$ alkyl, or aryl optionally substituted with one or more groups selected from $C_1$-$C_6$ alkyl, halo, —CN, —C(O)OR$_3$, —$C_1$-$C_6$ alkyl-C(O)OR$_3$, $C_1$-$C_6$ alkoxy, and mono- to per-halo $C_1$-$C_6$ alkyl;

R$_4$ and R$_{4a}$ are independently $C_1$-$C_3$ alkyl, —(CH$_2$)$_m$C(O)OR$_2$ wherein m is 0 to 4, mono- to per-halo $C_1$-$C_3$ alkyl, aryl, or —$C_1$-$C_3$ alkylaryl, wherein each of the alkyl and aryl is optionally substituted with one or more groups selected from $C_1$-$C_6$ alkyl, halo, —CN, —C(O)OR$_3$, —$C_1$-$C_6$ alkyl-C(O)OR$_3$, $C_1$-$C_6$ alkoxy, and mono- to per-halo $C_1$-$C_6$ alkyl; or R$_4$ and R$_{4a}$ together with the nitrogen to which they are attached form -(AA)$_x$, wherein x is 1 to 5, and AA is a natural, non-natural, D- or L-amino acid, wherein -(AA)$_x$ comprises a terminal —COOR$_3$ group wherein the carbonyl is protected or unprotected;

R$_5$ and R$_{5a}$ are independently aryl or $C_1$-$C_3$ alkylaryl;

R$_6$ and R$_{6a}$ are independently aryl or $C_1$-$C_3$ alkylaryl;

R$_7$ is mono- to per-halo $C_1$-$C_3$ alkyl, aryl, or —$C_1$-$C_3$ alkylaryl; and Base is a purine derivative or a pyrimidine derivative selected from

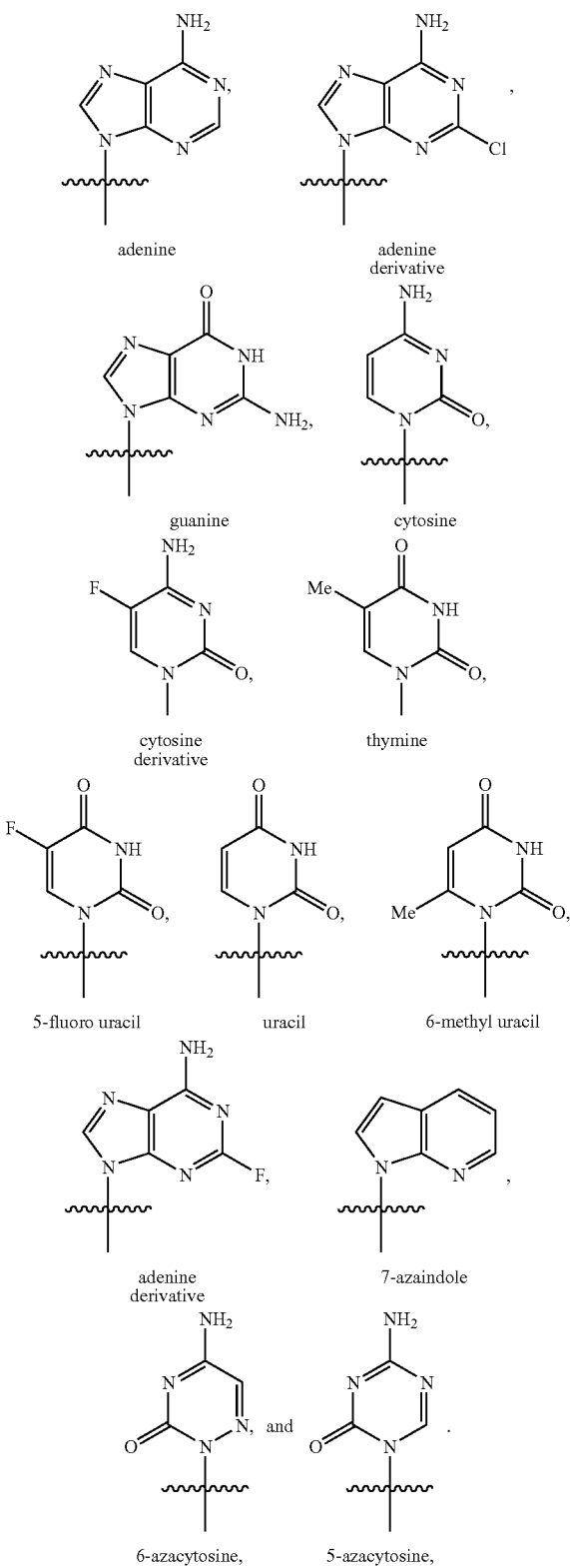

Embodiment B provides compounds according to Embodiment A, wherein A and B are independently —CH$_3$, —CH(CH$_3$)$_2$, —CF$_3$, —(CH$_2$)—CF$_3$, —(CH$_2$)-tetrazole, —(CH$_2$)-phenyl wherein the phenyl is optionally substituted with one or more groups selected from C$_1$-C$_3$ alkyl, —C$_1$-C$_3$ alkyl-C(O)OR$_3$, C$_1$-C$_3$ alkoxy, and mono- to per-halo C$_1$-C$_3$ alkyl.

Embodiment C provides compounds according to Embodiment A, wherein R$_1$ is —CF$_3$, —CH$_2$-phenyl, phenyl optionally substituted with halo, —CN, —CF$_3$, —C(O)OR$_3$, —CH$_2$—COOR$_3$, C$_1$-C$_3$ alkoxy, C$_1$-C$_4$ perfluoroalkyl, or C$_1$-C$_3$ alkyl.

Embodiment D provides compounds according to Embodiment A, wherein R$_2$ is phenyl or —CH$_2$-phenyl.

Embodiment E provides compounds according to Embodiment A, wherein R$_3$ is —CF$_3$, phenyl optionally substituted with halo, —CN, —CF$_3$, —C(O)OR$_3$, —CH$_2$—COOR$_3$, C$_1$-C$_3$ alkoxy, C$_1$-C$_4$ perfluoroalkyl, or C$_1$-C$_3$ alkyl.

Embodiment F provides compounds according to Embodiment A, wherein R$_4$ and R$_{4a}$ together with the nitrogen to which they are attached form -(AA)$_{1-4}$.

Embodiment G provides compounds according to Embodiment F, wherein R$_4$ and R$_{4a}$ together with the nitrogen to which they are attached form -(AA)$_3$.

Embodiment H provides compounds according to Embodiment G, wherein R$_4$ and R$_{4a}$ together with the nitrogen to which they are attached form -Arg-Arg-Arg.

Embodiment I provides compounds according to Embodiment A, wherein R$_5$ and R$_{5a}$ are independently —CH$_2$-phenyl or phenyl.

Embodiment J provides compounds according to Embodiment A, wherein R$_6$ and R$_{6a}$ are —CH$_2$-phenyl or phenyl.

Embodiment K provides compounds according to Embodiment A, wherein R$_7$ is 4-methylphenyl, phenyl or —CF$_3$ Embodiment L provides compounds according to Embodiment A, wherein Base is selected from

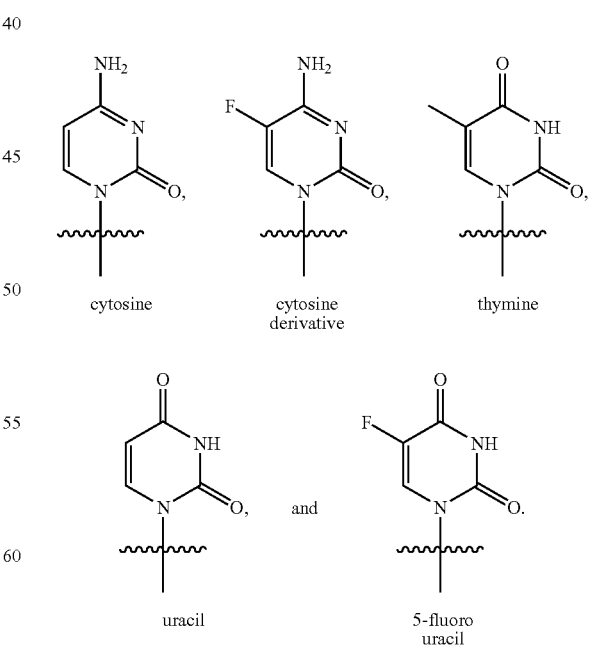

Embodiment M provides compounds according to Embodiment A, wherein Base is selected from

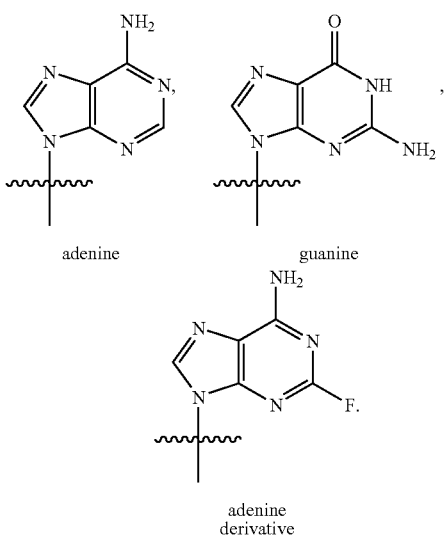

adenine  guanine adenine derivative

The invention also provides acyclic derivatives of the formula I-VIII. Accordingly, Embodiment N provides compounds of the formula

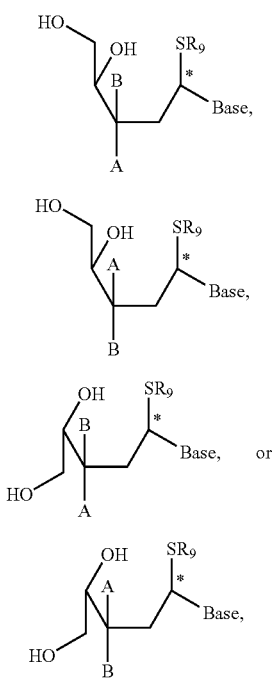

XXI

XXII

XXIII

XXIV or pharmaceutically acceptable salts thereof, wherein

A and B are independently $C_1$-$C_6$ alkyl, $C_2$-$C_6$ alkenyl, $C_2$-$C_6$ alkynyl, mono- to per-halo $C_1$-$C_6$ alkyl, —C(O)—$NR_4R_{4a}$, —C(O)$OR_2$, —C(O)—$R_3$, or —$(CH_2)_n$M;

M is —$OR_1$, halo, mono- to per-halo $C_1$-$C_6$ alkyl, —$SR_1$, aryl, —$CO_2R_2$, —$COR_3$, heterocyclyl, heteroaryl, —NH(CO)$R_5$, —$NR_6R_{6a}$, —$CONR_4R_{4a}$, —$NHSO_2R_7$, —CO—$CH_2OH$, —$SOR_8$, —$SO_2NR_5R_{5a}$, —O(C)$OR_3$, —$N_3$, or $C_2$-$C_6$ alkynes, wherein each of the alkyl, heterocyclyl, aryl and heteroaryl is optionally substituted with one or more groups selected from $C_1$-$C_6$ alkyl, halo, —CN, —C(O)$OR_3$, —$C_1$-$C_6$ alkyl-C(O)$OR_3$, $C_1$-$C_6$ alkoxy, and mono- to per-halo $C_1$-$C_6$ alkyl;

n is 1 to 3;

$R_1$ is —H, —$CH_2$—P(O)(OH)$_2$, —P(O)(OH)$_2$, $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —C(O)$OR_3$, —$C_1$-$C_6$ alkyl-C(O)$OR_3$, $C_1$-$C_6$ alkoxy, and mono- to per-halo $C_1$-$C_6$ alkyl;

$R_2$ is —H, aryl, —$C_1$-$C_6$ alkylaryl, or $C_1$-$C_6$ alkyl;

$R_3$ is —H, $C_1$-$C_6$ alkyl, —$(CH_2)_mC(O)OR_2$ wherein m is 0 to 4, mono- to per-halo $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —C(O)$OR_3$, —$C_1$-$C_6$ alkyl-C(O)$OR_3$, $C_1$-$C_6$ alkoxy, and mono- to per-halo $C_1$-$C_6$ alkyl;

$R_4$ and $R_{4a}$ are independently —H, $C_1$-$C_6$ alkyl, —$(CH_2)_mC(O)OR_2$ wherein m is 0 to 4, mono- to per-halo $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —C(O)$OR_3$, —$C_1$-$C_6$ alkyl-C(O)$OR_3$, $C_1$-$C_6$ alkoxy, and mono- to per-halo $C_1$-$C_6$ alkyl; or $R_4$ and $R_{4a}$ together with the nitrogen to which they are attached form -(AA)$_x$, wherein x is 1 to 5, and AA is a natural, non-natural, D- or L-amino acid, wherein -(AA)$_x$ comprises a terminal —$COOR_3$ group wherein the carbonyl is protected or unprotected;

$R_5$ and $R_{5a}$ are independently —H, aryl, $C_1$-$C_6$ alkylaryl, $C_1$-$C_6$ alkyl, $C_1$-$C_6$ alkoxy;

$R_6$ and $R_{6a}$ are independently —H, aryl, $C_1$-$C_6$ alkylaryl, or $C_1$-$C_6$ alkyl;

$R_7$ is $C_1$-$C_6$ alkyl, aryl, $C_1$-$C_6$ alkylaryl, or mono- to per-halo $C_1$-$C_6$ alkyl;

$R_8$ is $C_1$-$C_6$ alkyl, aryl, $C_1$-$C_6$ alkylaryl, or mono- to per-halo $C_1$-$C_6$ alkyl;

$R_9$ is —OH, $C_1$-$C_6$ alkyl, $C_1$-$C_6$ alkyl-aryl, aryl, wherein each of the alkyl and aryl is optionally substituted with one or more groups selected from $C_1$-$C_6$ alkyl, —OH, —CN, —C(O)$OR_3$, —$C_1$-$C_6$ alkyl-C(O)$OR_3$, $C_1$-$C_6$ alkoxy, and mono- to per-halo $C_1$-$C_6$ alkyl;

* indicates that the carbon atom is in the R or S configuration; and

Base is a purine derivative or a pyrimidine derivative.

Embodiment O provides compounds according to Embodiment N, wherein

A and B are independently $C_1$-$C_4$ alkyl, mono- to per-halo $C_1$-$C_3$ alkyl, or —$(CH_2)_n$M;

M is mono- to per-halo $C_1$-$C_3$ alkyl, heterocyclyl, heteroaryl, or aryl optionally substituted with one or more groups selected from $C_1$-$C_6$ alkyl, halo, —CN, —C(O)$OR_3$, —$C_1$-$C_6$ alkyl-C(O)$OR_3$, $C_1$-$C_6$ alkoxy, and mono- to per-halo $C_1$-$C_6$ alkyl;

n is 1 to 3;

$R_1$ is —H, —$CH_2$—P(O)(OH)$_2$, —P(O)(OH)$_2$, $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —C(O)$OR_3$, —$C_1$-$C_6$ alkyl-C(O)$OR_3$, $C_1$-$C_6$ alkoxy, and mono- to per-halo $C_1$-$C_6$ alkyl;

$R_2$ is aryl or —$C_1$-$C_3$ alkylaryl;

$R_3$ is mono- to per-halo $C_1$-$C_6$ alkyl, or aryl optionally substituted with one or more groups selected from $C_1$-$C_6$ alkyl, halo, —CN, —C(O)$OR_3$, —$C_1$-$C_6$ alkyl-C(O)$OR_3$, $C_1$-$C_6$ alkoxy, and mono- to per-halo $C_1$-$C_6$ alkyl;

$R_4$ and $R_{4a}$ are independently $C_1$-$C_3$ alkyl, —$(CH_2)_mC(O)OR_2$ wherein m is 0 to 4, mono- to per-halo $C_1$-$C_3$ alkyl, aryl, or —$C_1$-$C_3$ alkylaryl, wherein each of the alkyl and aryl is optionally substituted with one or more groups selected from $C_1$-$C_6$ alkyl, halo, —CN, —C(O)OR$_3$, —$C_1$-$C_6$ alkyl-C(O)OR$_3$, $C_1$-$C_6$ alkoxy, and mono- to per-halo $C_1$-$C_6$ alkyl; or $R_4$ and $R_{4a}$ together with the nitrogen to which they are attached form -(AA)$_x$, wherein x is 1 to 5, and AA is a natural, non-natural, D- or L-amino acid, wherein -(AA)$_x$ comprises a terminal —COOR$_3$ group wherein the carbonyl is protected or unprotected;

$R_5$ and $R_{5a}$ are independently aryl or $C_1$-$C_3$ alkylaryl;

$R_6$ and $R_{6a}$ are independently aryl or $C_1$-$C_3$ alkylaryl;

$R_7$ is mono- to per-halo $C_1$-$C_3$ alkyl, aryl, or —$C_1$-$C_3$ alkylaryl;

$R_9$ is $C_1$-$C_5$ alkyl, $C_1$-$C_3$ alkyl-aryl, aryl, wherein each of the alkyl and aryl is optionally substituted with one or more groups selected from $C_1$-$C_6$ alkyl, halo, —OH, —CN, —C(O)OR$_3$, —$C_1$-$C_6$ alkyl-C(O)OR$_3$, $C_1$-$C_6$ alkoxy, and mono- to per-halo $C_1$-$C_6$ alkyl; and Base is selected from

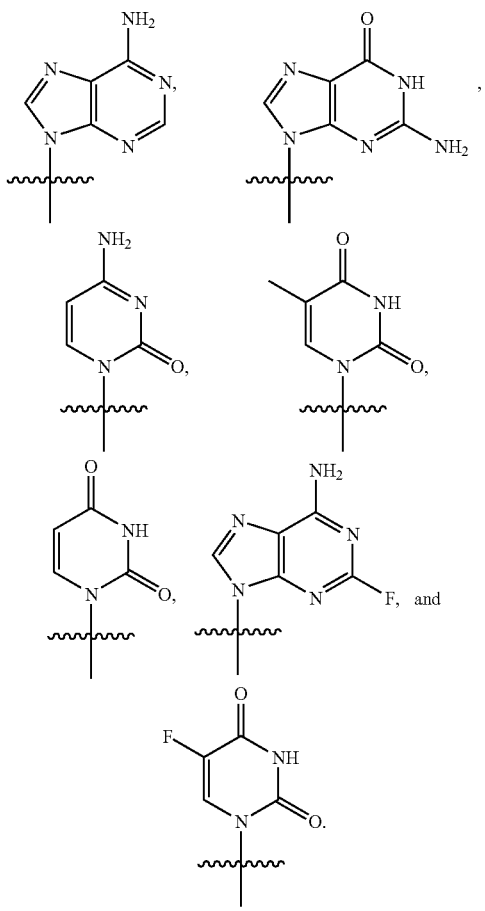

Embodiment P provides compounds according to Embodiment O, wherein A and B are independently —CH$_3$, —CH(CH$_3$)$_2$, —CF$_3$, —(CH$_2$)$_n$—CF$_3$, —(CH$_2$)$_n$-tetrazole, —(CH$_2$)$_n$-phenyl wherein the phenyl is optionally substituted with one or more groups selected from $C_1$-$C_3$ alkyl, —$C_1$-$C_3$ alkyl-C(O)OR$_3$, $C_1$-$C_3$ alkoxy, and mono- to per-halo $C_1$-$C_3$ alkyl.

Embodiment Q provides compounds according to Embodiment O, wherein $R_1$ is —CF$_3$, —CH$_2$-phenyl, phenyl optionally substituted with halo, —CN, —CF$_3$, —C(O)OR$_3$, —CH$_2$—COOR$_3$, $C_1$-$C_3$ alkoxy, $C_1$-$C_4$ perfluoroalkyl, or $C_1$-$C_3$ alkyl.

Embodiment R provides compounds according to Embodiment O, wherein $R_2$ is phenyl or —CH$_2$-phenyl.

Embodiment S provides compounds according to Embodiment O, wherein $R_3$ is —CF$_3$, phenyl optionally substituted with halo, —CN, —CF$_3$, —C(O)OR$_3$, —CH$_2$—COOR$_3$, $C_1$-$C_3$ alkoxy, $C_1$-$C_4$ perfluoroalkyl, or $C_1$-$C_3$ alkyl.

Embodiment T provides compounds according to Embodiment O, wherein $R_4$ and $R_{4a}$ together with the nitrogen to which they are attached form -(AA)$_{1-4}$. Preferably, $R_4$ and $R_{4a}$ together with the nitrogen to which they are attached form -(AA)$_3$. More preferably, $R_4$ and $R_{4a}$ together with the nitrogen to which they are attached form -Arg-Arg-Arg.

Embodiment U provides compounds according to Embodiment O, wherein $R_5$ and $R_{5a}$ are independently —CH$_2$-phenyl or phenyl.

Embodiment V provides compounds according to Embodiment O, wherein $R_6$ and $R_{6a}$ are —CH$_2$-phenyl or phenyl.

Embodiment W provides compounds according to Embodiment O, wherein $R_7$ is 4-methylphenyl, phenyl or —CF$_3$.

Embodiment X provides compounds according to Embodiment O, wherein Base is selected from

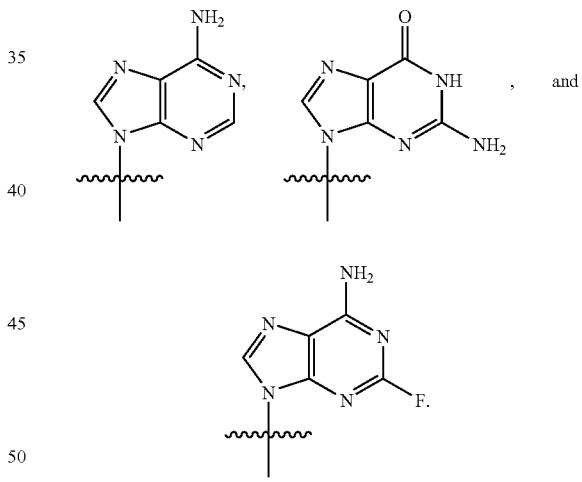

Embodiment Y provides compounds according to Embodiment O, wherein Base is selected from

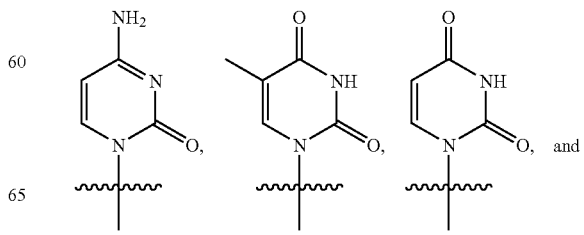

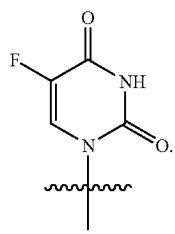

Embodiment Z provides compounds according Embodiment O, wherein $R_9$ is $C_1$-$C_5$ alkyl, $C_1$-$C_3$ alkyl-aryl, or aryl, wherein the alkyl is optionally substituted with —OH. Preferably, $R_9$ is methyl, ethyl, tert-butyl, benzyl, phenyl, or —CH$_2$CH$_2$OH.

In Embodiment AA, the invention provides compounds according to Embodiment A, wherein A and B are independently $C_1$-$C_3$ alkyl, —C(O)—NH$_2$, —C(O)OR$_2$, or —(CH$_2$)—OH; $R_1$ is —H; $R_2$ is $C_1$-$C_3$ alkyl; and Base is selected from

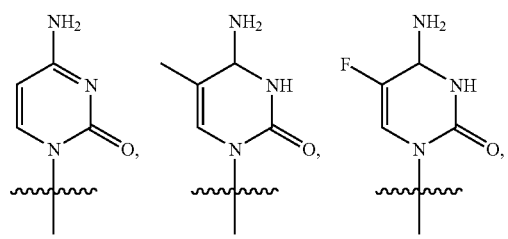

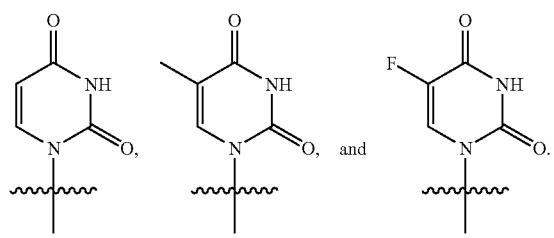

Embodiment BB provides compounds according Embodiment AA, wherein A and B are independently —CH$_3$, —C(O)OCH$_3$, or —(CH$_2$)—OH, and Base is

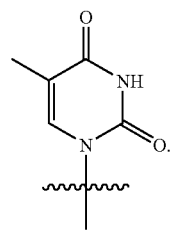 [SMILES: *n1cc(C)c(=O)[nH]c1=O]

Embodiment CC provides compounds according Embodiment AA, wherein A and B are independently —CH$_3$, —C(O)—NH$_2$, —C(O)OCH$_3$ or —(CH$_2$)—OH; and Base is

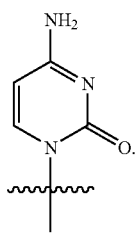 [SMILES: *n1ccc(N)nc1=O]

Embodiment DD provides compounds according Embodiment AA, wherein A and B are independently —CH$_3$, —C(O)—NH$_2$, —C(O)OCH$_3$, or —(CH$_2$)—OH; and Base is

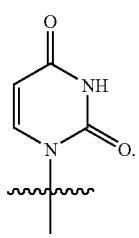 [SMILES: *n1ccc(=O)[nH]c1=O]

Embodiment EE provides compounds according Embodiment AA, wherein A and B are independently —CH$_3$ or —C(O)—NH$_2$; and Base is

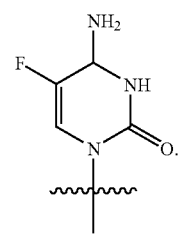

Embodiment FF provides compounds according Embodiment AA, wherein A and B are independently —CH$_3$, —C(O)OCH$_3$, or —(CH$_2$)—OH; and Base is

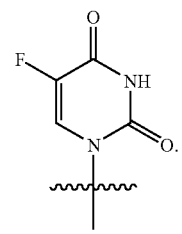

Embodiment GG provides compounds according Embodiment AA, wherein A and B are independently —CH$_3$, or —C(O)OCH$_3$; and Base is

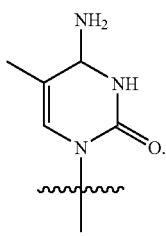 [SMILES: *N1C=C(C)C(N)NC1=O]

Embodiment HH provides compounds according Embodiment A, wherein A and B are independently —CH$_3$ or —(CH$_2$)—OH; and Base is

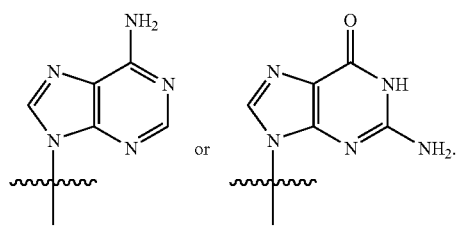 [SMILES: *n1cnc2c(N)ncnc21 ; "or" ; *n1cnc2c(=O)[nH]c(N)nc21]

Embodiment II provides compounds according to Formula XVII-XX, wherein A is —CH$_3$, n$_1$ is 0, and Base is

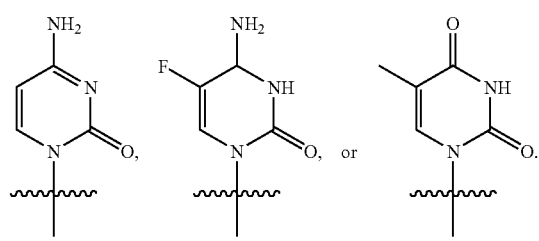

Embodiment JJ provides compounds according to Formula IX-XVI, wherein A and B are independently —CH$_3$ or —C(O)OCH$_2$CH$_3$; R$_{10}$ is —C(O)OCH$_2$CH$_3$; and Base is

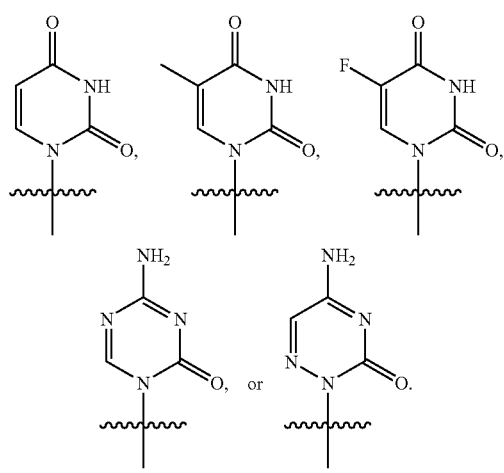

The invention further provides compounds of Formula XXV and XXVI,

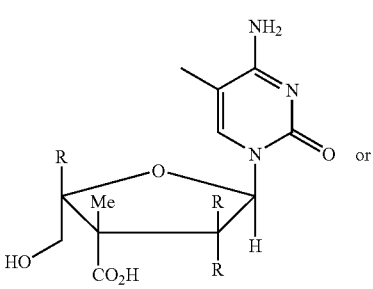
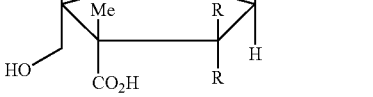
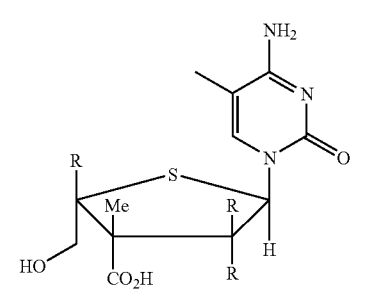

or pharmaceutically acceptable salts thereof, wherein R is —H or —OH.

In a second aspect, the invention comprises pharmaceutical compositions comprising a pharmaceutically acceptable carrier, excipient, or diluent and compound according to Formulae I-XXVI or pharmaceutically acceptable salts thereof.

In a third aspect, the invention comprises methods for inhibiting a virus or tumor comprising contacting a cell in which inhibition is desired with a compound according to Formula I-XXVI or a pharmaceutical composition according to the second aspect of the invention.

In a fourth aspect, the invention comprises methods for inhibiting a virus or tumor in a patient comprising administering to the patient a pharmaceutical composition according to Formulae I-XXVI.

In a fifth aspect, the invention comprises methods for treating a disease or condition in a patient, wherein the disease or condition involves a virus or is a tumor, comprising administering to the patient a pharmaceutical composition according to the second aspect of the invention. The disease or condition may be selected from ovarian cancer, cervical cancer, breast cancer, skin cancer, brain cancer, colorectal cancer, lung cancer, bone cancer, glioblastomas, influenza, or diseases caused by HPV, HIV, or HCV.

Table 1 illustrates certain embodiments of the compounds of the invention. The compounds of Table 1 merely illustrates some particular embodiments of the compounds of the invention, and do not limit in any way the scope of the invention.

TABLE 1
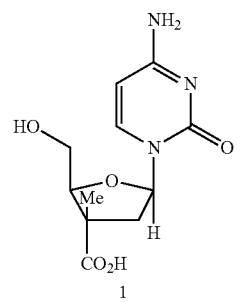
1
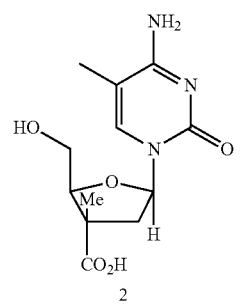
2
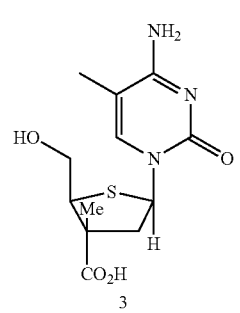
3
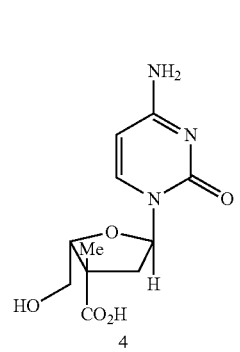
4
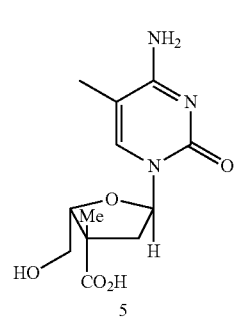
5
TABLE 1-continued
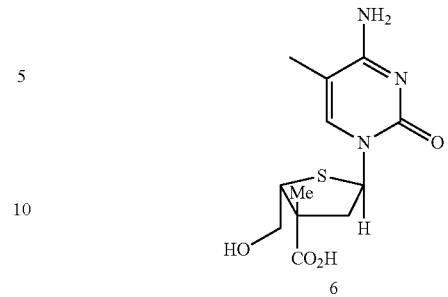
6
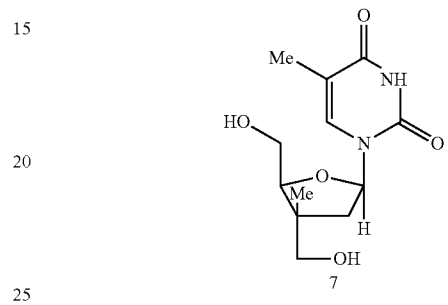
7
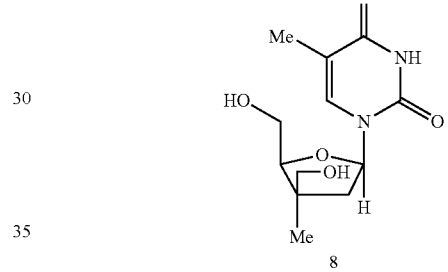
8
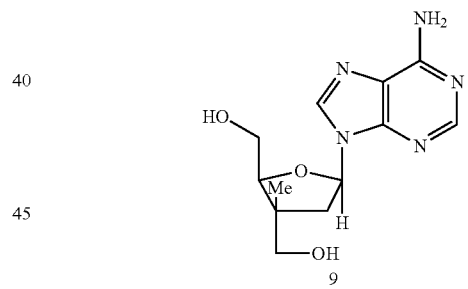
9
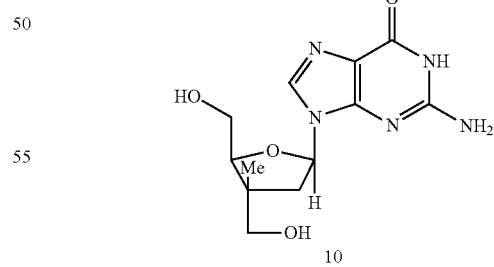
10
Definitions
As used in the present specification, the following words and phrases are generally intended to have the meanings as set forth below, except to the extent that the context in which they are used indicates otherwise or they are expressly defined to mean something different.

The symbol "—" means a single bond, "=" means a double bond, "≡" means a triple bond, "----" means a single or double bond. When a group is depicted removed from its parent formula, the "∿" symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —$CH_2CH_2$—. It is understood by one of ordinary skill in the art that the aforementioned descriptive techniques are common in the chemical arts to provide brevity and simplicity to description of otherwise complex structures.

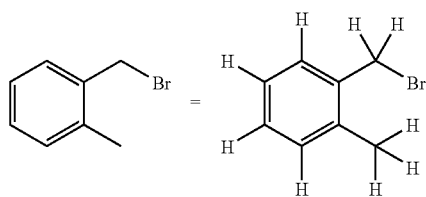

If a group R' (such as, R and $R_1$-$R_9$) is depicted as "floating" on a ring system, as for example in the formula:

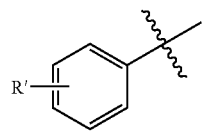

then, unless otherwise defined, a substituent R' may reside on any atom of the ring system, assuming replacement of a depicted, implied, or expressly defined hydrogen from one of the ring atoms, so long as a stable structure is formed.

If a group R' is depicted as floating on a fused ring system, as for example in the formulae:

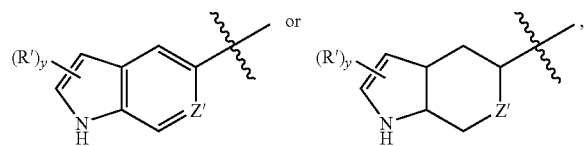

then, unless otherwise defined, a substituent R' may reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, Z' equals =CH— or —$CH_2$—) from one of the ring atoms, so long as a stable structure is formed. In the example depicted, the R' group may reside on either the 5-membered or the 6-membered ring of the fused ring system. In the formula depicted above, when y is 2 for example, then the two R' groups may reside on any two atoms of the ring system, again assuming each replaces a depicted, implied, or expressly defined hydrogen on the ring.

When a group R' is depicted as existing on a ring system containing saturated carbons, as for example in the formula:

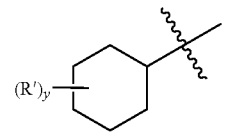

where, in this example, "y" can be more than one, assuming each replaces a currently depicted, implied, or expressly defined hydrogen on the ring; then, unless otherwise defined, where the resulting structure is stable, two R' groups may reside on the same carbon. A simple example is when R' is a methyl group; there can exist a geminal dimethyl on a carbon of the depicted ring (an "annular" carbon). In another example, two R' groups on the same carbon, including that carbon, may form a ring, thus creating a spirocyclic ring (a "spirocyclyl" group) structure with the depicted ring as for example in the formula:

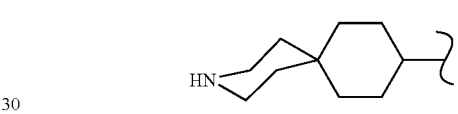

"Alkyl" is intended to include linear, branched, or cyclic hydrocarbon structures and combinations thereof, inclusively. For example, "$C_6$ alkyl" may refer to an n-hexyl, iso-hexyl, cyclobutylethyl, and the like. Lower alkyl refers to alkyl groups of from one to six carbon atoms. Examples of lower alkyl groups include methyl, ethyl, propyl, isopropyl, butyl, s-butyl, t-butyl, isobutyl, pentyl, hexyl and the like. Higher alkyl refers to alkyl groups containing more that eight carbon atoms. A "$C_0$" alkyl (as in "$C_0$-$C_6$ alkyl") is a covalent bond. Exemplary alkyl groups are those of $C_{20}$ or below. Cycloalkyl is a subset of alkyl and includes cyclic hydrocarbon groups of from three to thirteen carbon atoms. Examples of cycloalkyl groups include c-propyl, c-butyl, c-pentyl, norbornyl, adamantyl and the like. In this application, alkyl refers to alkanyl, alkenyl, and alkynyl residues (and combinations thereof); it is intended to include cyclohexylmethyl, vinyl, allyl, isoprenyl, and the like. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-ynyl groups; and for example, "propyl" or "$C_3$ alkyl" each include n-propyl, propenyl, and isopropyl. Alkyl also includes unsaturated hydrocarbon groups, such as alkenyl and alkynyl groups.

"Alkylene" refers to straight or branched chain divalent group consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene (—$CH_2CH_2$—), propylene (—$CH_2CH_2CH_2$—), dimethylpropylene (—$CH_2C(CH_3)_2CH_2$—), and cyclohexylpropylene (—$CH_2CH_2CH(C_6H_{13})$).

"Alkylidene" refers to a straight or branched chain unsaturated divalent group consisting solely of carbon and hydrogen atoms, having from two to ten carbon atoms, for example, ethylidene, propylidene, n-butylidene, and the like. Alkylidene is a subset of alkyl, referring to the same residues as alkyl, but having two points of attachment and, specifically, double bond unsaturation. The unsaturation present includes at least one double bond.

"Alkylidyne" refers to a straight or branched chain unsaturated divalent group consisting solely of carbon and hydrogen atoms having from two to ten carbon atoms, for example, propylid-2-ynyl, n-butylid-1-ynyl, and the like. Alkylidyne is a subset of alkyl, referring to the same residues as alkyl, but having two points of attachment and, specifically, triple bond unsaturation. The unsaturation present includes at least one triple bond.

Any of the above groups, "alkylene," "alkylidene" and "alkylidyne," when optionally substituted, may contain alkyl substitution which itself contains unsaturation. For example, 2-(2-phenylethynyl-but-3-enyl)-naphthalene (IUPAC name) contains an n-butylid-3-ynyl group with a vinyl substituent at the 2-position of said group.

"Alkoxy" or "alkoxyl" refers to the group —O-alkyl, for example including from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Aryl" refers to aromatic six- to fourteen-membered carbocyclic ring, and includes mono-, bicyclic, fused-polycyclic or fused ring system, or polycyclic groups, for example, benzene, naphthalene, acenaphthylene, anthracene, indane, tetralin, fluorene and the like. Aryl as substituents includes univalent or polyvalent substituents. As univalent substituents, the aforementioned ring examples are named, phenyl, naphthyl, acenaphthyl, anthracenyl, indanyl, tetralinyl, and fluorenyl.

When a group is referred to as "$C_1$-$C_6$ alkylaryl" or "$C_0$-$C_6$ alkylaryl", an aryl moiety is attached to a parent structure via an alkylene group. Examples include benzyl, phenethyl, and the like. Both the aryl and the corresponding alkylene portion of an "$C_1$-$C_6$ alkyl-aryl" or "$C_0$-$C_6$ alkyl-aryl" group may be optionally substituted.

"Cyclic ester" refers to a lactone produced from the condensation reaction of an alcohol and a carboxylic acid attached to a single molecule.

In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention may themselves have spiro rings attached thereto via a single ring atom of the fused-polycyclic.

"Halogen" or "halo" refers to fluorine, chlorine, bromine or iodine. The phrase "mono- to per- halogenated" when combined with another group refers to groups wherein one hydrogen, more than one hydrogen, or all hydrogens are replaced with a halo. For example, a "mono- to per- halogenated alkyl" would encompass groups such as —$CH_2F$, —$CH_2CHCl_2$ or —$CF_3$.

"Heteroatom" refers to O, S, N, or P.

"Heterocyclyl" and "heterocycloalkyl" refer to a stable three- to fifteen-membered ring substituent that consists of carbon atoms and from one to five heteroatoms selected from the group consisting of nitrogen, phosphorus, oxygen and sulfur. For purposes of this invention, the heterocyclyl substituent may be a monocyclic, bicyclic or tricyclic ring system, which may include fused or bridged ring systems as well as spirocyclic systems; and the nitrogen, phosphorus, carbon or sulfur atoms in the heterocyclyl group may be optionally oxidized to various oxidation states. In a specific example, the group —$S(O)_{0-2}$—, refers to —S—(sulfide), —S(O)— (sulfoxide), and —$SO_2$— (sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring substituent may be partially or fully saturated or aromatic. Examples of heterocyclyl groups include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, dioxaphospholanyl, and oxadiazolyl.

"Heteroaryl" refers specifically to an aromatic heterocyclyl group.

When a group is referred to as "$C_1$-$C_6$ alkylheterocyclyl," "$C_0$-$C_6$ alkyl-heterocyclyl," or "$C_1$-$C_6$ alkylheteroaryl," the heterocyclyl or heteroaryl is attached to a parent structure via one of an alkylene, alkylidene, or alkylidyne group. Examples include (4-methylpiperazin-1-yl)methyl, (morpholin-4-yl)methyl, (pyridine-4-yl)methyl, 2-(oxazolin-2-yl)ethyl, 4-(4-methylpiperazin-1-yl)-2-butenyl, and the like. Both the heterocyclyl and the corresponding alkylene, alkylidene, or alkylidyne portion of a heterocyclylalkyl group may be optionally substituted. "Heteroalicyclylalkyl" refers specifically to a heterocyclylalkyl where the heterocyclyl portion of the group is non-aromatic; and "heteroarylalkyl" refers specifically to a heterocyclylalkyl where the heterocyclyl portion of the group is aromatic Such terms may be described in more than one way, for example, "lower heterocyclylalkyl" and "heterocyclyl $C_{1-6}$alkyl" are equivalent terms. Additionally, for simplicity, the number of annular atoms (including heteroatoms) in a heterocycle may be denoted as "$C_x$-$C_y$," (as in "$C_x$-$C_y$-heterocyclyl" and "$C_x$-$C_y$-heteroaryl" (and the like)), where x and y are integers. So, for example, $C_5$-$C_{14}$-heterocyclyl refers to a 5 to 14 membered ring system having at least one heteroatom and not a ring system containing 5 to 14 annular carbon atoms.

Preferred heterocyclyls and heteroaryls include, but are not limited to, acridinyl, azocinyl, benzimidazolyl, benzofuranyl, benzothiophenyl, benzoxazolyl, benzthiazolyl, benztriazolyl, pyridotriazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,3,4-triazolyl, and xanthenyl.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted $C_1$-$C_6$ alkylaryl," both the "$C_1$-$C_6$ alkyl" portion and the "aryl" portion of the molecule may or may not be substituted. A list of exemplary optional substitutions is presented below in the definition of "substituted."

"Substituted" alkyl, aryl, heteroaryl, and heterocyclyl, refer respectively to alkyl, aryl, and heterocyclyl, one or more (for example up to about five, in another example, up to about three) hydrogen atoms are replaced by a substituent independently selected from: alkyl (for example, fluoromethyl), aryl (for example, 4-hydroxyphenyl), arylalkyl (for example, 1-phenyl-ethyl), heterocyclylalkyl (for example, 1-pyridin-3-yl-ethyl), heterocyclyl (for example, 5-chloro-pyridin-3-yl or 1-methyl-piperidin-4-yl), alkoxy, alkylenedioxy (for example methylenedioxy), amino (for example, alkylamino and dialkylamino), amidino, aryloxy (for example, phenoxy), arylalkyloxy (for example, benzyloxy), carboxy (—$CO_2H$), carboalkoxy (that is, acyloxy or —OC(=O)R), carboxyalkyl (that is, esters or —$CO_2R$), carboxamido, benzyloxycarbonylamino (CBZ-amino), cyano, acyl, halogen, hydroxy, nitro, sulfanyl, sulfinyl, sulfonyl, thiol, halogen, hydroxy, oxo, carbamyl, acylamino, and sulfonamido. And each substituent of a substituted group is optionally substituted, but these optional substituents themselves are not further substituted. Thus, an optionally substituted moiety is one that may or may not have one or more substituents, and each of the substituents may or may not have one or more substituents. But, the substituents of the substituents may not be substituted.

Some of the compounds of the invention may have imino, amino, oxo or hydroxy substituents off aromatic heterocyclyl systems. For purposes of this disclosure, it is understood that such imino, amino, oxo or hydroxy substituents may exist in their corresponding tautomeric form, i.e., amino, imino, hydroxy or oxo, respectively.

Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS).

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention. Thus, when a compounds is claimed without any stereochemistry designation, it is understood to include all possible stereoisomers, racemates, and as mixtures of enantiomers and diastereomers.

It is assumed that when considering generic descriptions of compounds of the invention for the purpose of constructing a compound, such construction results in the creation of a stable structure. That is, one of ordinary skill in the art would recognize that theoretically some constructs which would not normally be considered as stable compounds (that is, sterically practical and/or synthetically feasible).

When a particular group with its bonding structure is denoted as being bonded to two partners; that is, a divalent group, for example, —$OCH_2$—, then it is understood that either of the two partners may be bound to the particular group at one end, and the other partner is necessarily bound to the other end of the particular group, unless stated explicitly otherwise. Stated another way, divalent groups are not to be construed as limited to the depicted orientation, for example "—$OCH_2$-" is meant to mean not only "—$OCH_2$—" as drawn, but also "—$CH_2O$—."

Natural, non-natural, D- or L-amino acids include all known naturally occurring amino acids as well as synthetic amino acids.

Purine and pyrimidine derivatives include all naturally occurring purine and pyrimidine compounds, such as those that are found in nucleic acids. Purine and pyrimidine also include modified naturally occurring purines and pyrimidines, for example, modified with groups including, but not limited to, halo or alkyl groups.

A "protecting group" or "protective group" is any molecule introduced into another molecule by chemical modification of a functional group in order to obtain chemoselectivity in a subsequent chemical reaction. For example, a protecting group may be attached to any of the functional groups of the compounds according formulae I-VIII, or their intermediates. For example, a carbonyl group may be protected by converted it to an acetal or cyclic ketal. The acetal or cyclic ketal is then called a protecting group for the carbonyl. The acetal or cyclic ketal can be converted back to the carbonyl by reacting with an aqueous acid. This is referred to as deprotection. Protecting groups for alcohols include acetyl, tetrahydropyranyl ether, methoxymethyl ether, β-methoxyethoxymethyl ether, p-methoxybenzyl ether, methylthiomethyl ether, and silyl ether. Amine protecting groups include carbobenzyloxy group, tert-butyloxycarbonyl, 9-fluorenylmethyloxycarbonyl, and benzyl. Carbonyl protecting groups includes acetals and acylals. Carboxylic acid protecting groups include ethyl esters, benzyl esters, and silyl esters.

In addition to the preferred embodiments recited hereinabove, also preferred are embodiments comprising combinations of preferred embodiments.

Methods for the preparation and/or separation and isolation of single stereoisomers from racemic mixtures or non-racemic mixtures of stereoisomers are well known in the art. For example, optically active (R)- and (S)-isomers or L- and D-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin™ malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

"Pharmaceutically acceptable salts" of the compounds described herein are included within the scope of the present invention. Such salts may be prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the potassium, sodium, calcium and magnesium salts. Salts derived from pharmaceutically acceptable organic non-toxic bases include salts or primary, secondary, and tertiary amines, substituted amines including naturally occurring substituted amines, cyclic amines and basic ion exchange resin, such as isopropylamine, tri-methylamine, diethanolamine, diethylamine, triethylamine, tripropylamine, ethanolamine, 2-dimethylaminoethanol, 2-diethylamino-ethanol, tometheamine, lysine, arginine, histidine, caffeine, procaine, hydrabamine, choline, imidazole, betaine, ethylenediamine, glucosamine, methylglucamine, theobromine, purines piperazine, N,N-dibenzylethylenediamine, piperidine, N-ethyl-piperidine, morpholine, N-ethylmorpholine, polyamine resins and the like. (See, for example, S. M. Berge, et al., "Pharmaceutical Salts," J. Pharm. Sci., 1977; 66:1-19 which is incorporated herein by reference.)

"Pharmaceutically acceptable salts" also refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The compounds of the invention may also be prepared as prodrugs. Prodrugs refers to compounds that are transformed (typically rapidly) in vivo to yield the parent compound of the above formula I-XX, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the invention can also be used as pharmacological tools. In addition to their use as inhibitors, the compounds of the invention can be used to investigate the function and structure of cellular and viral components. Thus, the compounds of the invention can be used to investigate the interaction of cellular entities, or the interaction of cellular entities with viruses.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

General Administration

In the second aspect, the invention provides pharmaceutical compositions comprising a nucleotide analogue according to the invention and a pharmaceutically acceptable carrier, excipient, or diluent. In certain other preferred embodiments, administration may preferably be by the oral route. Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 90 kilograms, a dosage in the range of about 0.01 to about 50 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

General Synthetic Procedures

The compounds of the invention can be prepared by methods well known to those skilled in the art using reagents readily available. For example, the compounds of the invention comprising a quaternary carbon center may be prepared according to Cardinal-David et al. ("Synthesis of tertiary and quaternary stereogenic centers: a diastereoselective tandem reaction sequence combining Mukaiyama and free radical-based allylation," J. Org. Chem. 2005, 70(3): 776-784), which is incorporated by references in its entirety. For example, the compounds of the invention can be prepared according to reaction Schemes 1-5. In Schemes 1-5, one of Z and Y is A and the other is B, and R is —H.

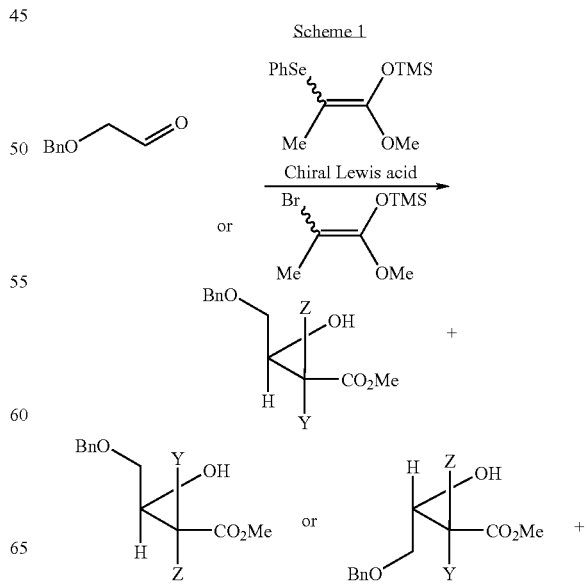

-continued

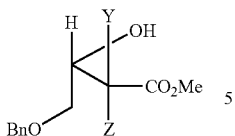

Z = CH₃, Y = Br(SePh)

The stereochemistry of the products in Scheme 1 is determined by the chiral Lewis acid used in the reaction. In Scheme 2, the allylation reaction uses allyltributylstannane for an allyl transfer reaction for the formation of functionalized quaternary center. This type of reaction is further described in Cardinal-David et al ("Synthesis of tertiary and quaternary stereogenic centers: a diastereoselective tandem reaction sequence combining Mukaiyama and free radical-based allylation," *J. Org. Chem.* 2005, 70, 776-784), which is incorporated by reference in its entirety.

Scheme 2

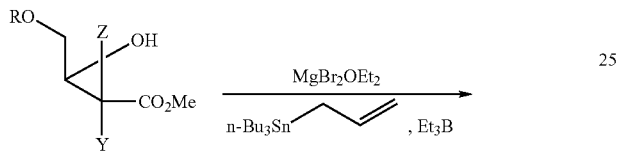

-continued

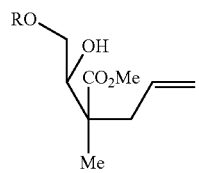

Scheme 3

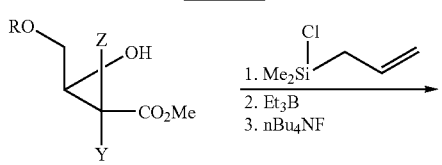

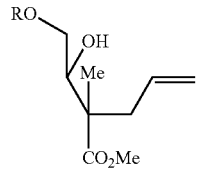

Scheme 4

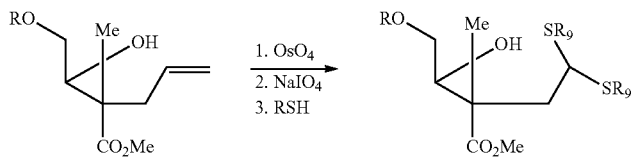

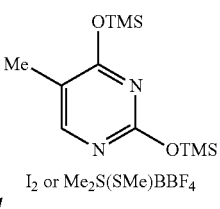

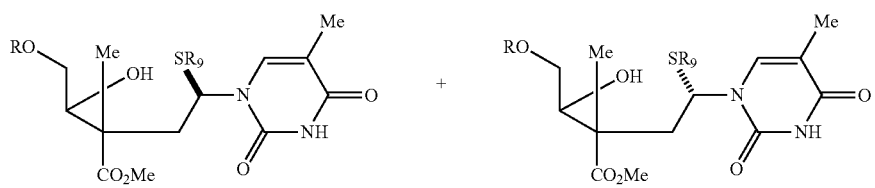

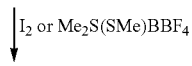

-continued

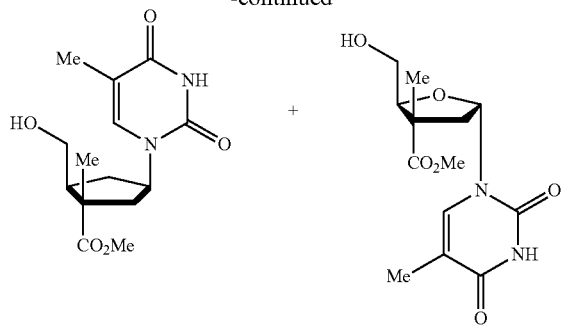

15

Scheme 5 illustrates one method for the synthesis of the 4' thio analogues of the compounds of the invention.

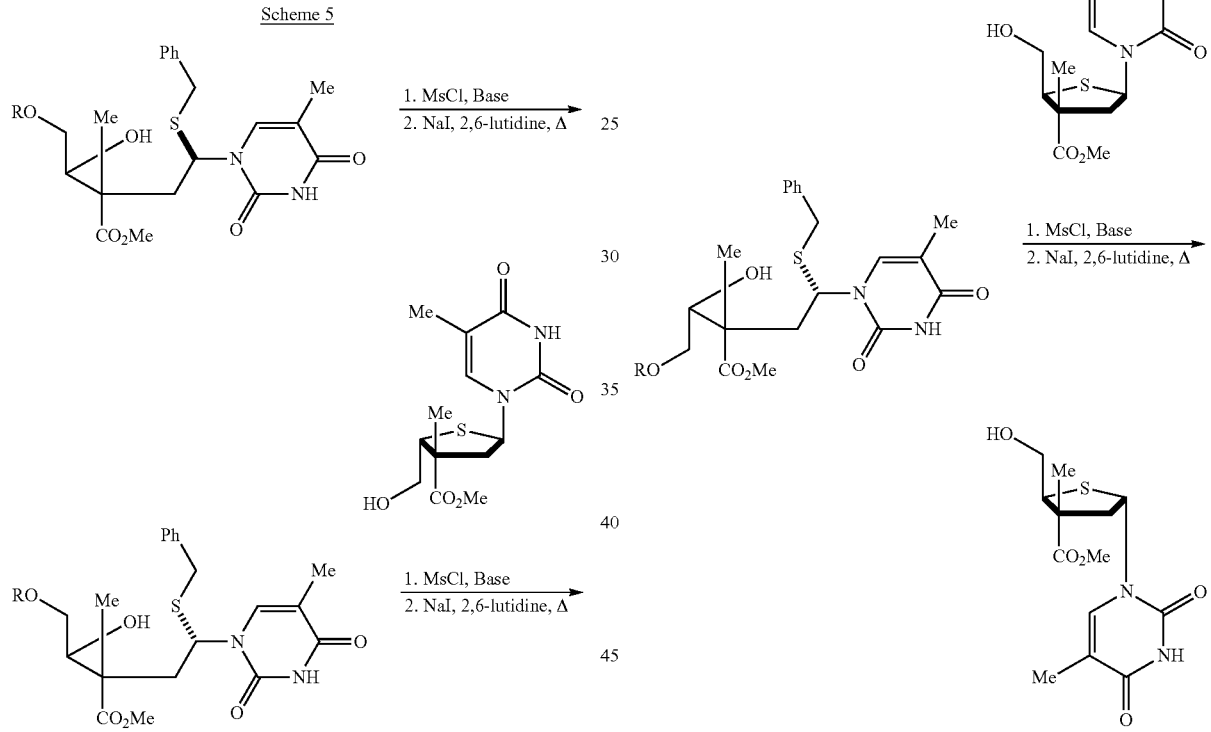

Scheme 5

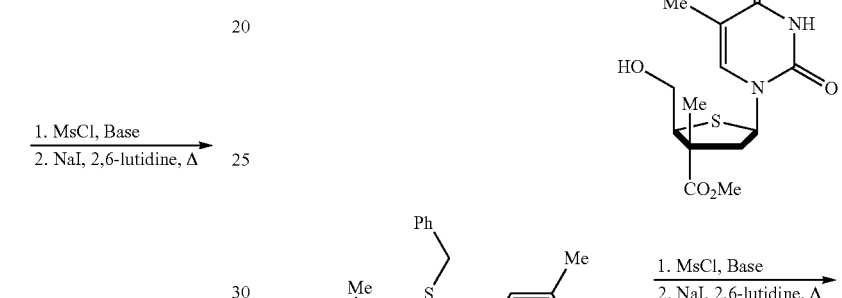

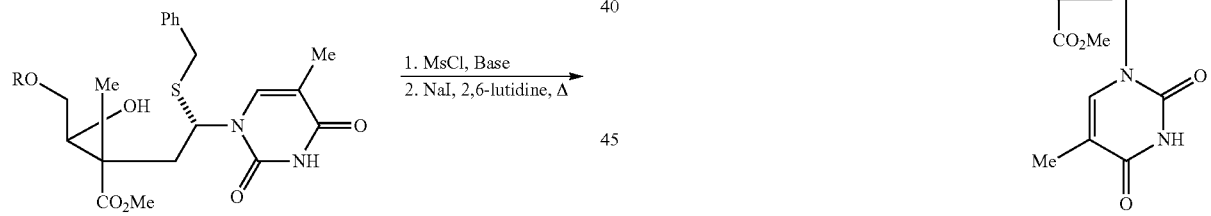

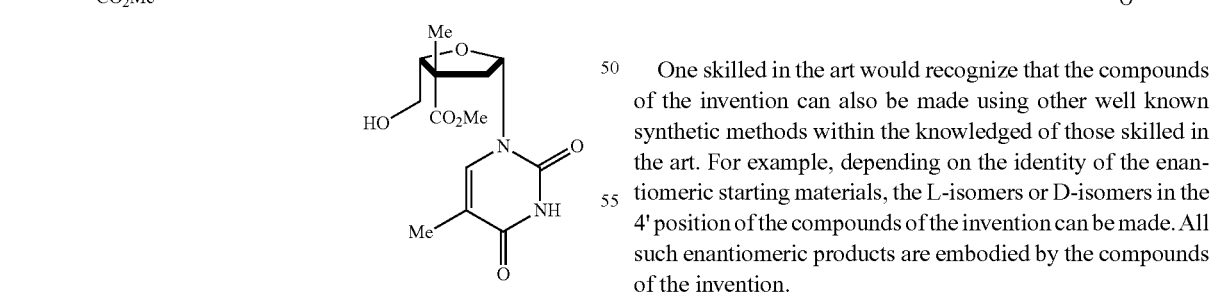

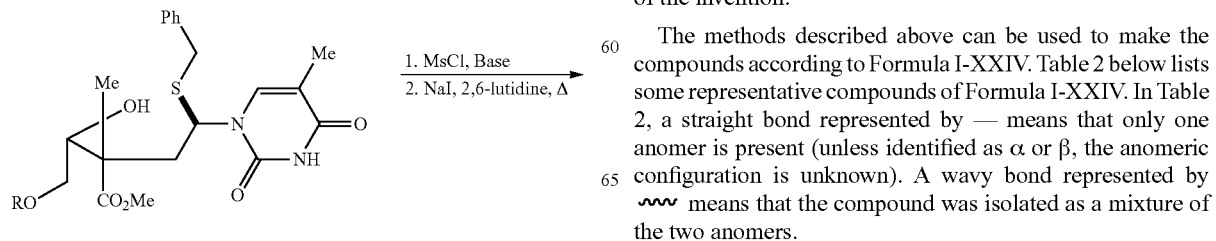

One skilled in the art would recognize that the compounds of the invention can also be made using other well known synthetic methods within the knowledge of those skilled in the art. For example, depending on the identity of the enantiomeric starting materials, the L-isomers or D-isomers in the 4' position of the compounds of the invention can be made. All such enantiomeric products are embodied by the compounds of the invention.

The methods described above can be used to make the compounds according to Formula I-XXIV. Table 2 below lists some representative compounds of Formula I-XXIV. In Table 2, a straight bond represented by — means that only one anomer is present (unless identified as α or β, the anomeric configuration is unknown). A wavy bond represented by ⌇ means that the compound was isolated as a mixture of the two anomers.

TABLE 2

| LCB # | Structure | MW |
|---|---|---|
| (±) 1000-1 | | $C_{13}H_{18}N_2O_6$ Exact Mass: 298.12 Mol. Wt.: 298.29 |
| (±) 1000-1 | | $C_{13}H_{18}N_2O_6$ Exact Mass: 298.12 Mol. Wt.: 298.29 |
| (±) 1002-1 | | $C_{12}H_{16}N_2O_6$ Exact Mass: 284.10 Mol. Wt.: 284.27 |
| (±) 1003-1 | | $C_{11}H_{16}N_2O_5$ Exact Mass: 256.11 Mol. Wt.: 256.26 |
| (±) 1004-1 | | $C_{12}H_{18}N_2O_5$ Exact Mass: 270.12 Mol. Wt.: 270.28 |
| (±) 1005-1 | | $C_{12}H_{16}N_2O_6$ Exact Mass: 284.10 Mol. Wt.: 284.27 |
| (±) 1006-1 | 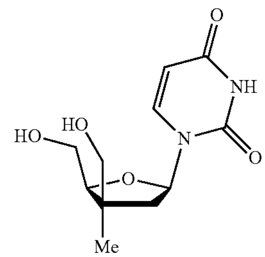 | $C_{11}H_{16}N_2O_5$ Exact Mass: 256.11 Mol. Wt.: 256.26 |
| (±) 1007-1 | 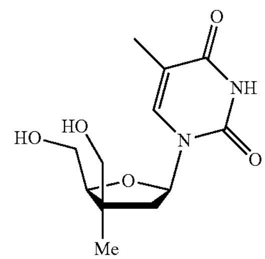 | $C_{12}H_{18}N_2O_5$ Exact Mass: 270.12 Mol. Wt.: 270.28 |
| (±) 1008-1 | 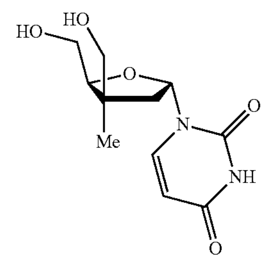 | $C_{11}H_{16}N_2O_5$ Exact Mass: 256.11 Mol. Wt.: 256.26 |
| (±) 1009-1 | β/α 13:1 | $C_{13}H_{18}N_2O_6$ Exact Mass: 298.12 Mol. Wt.: 298.29 |
| (±) 1010-1 | β/α 1:1 | $C_{13}H_{18}N_2O_6$ Exact Mass: 298.12 Mol. Wt.: 298.29 |
| (±) 1010-2 | β/α 1:1.7 | $C_{13}H_{18}N_2O_6$ Exact Mass: 298.12 Mol. Wt.: 298.29 |

TABLE 2-continued

| LCB # | Structure | MW |
|---|---|---|
| (±) 1011-1 | | $C_{11}H_{17}N_3O_4$ Exact Mass: 255.12 Mol. Wt.: 255.27 |
| (±) 1012-1 | | $C_{11}H_{17}N_3O_4$ Exact Mass: 255.12 Mol. Wt.: 255.27 |
| (±) 1015-1 | 1:0 | $C_{12}H_{15}FN_2O_6$ Exact Mass: 302.09 Mol. Wt.: 302.26 |
| (±) 1018-1 | | $C_{11}H_{16}N_4O_4$ Exact Mass: 268.12 Mol. Wt.: 268.27 |
| 1019-1 | | $C_{16}H_{22}N_2O_7$ Exact Mass: 354.1 Mol. Wt.: 354.4 |
| (±) 1020-1 | | $C_{12}H_{14}N_2O_5$ Exact Mass: 266.09 Mol. Wt.: 266.25 |
| (±) 1021-1 | | $C_{12}H_{18}N_2O_5$ Exact Mass: 270.12 Mol. Wt.: 270.28 |
| (±) 1022-1 | α anomer | $C_{12}H_{15}FN_2O_6$ Exact Mass: 302.09 Mol. Wt.: 302.26 |
| (±) 1023-1 | β anomer | $C_{12}H_{15}FN_2O_6$ Exact Mass: 302.09 Mol. Wt.: 302.26 |
| L- 1024-1 | | $C_{15}H_{19}FN_2O_7$ Exact Mass: 358.1 Mol. Wt.: 358.3 |
| L- 1025-1 | | $C_{15}H_{20}N_2O_7$ Exact Mass: 340.1 Mol. Wt.: 340.3 |
| (±) 1026-1 | α anomer | $C_{11}H_{15}FN_2O_5$ Exact Mass: 274.10 Mol. Wt.: 274.25 |
| (±) 1027-1 | β anomer | $C_{11}H_{15}FN_2O_5$ Exact Mass: 274.10 Mol. Wt.: 274.25 |
| (±) 1028-1 | | $C_{11}H_{12}FN_3O_4$ Exact Mass: 269.08 Mol. Wt.: 269.23 |
| (±) 1029-1 | | $C_{11}H_{13}N_3O_4$ Exact Mass: 251.1 Mol. Wt.: 251.2 |
| (±) 1030-1 | | $C_{11}H_{15}FN_4O_4$ Exact Mass: 286.1 Mol. Wt.: 286.3 |

TABLE 2-continued

| LCB # | Structure | MW |
|---|---|---|
| (±) 1032-1 | HO-CH2, Me, O, N (pyrimidine with Me, NH, =O), HO-CH2 | $C_{12}H_{18}N_2O_5$ Exact Mass: 270.1 Mol. Wt.: 270.3 |

BIOLOGICAL ASSAY

Biological Example 1

MTT Cell Proliferation Assay

The antitumor activities of the compounds of the invention were evaluated by a cellular proliferation assay. The MTT [3-(4,5-dimethylthiazol-2-yl)-2,5-diphenyltetrazolium bromide] cell proliferation assay, first described by Mosmann (Mosmann T., "Rapid colorimetric assay for cellular growth and survival: application to proliferation and cytotoxicity assays," J. Immunol. Methods 1983 Dec. 16; 65(1-2):55-63, and incorporated by reference in its entirety) is based on the ability of active mitochondrial reductase enzymes from viable cells to cleave the tetrazolium rings of the pale yellow MTT. The cleavage reaction form a purple formazan crystals which is largely impermeable to cell membranes resulting in its accumulation within healthy cells. Solubilisation of the cells by addition of a detergent liberates and solubilizes the formazan crystals. The number of surviving cells is directly proportional to the level of the formazan product created. The color can then be quantified spectrophotometrically. The production of purple formazan in cells treated with a compound is measured relative to the production in control cells, and dose-response curves can be generated. This assay measures the cell proliferation rate and conversely, when metabolic events lead to apoptosis or necrosis, the reduction in cell viability, thus also allowing the evaluation of the cytotoxicity of the analogues synthesized in the laboratory.

| Cell Lines Used in the Biological Examples |
|---|
| 1A6 |
| Urinary bladder; Epithelial Carcinoma |
| 22Rv1 |
| Prostate; Carcinoma |
| 786-O |
| Kidney; Renal cell adenocarcinoma |
| Colo 829 |
| Skin; Malignant melanoma |
| DLD-1 |
| Colon; Epithelial colorectal adenocarcinoma |
| Dukes' type C |
| HCC1143 |
| Mammary gland, breast (duct); Primary ductal carcinoma TNM stage IIA, grade 3 |
| MOLT-4 |
| T lymphoblast; Acute lymphoblastic leukemia |
| NCI H1395 |
| Lung; Adenocarcinoma stage 2 |
| NCI H2052 |
| Derived from pleural effusion; Mesothelioma stage 4 |
| Panc 02.03 |
| Pancreas; Adenocarcinoma |
| PFSK-1 |
| Brain cerebellum; Malignant primitive neuroectodermal tumor |
| ZR-75-1 |
| Mammary gland, breast (duct) derived from ascites; Epithelial ductal carcinoma |

Table 3 below shows the antitumor and antiproliferation activities of some compounds of the invention using cell types MOLT-4, NCI H1395, and NCI H2052.

TABLE 3

| | MOLT-4 | | | | NCI H1395 | | | | NCI H2052 | | | |
|---|---|---|---|---|---|---|---|---|---|---|---|---|
| Compound | n | $EC_{50}$ | $CC_{50}$ | SI | n | $EC_{50}$ | $CC_{50}$ | SI | n | $EC_{50}$ | $CC_{50}$ | SI |
| Cytarabine | 6 | 72 | >500 | >6.9 | 5 | 236 | 428 | 1.8 | 8 | 170 | >500 | >2.9 |
| LCB-1000 | 0 | — | — | — | 4 | 230 | >500 | >2.2 | 3 | 133 | 347 | 2.6 |
| LCB-1001 | 0 | — | — | — | 3 | 68 | >500 | >7.4 | 2 | 130 | 295 | 2.3 |
| LCB-1002 | 0 | — | — | — | 4 | 11 | 493 | 44.8 | 3 | 140 | 423 | 3.0 |
| LCB-1003 | 0 | — | — | — | 4 | 79 | 475 | 6.0 | 3 | 8 | 420 | 53 |
| LCB-1004 | 0 | — | — | — | 3 | 333 | >500 | >1.5 | 2 | >500 | >500 | n.d. |
| LCB-1005 | 0 | — | — | — | 2 | >500 | >500 | n.d. | 1 | >500 | >500 | n.d. |
| LCB-1006 | 0 | — | — | — | 2 | >500 | >500 | n.d. | 1 | >500 | >500 | n.d. |
| LCB-1007 | 0 | — | — | — | 2 | 140 | >500 | 3.6 | 2 | >500 | >500 | n.d. |
| LCB-1008 | 0 | — | — | — | 2 | >500 | >500 | n.d. | 1 | >500 | >500 | n.d. |
| LCB-1009 | 0 | — | — | — | 2 | >500 | >500 | n.d. | 3 | >500 | >500 | n.d. |
| LCB-1010 | 0 | — | — | — | 1 | >500 | >500 | n.d. | 3 | >500 | >500 | n.d. |
| LCB-1011 | 0 | — | — | — | 1 | >500 | >500 | n.d. | 1 | >500 | >500 | n.d. |
| LCB-1012 | 0 | — | — | — | 1 | >500 | >500 | n.d. | 1 | >500 | >500 | n.d. |
| LCB-1013 | 0 | — | — | — | 1 | >500 | >500 | n.d. | 2 | >500 | >500 | n.d. |
| LCB-1014 | 0 | — | — | — | 1 | >500 | >500 | n.d. | 2 | >500 | >500 | n.d. |
| LCB-1015 | 0 | — | — | — | 1 | >500 | >500 | n.d. | 2 | >500 | >500 | n.d. |
| LCB-1016 | 0 | — | — | — | 1 | >500 | >500 | n.d. | 1 | >500 | >500 | n.d. |
| LCB-1017 | 0 | — | — | — | 1 | >500 | >500 | n.d. | 1 | >500 | >500 | n.d. |
| LCB-1018 | 0 | — | — | — | 1 | >500 | >500 | n.d. | 1 | >500 | >500 | n.d. |
| LCB-1019 | 1 | >460 | >460 | n.d. | 1 | >460 | >460 | n.d. | 1 | >460 | >460 | n.d. |
| LCB-1020 | 1 | >500 | >500 | n.d. | 1 | >500 | >500 | n.d. | 1 | >500 | >500 | n.d. |
| LCB-1021 | 1 | >500 | >500 | n.d. | 1 | >500 | >500 | n.d. | 1 | >500 | >500 | n.d. |
| LCB-1022 | 1 | >500 | >500 | n.d. | 1 | >500 | >500 | n.d. | 1 | >500 | >500 | n.d. |

TABLE 3-continued

| | MOLT-4 | | | | NCI H1395 | | | | NCI H2052 | | | |
|---|---|---|---|---|---|---|---|---|---|---|---|---|
| Compound | n | $EC_{50}$ | $CC_{50}$ | SI | n | $EC_{50}$ | $CC_{50}$ | SI | n | $EC_{50}$ | $CC_{50}$ | SI |
| LCB-1023 | 1 | >500 | >500 | n.d. | 1 | >500 | >500 | n.d. | 1 | >500 | >500 | n.d. |
| LCB-1024 | 2 | 420 | >460 | >1.1 | 2 | 172 | >460 | >2.7 | 2 | >460 | >460 | n.d. |
| LCB-1025 | 1 | >460 | >460 | n.d. | 1 | >460 | >460 | n.d. | 1 | >460 | >460 | n.d. |
| LCB-1026 | 0 | — | — | — | 0 | — | — | — | 0 | — | — | — |
| LCB-1027 | 0 | — | — | — | 0 | — | — | — | 0 | — | — | — |
| LCB-1028 | 1 | >500 | >500 | n.d. | 1 | >500 | >500 | n.d. | 1 | >500 | >500 | n.d. |
| LCB-1029 | 1 | >500 | >500 | n.d. | 1 | >500 | >500 | n.d. | 1 | >500 | >500 | n.d. |
| LCB-1030 | 1 | >500 | >500 | n.d. | 1 | >500 | >500 | n.d. | 1 | 480 | >500 | >1.0 |
| LCB-1031 | 1 | >500 | >500 | n.d. | 1 | >500 | >500 | n.d. | 1 | >500 | >500 | n.d. |
| LCB-1032 | 1 | >500 | >500 | n.d. | 1 | >500 | >500 | n.d. | 1 | >500 | >500 | n.d. |

Table 4 below shows the antitumor and antiproliferation activities of some compounds of the invention using cell types Panc 02.03, PFSK-1, and ZR-75-1.

TABLE 4

| | Panc 02.03 | | | | PFSK-1 | | | | ZR-75-1 | | | |
|---|---|---|---|---|---|---|---|---|---|---|---|---|
| Compound | n | $EC_{50}$ | $CC_{50}$ | SI | n | $EC_{50}$ | $CC_{50}$ | SI | n | $EC_{50}$ | $CC_{50}$ | SI |
| Cytarabine | 3 | 300 | >500 | >1.7 | 9 | 360 | >500 | >1.4 | 8 | >500 | >500 | n.d. |
| LCB-1000 | 0 | — | — | — | 1 | >500 | >500 | n.d. | 1 | >500 | >500 | n.d. |
| LCB-1001 | 0 | — | — | — | 1 | >500 | >500 | n.d. | 1 | >500 | >500 | n.d. |
| LCB-1002 | 0 | — | — | — | 2 | >500 | >500 | n.d. | 2 | >500 | >500 | n.d. |
| LCB-1003 | 0 | — | — | — | 2 | >500 | >500 | n.d. | 2 | >500 | >500 | n.d. |
| LCB-1004 | 0 | — | — | — | 1 | >500 | >500 | n.d. | 1 | 420 | >500 | >1.2 |
| LCB-1005 | 0 | — | — | — | 1 | >500 | >500 | n.d. | 1 | >500 | >500 | n.d. |
| LCB-1006 | 0 | — | — | — | 1 | >500 | >500 | n.d. | 1 | >500 | >500 | n.d. |
| LCB-1007 | 0 | — | — | — | 1 | >500 | >500 | n.d. | 1 | 460 | >500 | >1.1 |
| LCB-1008 | 0 | — | — | — | 1 | >500 | >500 | n.d. | 1 | >500 | >500 | n.d. |
| LCB-1009 | 1 | >500 | >500 | n.d. | 3 | >500 | >500 | n.d. | 3 | >500 | >500 | n.d. |
| LCB-1010 | 1 | >500 | >500 | n.d. | 3 | >500 | >500 | n.d. | 2 | 180 | >500 | >2.8 |
| LCB-1011 | 0 | — | — | — | 1 | >500 | >500 | n.d. | 1 | >500 | >500 | n.d. |
| LCB-1012 | 0 | — | — | — | 1 | >500 | >500 | n.d. | 1 | >500 | >500 | n.d. |
| LCB-1013 | 2 | >500 | >500 | n.d. | 2 | 460 | >500 | >1.1 | 2 | 395 | >500 | >1.3 |
| LCB-1014 | 2 | >500 | >500 | n.d. | 2 | >500 | >500 | n.d. | 2 | >500 | >500 | n.d. |
| LCB-1015 | 2 | >500 | >500 | n.d. | 2 | 380 | >500 | >1.3 | 2 | 420 | >500 | >1.1 |
| LCB-1016 | 1 | >500 | >500 | n.d. | 1 | >500 | >500 | n.d. | 1 | >500 | >500 | n.d. |
| LCB-1017 | 1 | >500 | >500 | n.d. | 1 | >500 | >500 | n.d. | 1 | >500 | >500 | n.d. |
| LCB-1018 | 1 | >500 | >500 | n.d. | 1 | >500 | >500 | n.d. | 1 | >500 | >500 | n.d. |
| LCB-1019 | 0 | — | — | — | 1 | >460 | >460 | n.d. | 1 | >460 | >460 | n.d. |
| LCB-1020 | 0 | — | — | — | 1 | >500 | >500 | n.d. | 1 | >500 | >500 | n.d. |
| LCB-1021 | 0 | — | — | — | 1 | >500 | >500 | n.d. | 1 | >500 | >500 | n.d. |
| LCB-1022 | 0 | — | — | — | 1 | >500 | >500 | n.d. | 1 | >500 | >500 | n.d. |
| LCB-1023 | 0 | — | — | — | 1 | >500 | >500 | n.d. | 1 | >500 | >500 | n.d. |
| LCB-1024 | 0 | — | — | — | 2 | 190 | >460 | >2.4 | 2 | >460 | >460 | n.d. |
| LCB-1025 | 0 | — | — | — | 1 | >460 | >460 | n.d. | 1 | >460 | >460 | n.d. |
| LCB-1026 | 0 | — | — | — | 0 | — | — | — | 0 | — | — | — |
| LCB-1027 | 0 | — | — | — | 0 | — | — | — | 0 | — | — | — |
| LCB-1028 | 0 | — | — | — | 1 | >500 | >500 | n.d. | 1 | >500 | >500 | n.d. |
| LCB-1029 | 0 | — | — | — | 1 | >500 | >500 | n.d. | 1 | >500 | >500 | n.d. |
| LCB-1030 | 0 | — | — | — | 1 | >500 | >500 | n.d. | 1 | >500 | >500 | n.d. |
| LCB-1031 | 0 | — | — | — | 1 | >500 | >500 | n.d. | 1 | >500 | >500 | n.d. |
| LCB-1032 | 0 | — | — | — | 1 | >500 | >500 | n.d. | 1 | >500 | >500 | n.d. |

For Tables 3 and 4, the assays were performed with 1% DMSO. The abbreviation "n.d." means "not determined." The values $EC_{50}$, $CC_{50}$, and SI have the following definitions.

$EC_{50}$: Effective Concentration is the concentration necessary to reduce cell growth by 50% after a 72 hours period. Cell growth equals total cell count without any inhibitor after 72 hours minus initial cell count. Total cell counts after 72 hrs of growth range from 230 to 346% of initial cell counts depending on the cell line.

$CC_{50}$: Cytotoxic Concentration is the concentration causing a 50% cell death of the initial cell count over a 24 hours period. Total cell counts after 24 hrs of growth range from 103 to 109% of initial cell counts depending on the cell line.

SI: Selectivity Index is the ratio $CC_{50}/EC_{50}$.

n: Statistical sample size.

Biological Example 2

Phosphorylation Assay

Compounds of the invention were also tested in a phosphorylation assay using three deoxynucleoside kinases. The kinases include human dCK, which is responsible for the activation of numerous nucleoside analog prodrugs; *Drosophila melanogaster* dNK, which is the fastest known kinases with the broadest substrate specificity profile; and *Thermotoga maritima* thymidine kinase, which is a good surrogate for human thymidine kinase 1, a member of the distinct type II kinase subfamily. The compounds were at substrate concentration of 100 μM.

Kinetic assay. Substrate phosphorylation was determined using a spectrophotometric coupled-enzyme assay (Munch-Petersen et al. (2000) J. Biol. Chem. vol. 275 p. 66'73-66'79; Schelling et al. (2001) Anal. Biochem vol. 295 p. 82-8'7). Briefly, the individual nucleosides at 100 μM were prepared in reaction buffer containing 50 mM Tris-HCl (pH 7.5), 0.1 M KCl, 5 mM $MgCl_2$, 1 mM DTT, 1 mM ATP, 0.21 mM phosphoenolpyruvate, 0.18 mM NADH, and 2 units/ml pyruvate kinase and 2 units/ml lactate dehydrogenase (Roche Biochemicals, Indianapolis, Ind.). Assays were performed at 37° C. by measuring the absorbance change at 340 nm. The enzyme amount was adjusted to limit NADH turnover to 10% over the time of the experiment. All experiments were performed in triplicate.

| Substrate (at 100 μM) | Human dCK kinase ($10^{-3}$ μmol/min mg) | D. melanogaster dNK ($10^6$ μmol/min mg) | T. maritima TK ($10^{-3}$ μmol/min mg) |
|---|---|---|---|
| LCB-1001-1 | | <0.1 | <1 |
| LCB-1002-1 | | <0.1 | 2.2 |
| LCB-1004-1 | | 4.2 | 4.1 |
| LCB-1004-2 | | 3.7 | <1 |
| LCB-1005-1 | | <0.1 | <1 |
| LCB-1006-1 | | 0.22 | 2.7 |
| LCB-1007-1 | | 0.84 | 2.2 |
| LCB-1007-2 | | 0.74 | 2.2 |
| LCB-1008-1 | | 0.36 | <1 |
| LCB-1009-1 | | 3.49 | 11.9 |
| LCB-1009-2 | | 3.44 | 4.9 |
| LCB-1010-1 | | 2.84 | 6 |
| LCB-1010-2 | | 2.13 | 5.6 |
| LCB-1011-1 | 12 | 0.35 | |
| LCB-1012-1 | 17 | 5.94 | |
| LCB-1013-1 | <1 | <0.1 | |
| LCB-1014-1 | | 0.13 | <1 |
| LCB-1015-1 | | <0.1 | <1 |
| LCB-1020-1 | | <0.1 | <1 |
| LCB-1021-1 | | <0.1 | 2.2 |
| LCB-1022-1 | | 1.88 | 3 |
| LCB-1023-1 | | 0.33 | 2.1 |
| Ara C | 983 | 14.74 | |
| LCB-1016-1 | <1 | <0.1 | |
| LCB-1017-1 | <1 | <0.1 | |
| LCB-1018-1 | 63 | 0.2 | |
| LCB-1019-1 | | <0.1 | 6.1 |
| LCB-1024-1 | | <0.1 | 4.2 |
| LCB-1025-1 | | <0.1 | <1 |
| Thymidine | | 45.6 | 830 |

EXPERIMENTAL PROCEDURES AND EXPERIMENTAL DATA

General Methods. All reactions requiring anhydrous conditions were conducted under a positive nitrogen atmosphere, in oven-dried glassware, using standard syringe techniques. Tetrahydrofuran (THF) and ether were distilled from sodium/benzophenone immediately prior to use. Dichloromethane ($CH_2Cl_2$), dimethylsulfoxide (DMSO), i-$Pr_2$NEt, i-$Pr_2$NH, $Et_3$N and TMSCl were freshly distilled from $CaH_2$ under $N_2$ atmosphere. n-Butyllithium (1.6 M solution in hexane) was titrated prior to use (diphenylacetic acid end-point in dry THF). Methanol, benzene, p-toluenesulfonic acid, oxalyl chloride, sodium borohydride ($NaBH_4$), sodium hydride, potassium hydride, triethylsilyl chloride (TESCl; solution 1 M in THF), tert-butyldimethylsilyl chloride (TBSCl), benzyl bromide, tetrabutylammonium fluoride (solution 1 M in THF), acetic acid (99.9%), methyl-2-bromoacetate, 2-methyl-1,3-propanediol, palladium (10% on activated carbon), diphenyldiselenide, trichloroborane ($BCl_3$), tributyltin hydride, allyltributyltin, allyltrimethylsilane, triethylborane (solution 1 M in hexane), magnesium dibromide diethyletherate ($MgBr_2.OEt_2$), dimethylaluminium chloride ($Me_2AlCl$, solution 1M in hexane), trimethylaluminium ($AlMe_3$, solution 2 M in hexane) and boron trifluoride diethyletherate ($BF_3.OEt_2$) were used as received. Flash chromatography was performed on 0.040-0.063 mm silica gel using nitrogen pressure. Analytical thin-layer chromatography (TLC) was carried out on precoated (0.25 mm) silica gel plates. Melting points were determined on an electrothermal melting point apparatus and are uncorrected. $^1$H NMR spectra were recorded on a 500 MHz NMR spectrometer using $CDCl_3$ (δ=7.26 ppm) as an internal reference. $^{13}$C NMR spectra were recorded at 125 MHz using $CDCl_3$ (δ=77.1 ppm) as an internal reference. Infrared spectra were recorded using a FTIR spectrophotometer. Electron impact (EI) mass spectra were recorded on an instrument operating at 70 eV. FAB mass spectra were recorded on a VG AutospecQ either with or without ionization.

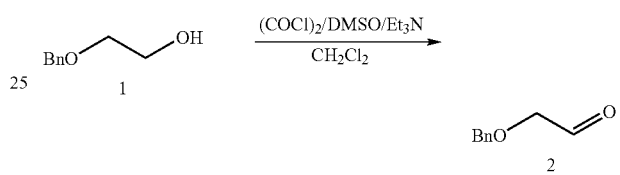

To a −78 C solution of oxalyl chloride (4.0 mL, 1.3 equiv) in $CH_2Cl_2$ (200 mL) was added dropwise a solution of dimethylsulphoxide (5.7 mL, 2.3 equiv) in $CH_2Cl_2$ (20 mL) The mixture was stirred for 15 min at −60 C, and a solution of the alcohol (5.0 mL, 35.1 mmol) in $CH_2Cl_2$ (20 mL) was added dropwise with stirring. After 45 min at −60° C., $Et_3$N (25 mL, 5 equiv) was added, and stirring continued for 45 min at 0° C. The mixture was allowed to warm to room temperature while being stirred and was then diluted with $Et_2$O (300 mL). The organic layer was washed with water (2×25 mL) and saturated aqueous NaCl, dried over $MgSO_4$, filtered, and concentrated under reduced pressure to give aldehyde 1. The aldehydes 1 can be used for the next step without purification. If the purification needed, 1 was purified by flash chromatography on silica gel using 30% EtOAc-hexanes (Pollex, A.; Millet, A.; Muller, J.; Hiersemann, M.; Abraham, L. *J. Org. Chem.* 2005; 70; 5579).

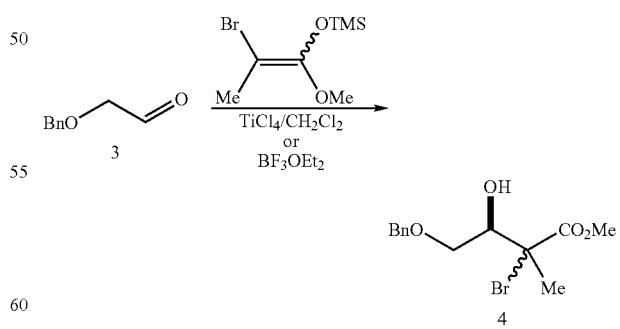

Bidentate Lewis Acid

To a solution of aldehyde 2 (1 equiv) in dry $CH_2Cl_2$ (0.25 M) was stirred for 10 min at −78° C. was slowly added $TiCl_4$ (1.1 equiv) under nitrogen atmosphere. A solution of the enoxysilane (1.5 equiv) in $CH_2Cl_2$ was immediately added under nitrogen atmosphere at the same temperature (−78° C.). The resulting solution was stirred until the aldehyde was completely consumed as indicated by TLC (generally 90 min). A saturated aqueous solution of NH₄Cl was poured into the reaction mixture. After the aqueous layer was extracted with EtOAc (3×), the organic layers were combined, successively washed with brine, dried (MgSO₄), filtered and concentrated. Purified on silica-gel 20% EtOAc-hexanes.

Reaction using TiCl₄:IR (neat) vmax. 3461.3, 2950, 2871.1, 1741.35 cm⁻¹; MS (EI) 339 (M+Na), 317 (M+1, 15%), 209 (M−108, 5%); ¹H (500 MHz, CDCl₃) δ 7.40-7.30 (m, 5H), 4.61 (d, 1H, J=11.9 Hz, 1H), 4.58 (dd, J=11.9 Hz, 2H), 4.38 (dd, J.=6.3, 3.2 Hz, 1H), 3.77 (dd, J=10.0, 3.2 Hz, 2H), 3.78 (s, 3H), 3.73 (dd, J=10.0, 6.3 Hz, 1H), (d, broad, J=5 Hz, 1H), 1.90 (s, 3H) ppm; ¹³C (125 MHz, CDCl3) δ 171.25, 137.79, 128.75, 128.66, 128.18, 128.08, 74, 66, 73, 80, 70.69, 60.90, 53.56, 23.44 ppm; HRMS calcd for C₁₃H₁₇BrO₄ (M) Found 316.0310.

Monodentare Lewis Acid

To a solution of aldehyde (1 equiv) and enoxysilane (2.5 equiv) in dry CH₂Cl₂ (0.1 M) at −78° C. was added the Lewis acid BF₃OEt₂ slowly (1.1 equiv) was added under nitrogen atmosphere at the same temperature (−78° C.). The resulting solution was stirred until the aldehyde was completely consumed by TLC; at least 60 min. When the reaction was completed, a saturated aqueous solution of NaHCO₃ was poured into the reaction mixture. After the aqueous layer was extracted with EtOAc (3×), the organic layers were combined, successively washed with brine, dried (MgSO₄), filtered and concentrated.

IR (neat) vmax. 3054.2, 2986.9, 2360.2, 1734.7, 1699.2 cm⁻¹; MS (FAB) 319 (10%, M+2), 299 (20%, M−18), 225 (25%, M−92), 209 (M/Z, M−108). 145 (12%, M−172), 91 (8%, M−226); ¹H (500 MHz, CDCl₃) δ 7.38-7.28 (m, 5H), 4.51 (dd, 1H, J=11.7 Hz, 1H), 4.35 (dd, J=6.10, 5.1 Hz, 1H), 3.70 (s, 3H), 3.69 (dd, J=10.0, 6.1 Hz, 1H), 3.61 (dd, J=10.0, 5.2 Hz, 1H), 2.6 (broad, 1H), 1.91 (s, 3H) ppm; ¹³C (125 MHz, CDCl₃) δ 170.9, 137.7, 128.69, 128.15, 128.09, 74.77, 73.83, 70.56, 64.90, 53.39, 23.71 ppm; HRMS calcd for C₁₃H₁₃BrO₄Na (M+Na) 339.02, found 339.02 (−0.46 ppm).

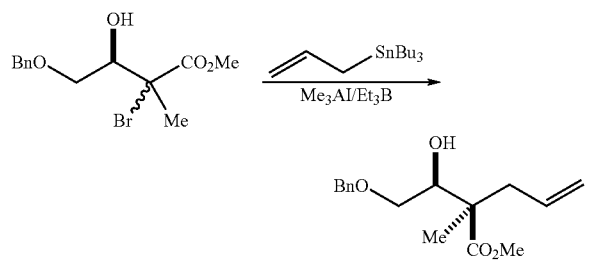

To a stirred solution of α-bromoester (1 equiv) in dry CH₂Cl₂ (0.1 M) at −78° C. was added AlMe₃ (2.5 equiv). The mixture was stirred for 10 min at the same temperature before allyltrimethylsilane (2 equiv) and Et₃B (0.2 equiv of a 1.0 M solution in hexanes) were added. The reaction was performed under anhydrous air atmosphere (O₂). 0.2 equiv of Et₃B was added with anhydrous air (syringed via a tube filled with Drierite™) every 20 min until the reaction was judged complete by TLC (approximately 4 h to 6 h). After completion, m- or p-Dinitrobenzene (0.2 equiv) was added to the solution and the mixture was stirred an additional 15 min at the same temperature. A saturated aqueous solution of NH₄Cl was then poured into the reaction mixture. If an emulsion appeared, it was controlled by adding a few drops of HCl (1M). After the aqueous layer was extracted with EtOAc (3×), the organic layers were combined, successively washed with brine, dried (MgSO₄), filtered and concentrated.

IR (neat) vmax. 3480.9, 2948.6, 1732.4, 1455.6 cm⁻¹; MS (EI) 301 (m/z, M+Na), 279 (21%, M+1), 261 (20%, M−17), 247 (47%, M−31), 229 (13%, M−49), 187 (8%, M−90), 171 (26%, M−107), 169 (36%, M−109), 131 (20%, M−147); ¹H (500 MHz, CDCl₃) δ 7.37-7.28 (m, 5H), 5.37-5.67 (m, 2H), 5.08 (dd, J=13.8, 1.5 Hz, 1H), 4.52 (dd, 1H, J=11.7 Hz, 1H), 3.83 (dd, J=5.85, 2.70 Hz, 1H), 3.62 (dd, J=9.7, 3.0 Hz, 1H), 3.60 (s, 3H), 3.55 (dd, J=9.7, 6.1 Hz, 1H), 2.56 (dd, J=13.5, 7.2 Hz, 1H), 2.26 (dd, J=13.5, 7.6 Hz, 1H), 3.3 (broad, 1H), 1.16 (s, 3H) ppm; ¹³C (125 MHz, CDCl₃) δ 176.43, 138.13, 128.62, 128.01, 118.90, 75.22, 73.84, 73.79, 71.31, 51.98, 49.11, 41.00, 17.86 ppm; HRMS calcd for C₁₆H₂₃O₄ (M) 278.1518, found 194.0791 (4.2 ppm).

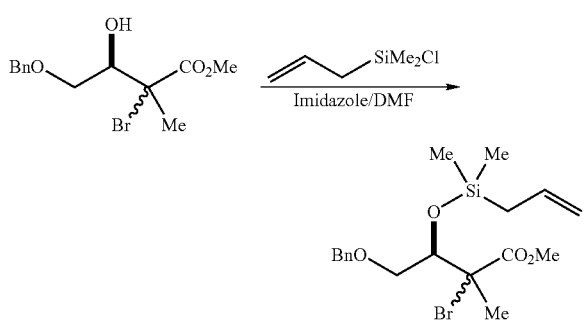

To a solution of alcohol in DMF (0.1 M) at 0 C under nitrogen atmosphere were added sequentially imidazole (2 equiv) and the allylchlorodimethylsilane (1.1 equiv). The mixture was stirred at the same temperature for 2 h before being diluted with Hexanes/water (50/50) and the phases separated, the aqueous layer was extracted with Hexanes (3×), the organic layers were combined, successively washed with brine, dried (MgSO₄), filtered and concentrated. Purification of the crude oil by flash column chromatography (hexane-EtOAc 93:7) gave silyl alcohol as colorless oil.

IR (neat) vmax. 2953.8, 1745.5 cm⁻¹; MS (EI) 437 (48%, M+Na), 357 (m/z, M−57), 259 (66%, M−155), 173 (56%, M−241), 143 (62%, M−271); ¹H (500 MHz, CDCl₃) δ 7.37-7.28 (m, 5H), 5.77-5.71 (m, 1H), 4.86-4.84 (m, 2H), 4.57 (s, 2H), 4.53 (dd, J=7.7, 2.1 Hz, 1H), 4.03 (dd, J=9.8, 2.0 Hz, 1H), 3.79 (s, 3H), 3.50 (dd, J=9.80, 7.70 Hz, 1H), 1.62 (s, 3H), 1.61-1.59 (m, 2H), 0.13 (s, 3H), 0.12 (s, 3H); ¹³C (125 MHz, CDCl₃) δ 170.98, 138.16, 134.37, 128.60, 127.88, 113.78, 76.17, 73.57, 72.21, 60.52, 53.23, 25.40, 22.36, −1.51, −1.84 ppm; HRMS calcd for C₁₈H₂₇NaO₄BrSi 437.07, found 437.07 (−1.11 ppm).

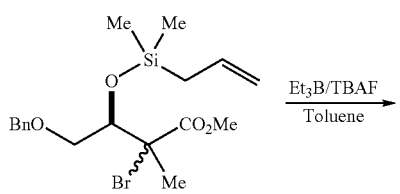

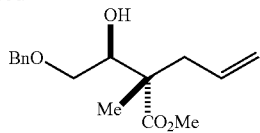

To a solution of bromide in Toluene (0.5 M) was added triethylborane (1 M in hexane, 1 equiv) at room temperature. The reaction mixture was stirred for 16 h before 2.5 equiv of TBAF was added. After 2 additional hours at room temperature, before being diluted with AcOEt (20 mL) and washed with HCl (1 M, 20 mL), water (20 mL), and brine (20 mL). The mixture was then dried over MgSO$_4$, filtered, and concentrated under reduced pressure. Purification of the crude oil by flash column chromatography (hexane-EtOAc 93:7) gave the pur alcohol.

IR (neat) vmax. 3480.9, 2949.0, 1729.9, 1117.1 cm$^{-1}$; MS (EI) (m/z, 301 M+Na), 279 (22%, M+1), 247 (43%, M−31), 171 (40%, M−107); $^1$H (500 MHz, CDCl$_3$) δ 7.39-7.28 (m, 5H), 5.77-5.71 (m, 2H), 4.54 (s, 2H) 4.00 (dd, J=7.0, 3.4 Hz, 1H), 3.63 (s, 3H), 3.56 (dd, J=9.8, 3.4 Hz, 1H), 3.51 (dd, J=9.8, 7.3 Hz, 1H), 2.55 (dd, J=13.7, 7.1 Hz, 1H), 2.32 (dd, J=13.7, 7.9 Hz, 1H), 1.19 (s, 3H) ppm; $^{13}$C (125 MHz, CDCl$_3$) δ 173.35, 135.49, 131.38, 126.12, 125.49, 125.46, 116.04, 71.63, 71.11, 68.97, 49.42, 46.74, 38.54, 14.66 ppm; HRMS calcd for C$_{16}$H$_{23}$O$_4$ (M+1) 279.1596, found 279.1588 (−1.2 ppm).

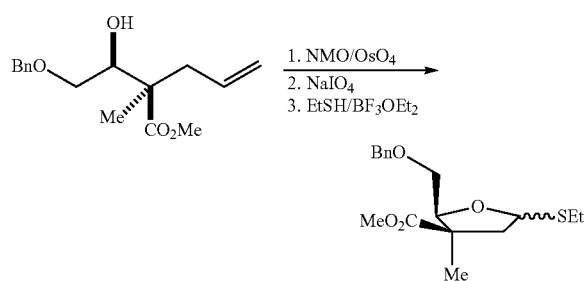

OsO$_4$ (1 mol %) was added to a solution of olefin (1 mmol) and N-methylmorpholine N-oxide (NMO) (1.5 mmol) in 10:1 acetone-H$_2$O (10 mL), and the reaction mixture was stirred at room temperature until the olefin was completely consumed by TLC for 3-4 hours (monitored by thin-layer chromatography (TLC)) (Steven, V.; Ley, Chandrashekar Ramarao; Ai-Lan Lee, Niels Østergaard, Stephen C. Smith, and Ian M. Shirley. *Org. Lett.* 2003, 5, 185-187). The reaction mixture was filtered, and the recovered precipitate was washed with H$_2$O and acetone. The filtrate was treated with saturated aqueous sodium metabisulfite (20 mL), extracted with ethyl acetate, and dried (MgSO4).

To a solution of the vicinal diol in CH$_2$Cl$_2$ (0.2 M) was added a suspension of silica gel-supported NaIO$_4$ reagent (2.0 g per mol of diol) at room temperature (Yong-Li Zhong, Tony,K. M.; Shing, *J. Org. Chem.* 1997, 62, 2622-2624). The reaction was monitored by TLC until disappearance of the vicinal diol (generally 5-10 min). The mixture was filtered through a path of celite, washed with CH$_2$Cl$_2$. Removal of the solvent afforded the aldehyde (Hemiacetal) that was pure enough for the next step.

To a solution of the crude aldehyde in dry CH$_2$Cl$_2$ (0.1 M) at −40° C. under nitrogen atmosphere were added ethanethiol and BF$_3$OEt$_2$ (1 equiv) at same temperature. The reaction was monitored by TLC until disappearance of the starting material (30 min). When the reaction was complete, a saturated aqueous solution of NaHCO$_3$ was poured into the reaction mixture. After the aqueous layer was extracted with EtOAc (3×), the organic layers were combined, successively washed with brine, dried (MgSO$_4$), filtered and concentrated.

IR (neat) vmax. 2949.8, 1730.3, 1452.6 cm$^{-1}$; MS (EI) (347, M+Na, 76%), 263 (m/z, M−61), 231 (94%, M−93), 141 (58%, M−183), $^1$H (500 MHz, CDCl$_3$) δ 7.36-7.26 (m, 5H), 5.59 (dd, J=7.3, 6.1 Hz, 1H), 4.60 (d, J=12.0 Hz, 1H), 4.52 (d, J=12.0 Hz, 1H), 4.10 (dd, J=6.10, 3.66 Hz, 1H), 3.70 (dd, J=11.0, 3.5 Hz, 1H), 3.65 (s, 3H), 3.53 (dd, J=11.0, 6.0 Hz, 1H), 3.0 (dd, J=13.5, 7.6 Hz, 2H), 4.54 (s, 2H) 4.00 (dd, J=7.0, 3.4 Hz, 1H), 3.63 (s, 3H), 3.56 (dd, J=9.8, 3.4 Hz, 1H), 3.51 (dd, J=9.8, 7.3 Hz, 1H), 2.55 (dd, J=13.7, 7.1 Hz, 1H), 2.32 (dd, J=13.7, 7.9 Hz, 1H), 1.19 (s, 3H) ppm; $^{13}$C (125 MHz, CDCl$_3$) δ 172.46, 135.68, 125.96, 125.92, 82.01, 81.33, 71.20, 71.03, 68.09, 66.49, 49.66, 48.71, 42.43, 23.62, 19.19, 12.78 ppm; HRMS calcd for C$_{17}$H$_{24}$O$_4$SNa (M+Na) 347.1293, found 347.1276 (−3.2 ppm).

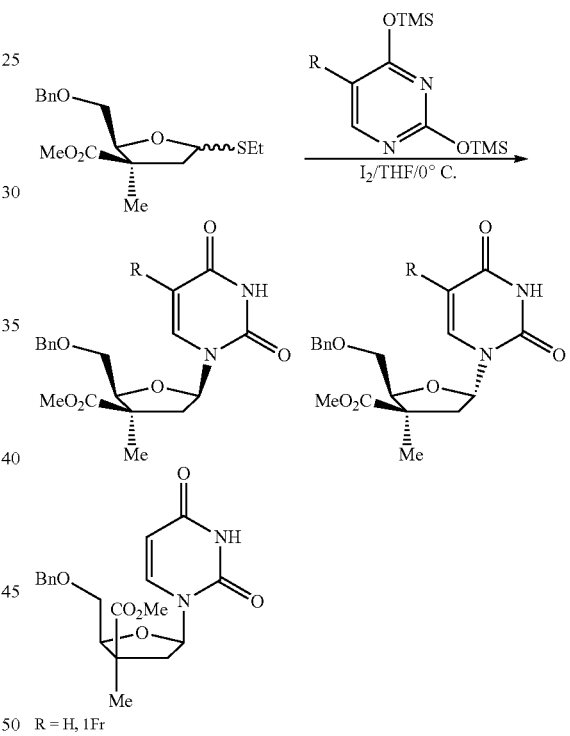

R = H, 1Fr

1Fr IR (neat) vmax. 1688.3, 1460.3, 1275.9 cm$^{-1}$; $^1$H (500 MHz, CDCl3) δ 8.86 (bd, 1H), 7.88 (d, J=8.2 Hz, 1H), 7.39-7.28 (4H), 6.27 (dd, J=5.59 (dd, J=7.3, 6.1 Hz, 1H), 4.60 (d, J=12.0 Hz, 1H), 4.52 (d, J=12.0 Hz, 1H), 4.10 (dd, J=6.10, 3.66 Hz, 1H), 3.70 (dd, J=110.0, 3.5 Hz, 1H), 3.65 (s, 3H), 3.53 (dd, J=11.0, 6.0 Hz, 1H), 3.0 (dd, J=13.5, 7.6 Hz, 2H), 4.54 (s, 2H), 4.00 (dd, J=7.0, 3.4 Hz, 1H), 3.63 (s, 3H), 3.56 (dd, J=9.8, 3.4 Hz, 1H), 3.51 (dd, J=9.8, 7.3 Hz, 1H), 2.55 (dd, J=13.7, 7.1 Hz, 1H), 2.32 (dd, J=13.7, 7.9 Hz, 1H), 1.19 (s, 3H) ppm; $^{13}$C (125 MHz, CDCl$_3$) δ 172.46, 135.68, 125.96, 125.92, 82.01, 81.33, 71.20, 71.03, 68.09, 66.49, 49.66, 48.71, 42.43, 23.62, 19.19, 12.78 ppm; HRMS calcd for C$_8$H18OS2 (M) 194.0799, found 194.0791 (4.2 ppm); Anal. calcd C8H18OS2: C, 49.44; H, 9.33. Found: C, 49.43; H, 9.48.

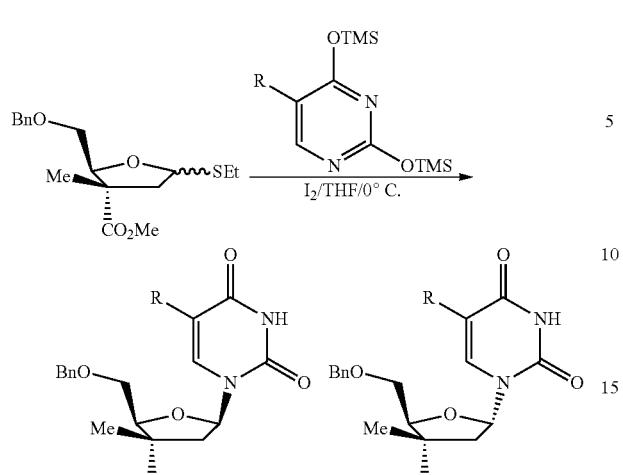

To a solution of thioacetal (1 equiv.) in dry THF (0.1 M) was added, at 0° C., the appropriate persilylated purine or pyrimidine base solution (1 M) in CH$_2$Cl$_2$ (2.0 equiv). Iodine (2.0 equiv) was added afterward. The resulting solution was stirred for 30 min at 0° C. or until the thioacetal was completely consumed (generally 30 min to 2 hours), as determined by TLC. Diluted with AcOEt (5× total volume). A saturated aqueous solution of NaHCO$_3$/Na$_2$S$_2$O$_3$ (1/1) was poured into the reaction mixture. After the separation, the aqueous layer was extracted with EtOAc (2×), the organic layers were combined, washed with brine dried (MgSO$_4$), and concentrated.

1Fr $^1$H (500 MHz, CDCl$_3$) δ 8.00 (bd, 1H), 7.89 (d, J=8.2 Hz, 1H), 7.40-7.29 (4H), 6.27 (dd, J=5.59 (dd, J=7.3, 6.1 Hz, 1H), 4.60 (d, J=12.0 Hz, 1H), 4.52 (d, J=12.0 Hz, 1H), 4.10 (dd, J=6.10, 3.66 Hz, 1H), 3.70 (dd, J=110.0, 3.5 Hz, 1H), 3.65 (s, 3H), 3.53 (dd, J=11.0, 6.0 Hz, 1H), 3.0 (dd, J=13.5, 7.6 Hz2H), 4.54 (s, 2H) 4.00 (dd, J=7.0, 3.4 Hz, 1H), 3.63 (s, 3H), 3.56 (dd, J=9.8, 3.4 Hz, 1H), 3.51 (dd, J=9.8, 7.3 Hz, 1H), 2.55 (dd, J=13.7, 7.1 Hz, 1H), 2.32 (dd, J=13.7, 7.9 Hz, 1H), 1.19 (s, 3H) ppm; $^{13}$C (125 MHz, CDCl$_3$) δ 172.46, 135.68, 125.96, 125.92, 82.01, 81.33, 71.20, 71.03, 68.09, 66.49, 49.66, 48.71, 42.43, 23.62, 19.19, 12.78 ppm; HRMS calcd for C8H18OS2 (M) 194.0799, found 194.0791 (4.2 ppm);

To a solution of thioacetal (1 equiv.) in dry THF (0.1 M) was added, at 0° C., the appropriate persilylated purine or pyrimidine base solution (1 M) in CH$_2$Cl$_2$ (2.0 equiv). Iodine (2.0 equiv) was added afterward. The resulting solution was stirred for 30 min at 0° C. or until the thioacetal was completely consumed (generally 30 min to 2 hours), as determined by TLC. Diluted with AcOEt (5× total volume). A saturated aqueous solution of NaHCO$_3$/Na$_2$S$_2$O$_3$ (1/1) was poured into the reaction mixture. After the separation, the aqueous layer was extracted with EtOAc (2×), the organic layers were combined, washed with brine dried (MgSO$_4$), and concentrated.

R=H, $^1$H (500 MHz, CDCl$_3$) δ 8.00 (bd, 1H), 7.89 (d, J=8.2 Hz, 1H), 7.40-7.29 (4H), 6.27 (dd, J=5.59 (dd, J=7.3, 6.1 Hz, 1H), 4.60 (d, J=12.0 Hz, 1H), 4.52 (d, J=12.0 Hz, 1H), 4.10 (dd, J=6.10, 3.66 Hz, 1H), 3.70 (dd, J=110.0, 3.5 Hz, 1H), 3.65 (s, 3H), 3.53 (dd, J=11.0, 6.0 Hz, 1H), 3.0 (dd, J=13.5, 7.6 Hz2H), 4.54 (s, 2H) 4.00 (dd, J=7.0, 3.4 Hz, 1H), 3.63 (s, 3H), 3.56 (dd, J=9.8, 3.4 Hz, 1H), 3.51 (dd, J=9.8, 7.3 Hz, 1H), 2.55 (dd, J=13.7, 7.1 Hz, 1H), 2.32 (dd, J=13.7, 7.9 Hz, 1H), 1.19 (s, 3H) ppm; $^{13}$C (125 MHz, CDCl$_3$) δ 172.46, 135.68, 125.96, 125.92, 82.01, 81.33, 71.20, 71.03, 68.09, 66.49, 49.66, 48.71, 42.43, 23.62, 19.19, 12.78 ppm; HRMS calcd for C8H18OS$_2$ (M) 194.0799, found 194.0791 (4.2 ppm).

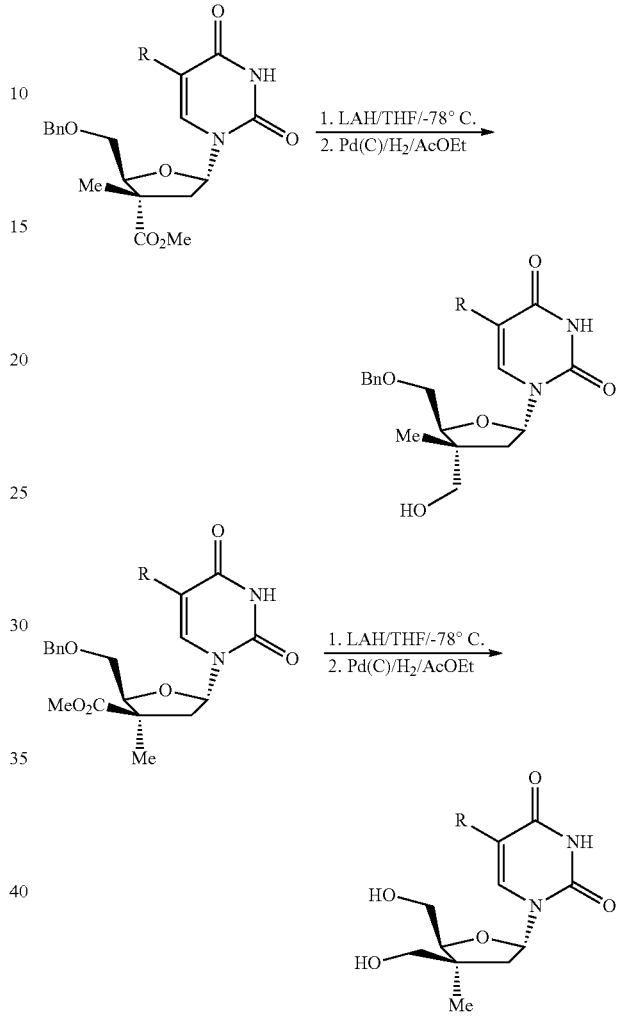

Cleavage of Benzyl Ether

A suspension of LiAlH$_4$ (1 g, 26 mmol) in anhydrous THF (20 mL) was refluxed for 90 min. After the mixture was cooled to −40° C. The ester (26 mmol), was added dropwise to the THF suspension (obtained above) of the reagent and the new mixture stirred at −40° C. for 2 hours. (Until the precipitate disappeared). The reaction was then carefully quenched by successive addition of 1 mL of H$_2$O, 1 mL of 10% NaOH, and 3 mL of H$_2$O. Stirring was maintained until the new precipitate became white and powdered. MgSO$_4$ was added. After filtration, the precipitate was carefully rinsed with CH$_2$Cl$_2$ (5×10 mL), and the combined organic phases were dried over MgSO$_4$, and concentrated in vacuo to give the crude products which were used for the next step.

To a solution of ester (0.1 M) in THF, at −40° C., was added dropwise (1.5 equiv.) lithium aluminum hydride (1 M in THF), The resulting solution was stirred for 2-3 hours at −40° C. or until the ester was completely consumed, as determined by TLC. A saturated aqueous solution of Na$_2$SO$_4$ was poured into the reaction mixture (1.92 ml/mmol of LiAlH$_4$). Stirring was maintained until the precipitate became white and powdered. MgSO$_4$ was added, the stirring was maintained for a while, after filtration, the precipitate was carefully rinsed with AcOEt, and concentrated in vacuums to give the crude product which were used for the next step.

The ether derivative (1 equiv) was dissolved in AcOEt (0.1 M). Pd/C (10%) was added. The solution was stirred under a hydrogen atmosphere at 25° C. for 5 hours. The palladium was filtered off and the solvent removed under vacuum to afford colorless oil. The resulting residue was purified by column chromatography (10% MeOH in CH$_2$Cl$_2$) to yield 120 mg of 7 as a white solid (65% over 2 steps).

The Examples below further illustrate how some specific embodiments of the compounds of the invention were prepared. A skilled artisan would recognize that the methods in the Examples below serve to further illustrate the invention, and does not limit in any way the scope of the invention.

EXAMPLE 1

Preparation of LCB-1025, LCB-1024, LCB-1019, LCB-1009, LCB-1010, and LCB-1032

Compounds LCB-1019, LCB-1024, and LCB-1025 were prepared starting from commercial L-malic acid according Scheme 6.

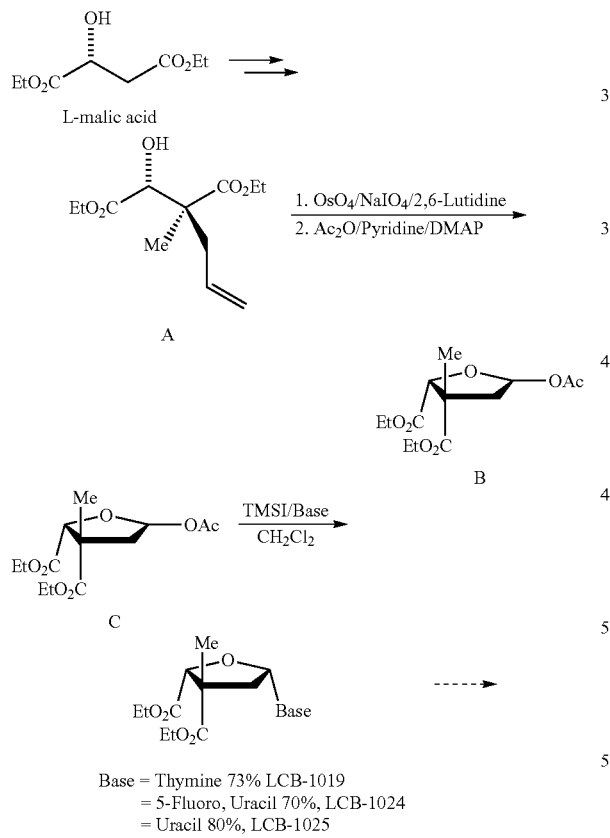

The compound A was prepared using a procedure developed by (Alan R. Battersby, J. Chem. Soc., Chem. Commun., 1989, 1116-1119).

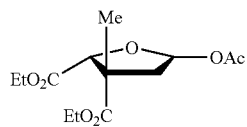

(2R,5S)-diethyl 5-acetoxy-3-methyltetrahydrofuran-2,3-dicarboxylate

To a solution of compound A (890 mg, 3.6 mmol) in dioxane-water (3:1, 36 mL) were added 2,6-lutidine (0.845 mL, 2 equiv.), OsO4 (10% in water, 2.2 mL, 0.01 equiv.), and NaIO$_4$ (3.1 g, 4 equiv.). The reaction was stirred at 25° C. and monitored by TLC. After the reaction was completed. The mixture was filtered over celite. AcOEt (200 mL) was added, and washed with a statured NaHSO$_3$ (3×20 mL). The water layer was extracted three times (AcOEt). The combined organic layer was washed with brine and dried over Na$_2$SO$_4$. The solvent was removed, and the product was used for the next step without purification. The crude acetate was dissolved in CH$_2$Cl$_2$ (5 mL), a mixture Ac$_2$O/Pyridine 20/20 mL) was added at 0° C., followed by DMAP (45 mg). When the reaction was completed (30 min.). EtOAc was added (100 mL) and water (20 mL), The organic layer was extracted and washed with a saturated aqueous solution of NaHCO$_3$ (3×20 mL) and brine (20 ml). The solvent was removed dried (MgSO$_4$), filtered and concentrated and purified by on silica gel Hexane 100% to 10% EtOAc-Hexanes.

$^1$H NMR (500 MHz, CDCl$_3$) δ 6.51 (1H, s), 4.49 (1H, s), 4.28-4.41 (4H, m), 3.02 (1H, dd, J=6.1 Hz, 13.9 Hz), 1.97 (1H, dd, J=2.2, 13.9 Hz), 1.62 (3H, s), 1.30 (3H, t, J=7 Hz), 1.26 (t, 3H).

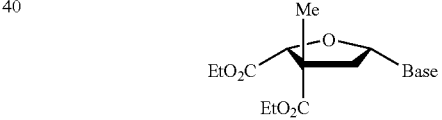

To a solution of acetate in CH$_2$Cl$_2$ (1 mmol in 15 mL of CH$_2$Cl$_2$) and the base (1M in CH$_2$Cl$_2$) 2 equivalents was added the TMSI (1 equiv.). After the reaction was completed (2 hours). EtOAc was added and the mixture was washed with a mixture of a statured solution of NaHCO$_3$ and Na$_2$SO$_3$. The water layer was extracted two times with EtOAc. The organic layer was combined and washed with brine, dried over MgSO$_4$ and concentrated.

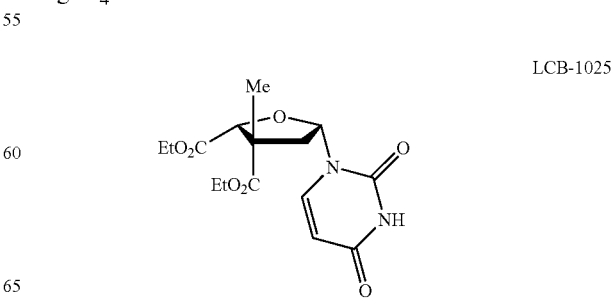

LCB-1025: $C_{15}H_{22}N_2O_7$

(2R,5S)-diethyl 5-(2,4-dioxo-3,4-dihydropyrimidin-1 (2H)-yl)-3-methyltetrahydrofuran-2,3-dicarboxylate The compound was purified on silica gel using 100% Hexanes to 50% AcOEt-Hexanes (80%); $[\alpha]^{25}_D = +69°$ (c 1.02, $CH_2Cl_2$). $^1H$ NMR (500 MHz, $CDCl_3$) δ 8.17 (1H, d, J=8.3 Hz), 7.98 (1H, bd), 6.29 (1H, t, J=6.4 Hz), 5.78 (1H, d, J=8.3 Hz), 4.35 (1H, s), 4.32-4.19 (2H, m), 4.14 (2H, q, J=7.0 Hz), 4.47 (1H, s), 2.81 (dd, 1H, J=6.8, 13.8 Hz), 2.40 (1H, dd, J=6.2, 13.8 Hz), 1.61 (3H, s), 1.34 (3H, t, J=7.1 Hz), 1.26 (3H, t, J=7.1 Hz) ppm. $^{13}C$ NMR (100.6 MHz, $CDCl_3$) δ 172.5, 170.3, 163.3, 150.6, 140.9, 102.5, 86.1, 85.0, 62.2, 62.0, 52.8, 42.0, 23.7, 14.3, 14.2 ppm; IR (neat) $v_{max}$ 2988, 2807, 1755, 1703, 1679, 1467, 1274 $cm^{-1}$; MS (ESI) m/z (MH+) 341 (100), 288 (42), 229 (50), 201 (28), 155 (13); HRMS calculated for $C_{15}H_{21}O_7N_2$ (MH) 341.1349, found 341.1345.

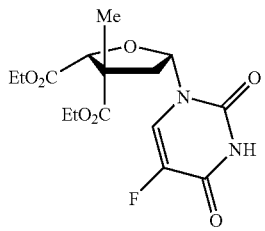

LCB-1024

LCB-1024: $C_{15}H_{19}FN_2O_7$

(2R,5S)-diethyl 5-(5-fluoro-2,4-dioxo-3,4-dihydropyrimidin-1(2H)-yl)-3-methyltetrahydrofuran-2,3-dicarboxylate The compound was purified on silica gel using 100% Hexanes to 50% AcOEt-Hexanes (70%); $[\alpha]^{25}_D = +69°$ (c 1.09, $CH_2Cl_2$). $^1H$ NMR (500 MHz, $CDCl_3$) δ 8.38 (1H, d, J=6.7 Hz), 8.18 (1H, bd), 6.28 (1H, t, J=6.5 Hz), 4.35-4.20 (2H, m), 4.38 (1H, s), 4.15 (2H, q, J=7.0 Hz), 2.80 (dd, 1H, J=6.7, 13.9 Hz), 2.40 (1H, dd, J=6.3, 13.9 Hz), 1.61 (3H, s), 1.35 (3H, t, J=7.1 Hz), 1.23 (3H, t, J=7.1 Hz) ppm. $^{13}C$ NMR (100.6 MHz, $CDCl_3$) δ 172.4, 170.2, 156.9 ($J_{C-F}$=7.0 Hz), 149.2, 140.8 ($J_{C-F}$=237.2 Hz) 125.40 ($J_{C-F}$=37.0 Hz), 86.4, 85.2, 62.3, 62.2, 52.9, 41.8, 23.7, 14.3, 14.2 ppm; IR (neat) $v_{max}$ 3198, 3072, 2986, 1722, 1375, 1269 $cm^{-1}$; MS (ESI) (MH+) 359 (25), m/z 288 (100), 229 (26), 201 (16), 155 (10); HRMS calculated for $C_{15}H_{20}O_7N_2F$ (MH) 359.1225, found 341.1254.

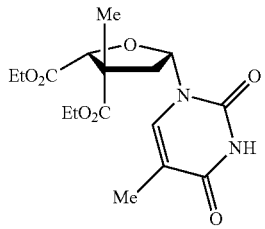

LCB-1019

LCB-1019: $C_{16}H_{22}N_2O_7$

(2R,5S)-diethyl 3-methyl-5-(5-methyl-2,4-dioxo-3,4-dihydropyrimidin-1(2H)-yl)tetrahydrofuran-2,3-dicarboxylate The compound was purified on silica gel using 100% Hexanes to 50% AcOEt-Hexanes (73%); $[\alpha]^{25}_D = +50.2°$ (c 1.05, $CH_2Cl_2$). $^1H$ NMR (500 MHz, $CDCl_3$) δ 8.80 (1H, bd), 7.94 (1H, s), 6.34 (1H, t, J=7.1 Hz), 4.28-4.18 (2H, m), 4.13 (2H, q, J=7.2 Hz), 2.78 (dd, 1H, J=7.3, 13.7 Hz), 2.34 (1H, dd, J=6.3, 13.7 Hz), 1.59 (3H, s), 1.34 (3H, t, J=7.21 Hz), 1.27 (3H, t, J=7.1 Hz) ppm. $^{13}C$ NMR (100.6 MHz, $CDCl_3$) δ 172.6, 170.4, 163.8, 150.7, 136.5, 111.2, 85.6, 84.8, 62.1, 62.0, 52.9, 41.5, 23.8, 14.3, 14.2, 12.9 ppm; IR (neat) $v_{max}$ 3148, 284, 1695, 1467, 1277 $cm^{-1}$; HRMS calculated for $C_{16}H_{23}O_7N_2$ (MH) 355, 1505, found 355.1510.

Compounds LCB-1009 and LCB-1010 ($C_{13}H_{18}N_2O_6$ mixture of anomer alpha and beta) were prepared according to Scheme 6.

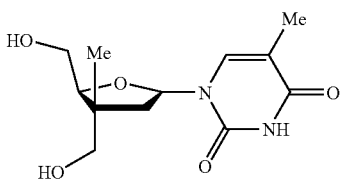

β/α

(±) methyl 2-(hydroxymethyl)-3-methyl-5-(5-methyl-2,4-dioxo-3,4-dihydropyrimidin-1(2H)-yl)tetrahydrofuran-3-carboxylate The alpha anomer: $^1H$ NMR (500 MHz, $CD_3OD$) δ 7.54 (1H, s), 6.13 (1H, t, J=6.4), 4.34 (1H, t, J=3,9), 3.80-2.77 (1H, m), 3.72 (3H, s), 3.71 (dd, 1H, J=3.5, 11.8 Hz), 2.67 (1H, dd, J=6.1, 13.5 Hz), 2.48 (1H, dd, J=6.8, 13.5 Hz), 1.92 (3H, s), 1.38 (3H, s) ppm.

The beta anomer: $^1H$ NMR (500 MHz, $CD_3OD$) δ 8.00 (1H, s), 6.09 (1H, dd, J=6.1, 8.3 Hz), 3.87 (1H, dd, J=3, 5, 11.9 Hz), 3.78 (1H, dd, J=4.6, 11.9 Hz), 3.77 (3H, s), 2.81 (dd, 1H, J=6.1, 13.0 Hz), 2.05 (1H, dd, J=8.3, 13.0 Hz), 1.91 (3H, s), 1.43 (3H, s) ppm. MS (ESI) m/z; HRMS calculated for $C_{13}H_{18}O_6N_2Na$ (M+Na) 321.1063, found 321.1058

Compounds LCB-1032 was prepared according to Scheme 6.

LCB-1032

LCB-1032, $C_{12}H_{18}N_2O_6$

(±) 1-(-4,5-bis(hydroxymethyl)-4-methyltetrahydrofuran-2-yl)-5-methylpyrimidine-2,4(1H,3H)-dione $^1H$ NMR (500 MHz, $CD_3OD$) δ 8.00 (1H, s), 6.08 (1H, dd, J=6.6, 7.8 Hz), 3.92 (1H, dd, J=3.8, 5.3 Hz), 3.82 (1H, dd, J=3.8, 11.8 Hz), 3.73 (1H, dd, J=5.3, 11.8 Hz), 3.47 (3H, s), 2.37 (1H, dd, J=6.4, 13.2 Hz), 1.92 (3H, s), 1.86 (1H, dd, J=8.0, 13.2 Hz), 1.16 (3H, s) ppm; HRMS calculated for $C_{12}H_{18}O_5N_2Na$ (M+Na) 293.1113, found 293.1179.

EXAMPLE 2

Preparation of LCB-1015, LCB-1020, LCB-1021, LCB-1022, LCB-1023, LCB-1026, and LCB-1027

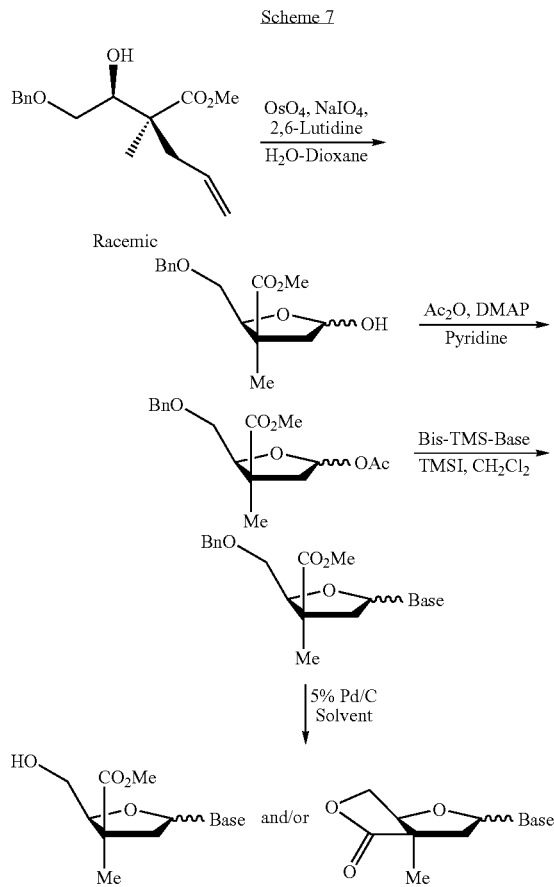

5-Acetoxy-2-benzyloxymethyl-3-methyl-tetrahydro-furan-3-carboxylic acid methyl ester To a solution of 2-Benzyloxymethyl-5-hydroxy-3-methyl-tetrahydro-furan-3-carboxylic acid methyl ester (0.48 g, 1.7 mmol) prepared as previously described, in pyridine (5 mL), Acetic Anhydride (0.32 mL, 3.4 mmol) and DMAP (5 mg) were added and the reaction was stirred at room temperature. After 3 h stirring, the reaction mixture was diluted with ethyl acetate, washed with 0.5N HCl and brine, dried over $MgSO_4$, filtered and concentrated under reduced pressure. The crude residue obtained was purified by column chromatography (EA/Hexanes, 40:60). The product was isolated as a 2.8/1 anomeric mixture.

Major compound: RMN $^1$H (500 MHz, $CDCl_3$) δppm: 7.38-7.27 (m, 5H), 6.43 (m, 1H), 4.51 (dd, 2H), 4.18 (t, 1H), 3.70-3.55 (m, 2H), 3.64 (s, 3H), 2.98 (dd, 1H), 2.08 (s, 3H), 1.88 (d, 1H) 1.50 (s, 3H).

Minor compound: RMN $^1$H (500 MHz, $CDCl_3$) δppm: 7.38-7.27 (m, 5H), 6.32 (m, 1H), 4.51 (dd, 2H), 4.10 (t, 1H), 3.70-3.55 (m, 2H), 3.61 (s, 3H), 2.82 (dd, 1H), 2.18 (dd, 1H) 2.04 (s, 3H), 1.44 (s, 3H).

2-Benzyloxymethyl-5-(5-fluoro-2,4-dioxo-3,4-dihydro-2H-pyrimidin-1-yl)-3-methyl-tetrahydro-furan-3-carboxylic acid methyl ester Bis-TMS-5-fluorouracil: To a suspension of 5-fluorouracil (130 mg, 1.0 mmol) in dichloromethane (5 mL), N,O-Bis-TMS-Acetamide (0.86 mL, 3.5 mmol) and TMS-Cl (0.1 mL) were added. After 2 h stirring at room temperature (clear solution) the reaction mixture was concentrated under reduced pressure to afford bis-TMS-5-fluorouracil.

To a solution of 5-Acetoxy-2-benzyloxymethyl-3-methyl-tetrahydro-furan-3-carboxylic acid methyl ester (213 mg, 0.66 mmol) in dichloromethane (2.5 mL), crude bis-TMS-5-fluorouracil (1.0 mmol), dissolved in dichloromethane (2.5 mL) and added and TMS-I (0.7 mL, 1.0M in $CH_2Cl_2$) were added. After 1 h stirring at room temperature, the reaction mixture was concentrated under reduced pressure and the crude residue obtained was purified by column chromatography (Acetone/$CH_2Cl_2$, 0:100 to 10:90). Only one anomer (configuration not determined) was isolated.

RMN $^1$H (500 MHz, $CDCl_3$) δppm: 8.63 (bs, 1H), 7.97 (d, 1H), 7.25-7.13 (m, 5H), 6.13 (td, 1H), 4.35 (s, 2H), 3.90 (t, 1H), 3.62 (d, 2H), 3.50 (s, 3H), 2.43 (dd, 1H), 2.12 (dd, 1H), 1.35 (s, 3H).

5-(5-Fluoro-2,4-dioxo-3,4-dihydro-2H-pyrimidin-1-yl)-2-hydroxymethyl-3-methyl-tetrahydro-furan-3-carboxylic acid methyl ester

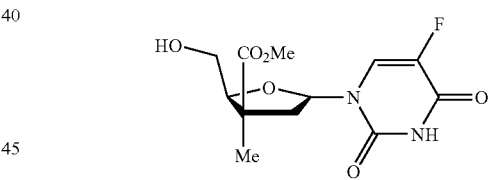

LCB-1015-1, $C_{12}H_{15}FN_2O_6$

A solution of 2-Benzyloxymethyl-5-(5-fluoro-2,4-dioxo-3,4-dihydro-2H-pyrimidin-1-yl)-3-methyl-tetrahydro-furan-3-carboxylic acid methyl ester (70 mg, 0.18 mmol) in Ethyl Acetate (4 mL) was purged 3 times with nitrogen before Pd/$C_5$% was added (50 mg). The suspension obtained was then purged 3 times with Hydrogen and stirred overnight at room temperature. The reaction mixture was then filtered over celite (rinsed with EA) and concentrated under reduced pressure. The crude residue obtained was purified by column chromatography (Acetone/$CH_2Cl_2$, 20:80). One anomer (configuration not determined) was isolated.

RMN $^1$H (500 MHz, $CD_3OD$) δppm: 8.28 (d, 1H), 6.12 (t, 1H), 3.85 (m, 1H), 3.71 (qd, 2H), 3.64 (s, 3H), 2.58 (dd, 1H), 2.24 (dd, 1H), 1.38 (s, 3H).

HRMS: Calculated 302.09; $C_{12}H_{15}FN_2O_6$, Found FTMS +pESI (MH)+ 303.09818; $C_{12}H_{16}FN_2O_6$-1.70258 ppm.

6-Methyl-1-(3a-methyl-4-oxo-hexahydro-furo[3,4-b]furan-2-yl)-1H-pyrimidine-2,4-dione

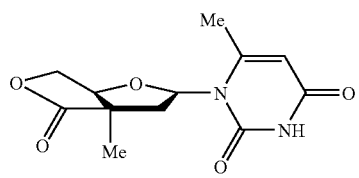

LCB-1020-1, $C_{12}H_{14}N_2O_5$

A solution of 2-Benzyloxymethyl-3-methyl-5-(6-methyl-2,4-dioxo-3,4-dihydro-2H-pyrimidin-1-yl)-tetrahydro-furan-3-carboxylic acid methyl ester (89 mg, 0.23 mmol) in methanol (2 mL) was purged 3 times with nitrogen before Pd/C 5% was added (40 mg). The suspension obtained was then purged 3 times with Hydrogen and stirred overnight at room temperature. The reaction mixture was then filtered over celite (rinsed with methanol) and concentrated under reduced pressure. The crude residue obtained was purified by column chromatography (Acetone/CH$_2$Cl$_2$, 20:80). The residue obtained was sonicated in a mixture of ethyl acetate and hexanes (1:9) and the solid obtained was collected by filtration. One anomer (configuration not determined) was isolated.

RMN $^1$H (500 MHz, CDCl$_3$) δppm: 9.84 (bs, 1H), 6.71 (t, 1H), 5.55 (d, 1H), 4.92 (d, 1H), 4.38 (dd, 1H), 4.32 (dd, 1H), 2.88 (dd, 1H), 2.62 (dd, 1H), 2.17 (s, 3H), 1.54 (s, 3H).

HRMS: Calculated 266.09; C12H14N2O5, Found FTMS +pESI (M+H)+ 267.09769; $C_{12}H_{15}N_2O_5$+0.51815 ppm.

1-(4,5-Bis-hydroxymethyl-4-methyl-tetrahydro-furan-2-yl)-6-methyl-1H-pyrimidine-2,4-dione

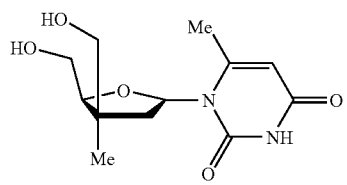

LCB-1021-1, $C_{12}H_{18}N_2O_5$

To a solution of 6-Methyl-1-(3a-methyl-4-oxo-hexahydro-furo[3,4-b]furan-2-yl)-1H-pyrimidine-2,4-dione (10 mg, 0.038 mmol) in THF (1 mL), cooled at 0° C., a solution of lithium aluminium hydride (0.075 mL, 1.0M in THF) was added. After 30 minutes stirring, the reaction was quenched by the addition of a saturated aqueous solution of Na$_2$S$_2$O$_4$ (0.15 mL) and the resulting mixture was stirred 1 h at room temp. MgSO$_4$ was then added and the reaction was filtered and concentrated. The crude residue obtained was purified by column chromatography (Acetone/CH$_2$Cl$_2$, 60:40).

RMN $^1$H (500 MHz, CD$_3$OD) δppm: 6.61 (t, 1H), 5.40 (s, 1H), 4.38 (m, 1H), 3.68 (dd, 1H), 3.60 (dd, 1H) 3.41 (dd, 2H), 2.52 (dd, 1H), 2.14 (dd, 1H), 2.04 (s, 3H), 1.12 (s, 3H).

HRMS: Calculated 270.12; $C_{12}H_{18}N_2O_5$, Found TOF MS/MS ES+ (MH)+ 271.20; $C_{12}H_{19}N_2O_5$+0.864 ppm.

5-Acetoxy-2-benzyloxymethyl-3-methyl-tetrahydro-furan-3-carboxylic acid methyl ester

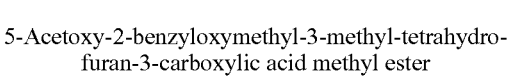

The title compound was prepared as described above according to Scheme 7. Major compound: RMN $^1$H (500 MHz, CDCl$_3$) δppm: 7.37-7.27 (m, 5H), 6.30 (dd, 1H), 4.74 (t, 1H), 4.53 (dd, 2H), 3.71 (s, 3H), 3.67-3.58 (m, 2H), 2.58 (dd, 1H), 2.24 (dd, 1H), 2.04 (s, 3H), 1.25 (s, 3H). Minor compound: RMN $^1$H (500 MHz, CDCl$_3$) δppm: 7.38-7.27 (m, 5H), 6.28 (m, 1H), 4.61-4.50 (m, 3H), 3.70 (s, 3H), 3.69-3.55 (m, 2H), 2.82 (dd, 1H), 2.05 (dd, 1H), 2.04 (s, 3H), 1.37 (s, 3H).

2-Benzyloxymethyl-5-(5-fluoro-2,4-dioxo-3,4-dihydro-2H-pyrimidin-1-yl)-3-methyl-tetrahydro-furan-3-carboxylic acid methyl ester

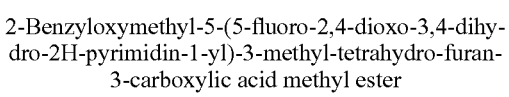

The title compound was prepared as described above according to Scheme 7 using bis-TMS-thymine. The product was isolated as a 1:1 anomeric mixture. RMN $^1$H (Mixture) (500 MHz, CDCl$_3$) δppm: 9.20 (bs, 1H), 8.98 (bs, 1H), 8.17 (d, 1H), 7.58 (d, 1H), 7.40-7.30 (m, 10H), 6.15 (td, 1H), 6.10 (td, 1H), 4.75 (t, 1H), 4.60-4.55 (m, 4H), 4.53 (t, 1H), 3.84 (dd, 1H), 3.78 (s, 3H), 3.70 (s, 3H), 3.70-3.60 (m, 3H), 2.84 (dd, 1H), 2.58 (dd, 2H), 1.85 (dd, 1H), 1.43 (s, 3H), 1.37 (s, 3H).

The compounds described below were prepared as described above according to Scheme 7. The 2 anomers obtained were separated by column chromatography (Acetone/CH$_2$Cl$_2$, 40:60). The configuration of these anomers was not determined.

5-(5-Fluoro-2,4-dioxo-3,4-dihydro-2H-pyrimidin-1-yl)-2-hydroxymethyl-3-methyl-tetrahydro-furan-3-carboxylic acid methyl ester

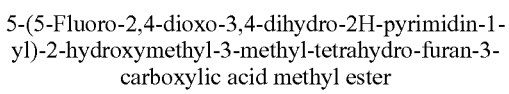

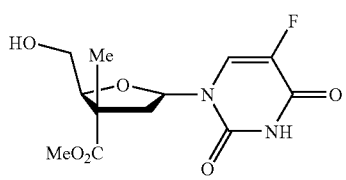

LCB-1022-1, $C_{12}H_{15}FN_2O_6$ (fast eluting anomer)

RMN $^1$H (500 MHz, CD$_3$OD) δppm: 7.88 (d, 1H), 6.08 (t, 1H), 4.64 (m, 1H), 3.78 (dd, 1H), 3.72 (s, 3H) 3.70 (dd, 1H), 2.67 (dd, 1H), 2.50 (dd, 1H), 1.37 (s, 3H).

HRMS: Calculated 302.09; $C_{12}H_{15}FN_2O_6$, Found FTMS +pESI (M+H)⁻ 303.09882; $C_{12}H_{16}FN_2O_6$+0.41115 ppm.

5-(5-Fluoro-2,4-dioxo-3,4-dihydro-2H-pyrimidin-1-yl)-2-hydroxymethyl-3-methyl-tetrahydro-furan-3-carhoxylic acid methyl ester

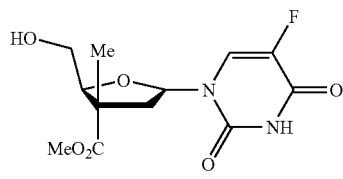

LCB-1023-1, $C_{12}H_{15}FN_2O_6$ (slow eluting anomer)

RMN ¹H (500 MHz, CD₃OD) δppm: 7.59 (d, 1H), 6.16 (t, 1H), 4.62 (m, 1H), 3.85 (dd, 1H), 3.80 (dd, 1H) 3.76 (s, 3H), 2.63 (dd, 1H), 2.58 (dd, 1H), 1.39 (s, 3H).

HRMS: Calculated 302.09; $C_{12}H_{15}FN_2O_6$, Found FTMS +pESI (M+H)⁺ 303.09866; $C_{12}H_{16}FN_2O_6$-0.09227 ppm.

The compounds described below were prepared as described above according to Scheme 7 using the corresponding methyl ester.

1-(4,5-Bis-hydroxymethyl-4-methyl-tetrahydro-furan-2-yl)-5-fluoro-1H-pyrimidine-2,4-dione

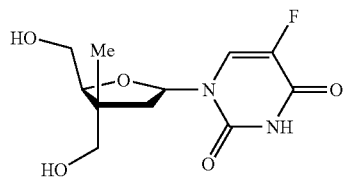

LCB-1026-1, $C_{11}H_{15}FN_2O_5$

RMN ¹H (500 MHz, CD₃OD) δppm: 8.44 (d, 1H), 6.08 (t, 1H), 3.92 (m, 1H), 3.83 (dd, 1H), 3.74 (dd, 1H) 3.43 (s, 2H), 2.39 (dd, 1H), 1.84 (dd, 1H), 1.16 (s, 3H).

1-(4,5-Bis-hydroxymethyl-4-methyl-tetrahydro-furan-2-yl)-5-fluoro-1H-pyrimidine-2,4

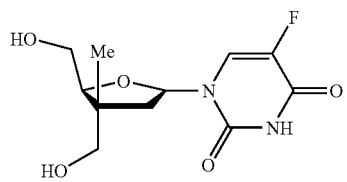

LCB-1027-1,

RMN ¹H (500 MHz, CD₃OD) δppm: 7.97 (d, 1H), 6.11 (t, 1H), 4.22 (m, 1H), 3.68 (m, 2H), 3.52 (s, 2H) 2.23 (dd, 1H), 2.15 (dd, 1H), 1.06 (s, 3H).

EXAMPLE 3

Preparation of LCB-1016, LCB-1017, LCB-1028, and LCB-1029

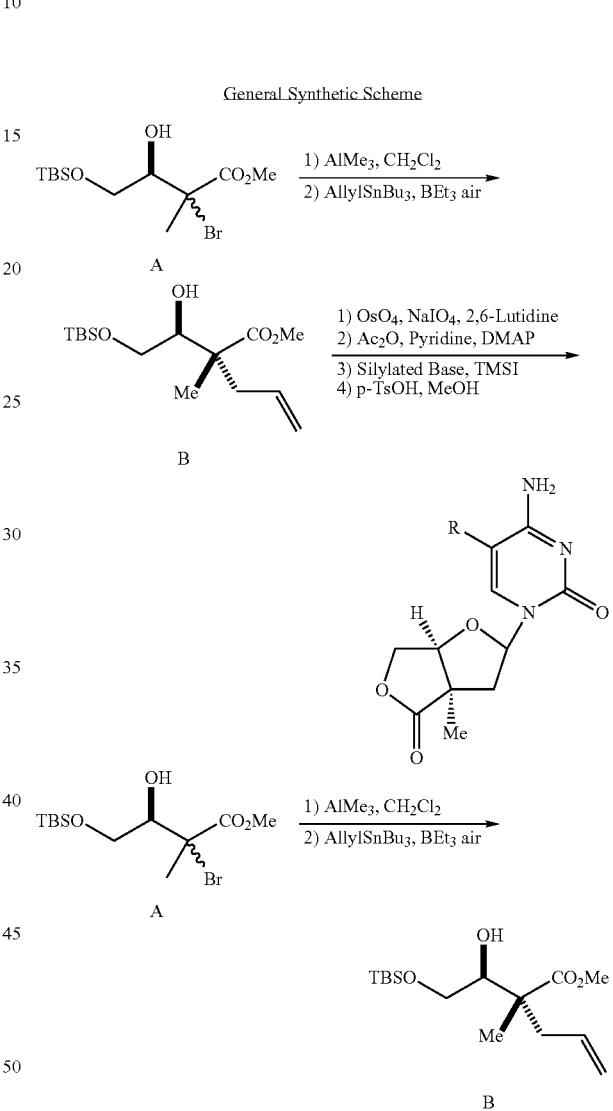

To a solution of compound A (8.6 g; 25 mmol) in CH₂Cl₂ (125 mL) at 0° C. was added AlMe₃ (2M in hexanes; 15 mL; 1.2 equiv.). The reaction was stirred at this temperature for 30 min before addition of allyltributyltin (15.5 mL; 2 equiv.), BEt₃ (1M in CH₂Cl₂; 5 mL; 0.2 equiv.) and air (syringe). Every hour, 0.2 equiv. of BEt₃ is added to the medium followed by air. After 5 h at 0° C., the reaction is quenched by addition of MeOH (10 mL) and a saturated aqueous solution of NH₄Cl. The reaction is stirred at room temperature for 2 h before being extracted with CH₂Cl₂ (×3). The combined organic phases were dried over MgSO₄. The solvent was removed and the crude purified by flash chromatography using Hex/AcOEt (9:1) to yield the desired compound B (m=5.29 g; 70%).

(±)-(R)-methyl 2-((S)-2-(tert-butyldimethylsilyloxy)-1-hydroxyethyl)-2-methylpent-4-enoate ¹H-NMR (500 MHz, CD3OD) ppm 5.72 (m, 1H), 5.10 (m, 2H), 3.75 (dd, 1H, J=3.0 Hz, J=9.7 Hz), 3.71 (dd, 1H, J=4.4 Hz, J=10.4 Hz), 3.71 (s, 3H), 3.66 (dd, 1H, J=5.8 Hz, J=9.7 Hz), 3.19 (d, 1H, J=5.9 Hz), 2.57 (dd, 1H, J=7.1 Hz, J=13.5 Hz), 2.24 (dd, 1H, J=7.7 Hz, J=13.5 Hz), 1.17 (s, 3H), 0.91 (s, 9H), 0.08 (s, 6H).

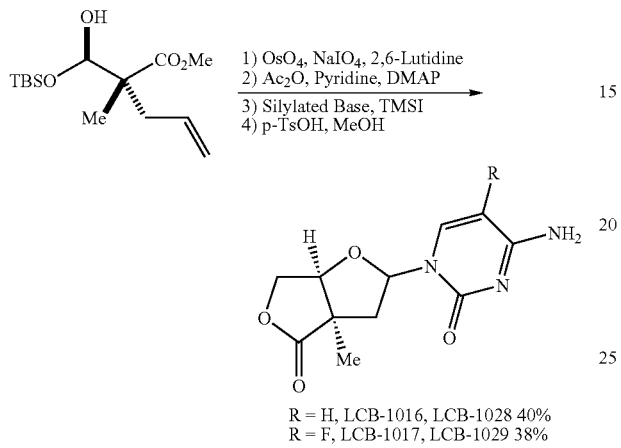

R = H, LCB-1016, LCB-1028 40%
R = F, LCB-1017, LCB-1029 38%

To a solution of compound B (800 mg; 2.6 mmol) in dioxane-water (3:1; 25 mL) at room temperature were added 2,6-Lutidine (603 μL; 2 equiv.), OsO₄ (4% wt in water; 2% mol; 651 μL) and NaIO₄ (2.22 g; 4 equiv.). The reaction was stirred at 25° C. and monitored by TLC. After 3 h, water was added to the medium and the reaction was extracted with CH₂Cl₂ (×4). The combined organic phases were dried over MgSO₄. The solvent was removed and the crude used for the next step. The lactol was dissolved in Pyridine (1 mL) and chilled at 0° C. DMAP (50 mg) and Ac₂O (245 μL; 2 equiv.) were added. The reaction was stirred overnight at room temperature. Volatiles were removed by coevaporation with toluene (×2). The crude acetate was used without further purification.

To a solution of the appropriate silylated base (1 mmol in 5 mL; 1 equiv.) was added a solution of the acetate (1 mmol in 5 mL; 1 equiv.) followed by TMSI (3M in CH₂Cl₂; 1.1 equiv.). The reaction was stirred for 2 h at room temperature before addition of MeOH (5 mL) and p-TsOH (1 equiv.). The reaction was stirred overnight. An Amberlite® IRA-400 resin (OH form, 5 g) was added and stirred for 4 h. After filtration and evaporation of volatiles, the compound was recrystallyzed from CH₂Cl₂/iPr₂O to give a mixture (1:1 ☐☐) of anomers of the corresponding nucleosides.

(±)-4-Amino-1-((3R,6S)-3-methyl-4-oxo-hexahydro-furo[3,4-b]furan-2-yl)-1H-pyrimidin-2-one

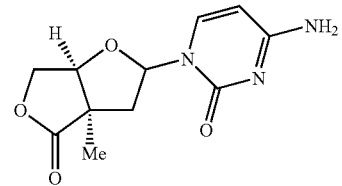 [SMILES: C[C@@]12CC(n3ccc(N)nc3=O)O[C@@H]1COC2=O]

¹H-NMR (500 MHz, CD3OD) ppm 7.66 (d, 1H, J=7.4 Hz), 7.51 (d, 1H, J=7.5 Hz), 6.06 (m, 2H), 5.88 (m, 2H), 5.88 (m, 1H), 4.89 (m, 1H), 4.64 (m, 2H), 4.55 (dd, 1H, J=3.3 Hz, J=11.3 Hz), 4.48 (dd, 1H, J=3.3 Hz, J=11.1 Hz), 4.40 (d, 1H, J=11.1 Hz), 2.94 (dd, 1H, J=7.0 Hz, J=13.7 Hz), 2.64 (dd, 1H, J=7.2 Hz, J=14.3 Hz), 2.56 (dd, 1H, J=3.6 Hz, J=14.3 Hz), 2.37 (dd, 1H, J=6.7 Hz, J=13.7 Hz), 1.47 (s, 3H), 1.42 (s, 3H); MS (ESI) m/z 503.1 (2 MH⁺), 274.0 (M+Na), 252.1 (MH⁺); HRMS (ESI) calculated for C₁₁H₁₄N₃O₄ (MH) 252.0984, found 252.0984.

(±)-4-Amino-5-fluoro-1-((3R,6S)-3-methyl-4-oxo-hexahydro-furo[3,4-b]furan-2-yl)-1H-pyrimidin-2-one

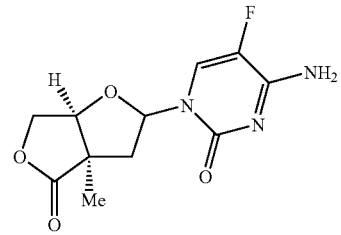 [SMILES: C[C@@]12CC(n3cc(F)c(N)nc3=O)O[C@@H]1COC2=O]

¹H-NMR (500 MHz, CD3OD) 7.87 (d, 1H, J=6.5 Hz), 7.58 (d, 1H, J=6.6 Hz), 6.00 (m, 1H), 5.87 (t, 1H, J=6.8 Hz), 4.90 (d, 1H, J=3.2 Hz), 4.69 (d, 1H, J=11.4 Hz), 4.66 (d, 1H, J=3.3 Hz), 4.56 (dd, 1H, J=3.3 Hz, J=11.4 Hz), 4.48 (dd, 1H, J=3.3 Hz, J=11.1 Hz), 4.41 (d, 1H, J=11.1 Hz), 2.94 (dd, 1H, J=6.8 Hz, J=13.7 Hz), 2.62 (m, 2H), 2.33 (dd, 1H, J=6.8 Hz, J=13.7 Hz), 1.46 (s, 3H), 1.41 (s, 3H); MS (ESI) m/z 539.1 (2MH⁺, 60), 270.0 (MH⁺, 100); HRMS (ESI) calculated for C₁₁H₁₃FN₃O₄ (MH) 270.0890, found 270.0892.

What is claimed is:

1. A compound of the formula

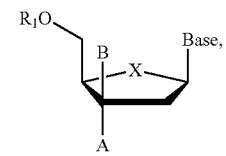

I

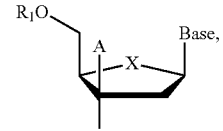

II

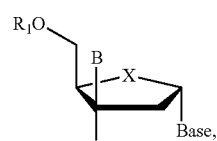

III

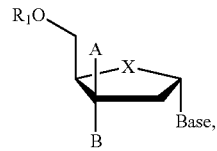

IV

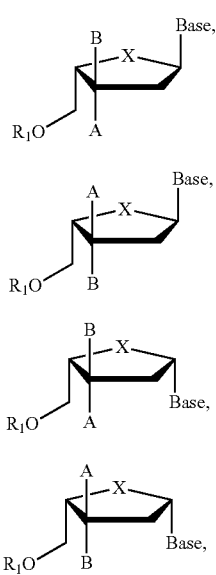

or pharmaceutically acceptable salts thereof, wherein:
X is O or S;
A is —(CH$_2$)$_n$M;
n is 1 to 3;
M is —OR$_1$, —C(O)OR$_2$, —CONR$_4$R$_{4a}$, —SOR$_5$, —SO$_2$NR$_5$R$_{5a}$, or —N$_3$;
R$_1$ is —H, —COR$_2$, —CONR$_4$R$_{4a}$, —CH$_2$—P(O)(OH)$_2$, or —P(O)(OEt)$_2$;
R$_2$ is —H, aryl, or C$_1$-C$_6$ alkyl;
R$_3$ is aryl or C$_1$-C$_3$ alkylaryl;
R$_4$ and R$_{4a}$ are independently together with the nitrogen to which they are attached form —(AA)$_x$, wherein x is 1 to 5, and AA is a natural, non-natural, D- or L- amino acid, wherein —(AA)$_x$ comprises a terminal —COOR$_3$ group wherein the carbonyl is protected or unprotected;
R$_5$ and R$_{5a}$ are independently aryl or C$_1$-C$_3$ alkylaryl; and
Base is a purine derivative or a pyrimidine derivative selected from the group consisting of

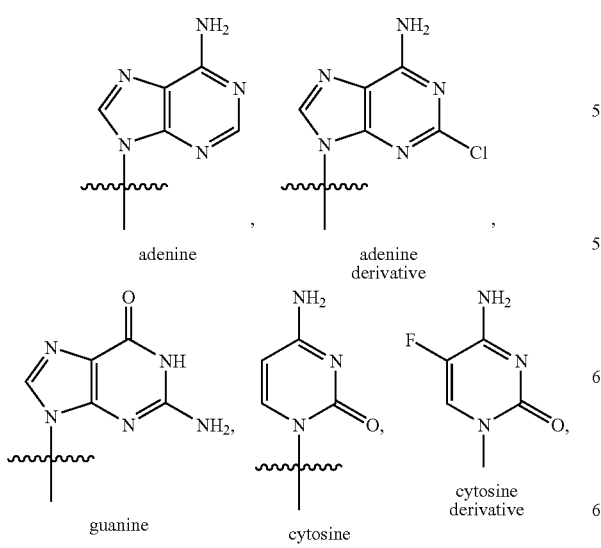

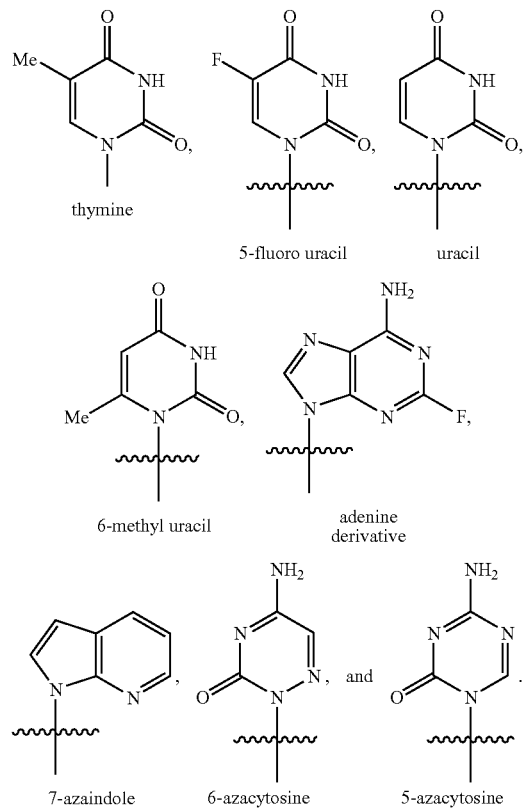

2. A compound according to claim 1, wherein:
R$_1$ is —H, —CH$_2$—P(O)(OH)$_2$, or —P(O)(OEt)$_2$; and
R$_2$ is aryl or —C$_1$-C$_3$ alkyl.

3. A compound according to claim 2, wherein:
R$_2$ is C$_1$-C$_3$ alkyl;
R$_4$ and R$_{4a}$ together with the nitrogen to which they are attached form —(AA)$_{1-4}$;
R$_5$ and R$_{5a}$ are independently phenyl or —CH$_2$-phenyl; and
Base is selected from the group consisting of

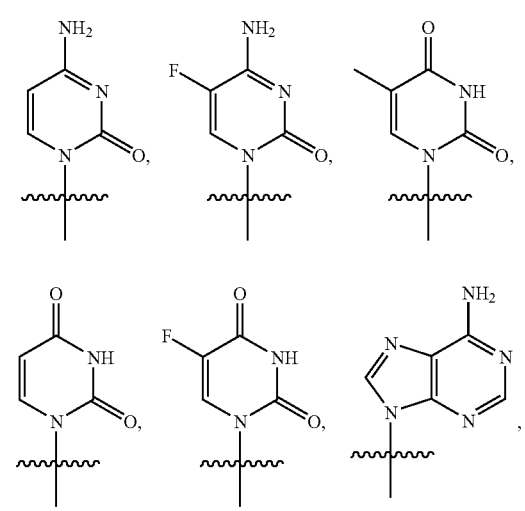

-continued

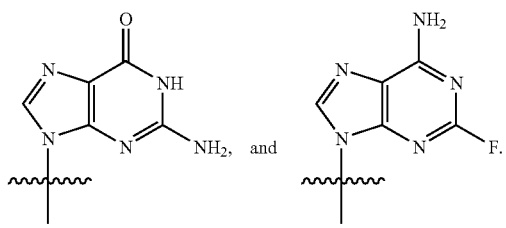

4. A compound according to claim 3, wherein $R_4$ and $R_{4a}$ together with the nitrogen to which they are attached form -Arg-Arg-Arg.

5. The compound according to claim 1, wherein;

A is —$(CH_2)_n$—C(O)—$NH_2$, —$(CH_2)_n$—C(O)$OR_2$, or —$(CH_2)_n$—$(CH_2)_n$—OH;

n is 1 to 3; and

Base is selected from the group consisting of

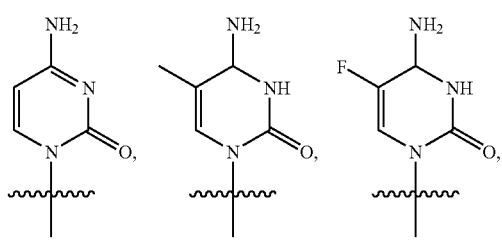

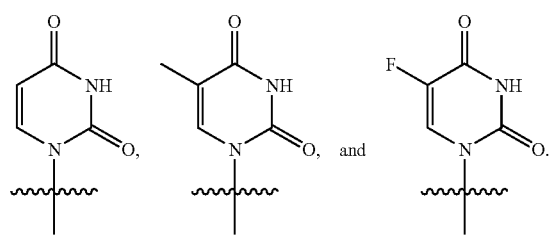

6. A compound according to claim 1, wherein:

A is —$(CH_2)_n$—C(O)—$NH_2$, —$(CH_2)_n$—C(O)$OCH_3$, or —$(CH_2)_n$—OH;

n is 1 to 3 and

Base is selected from the group consisting of

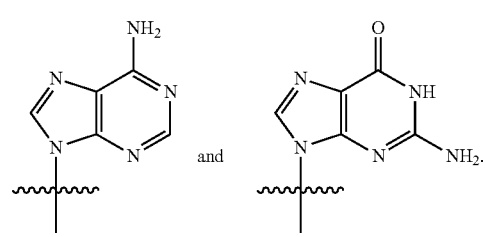 [SMILES: *n1cnc2c(N)ncnc21 ; *n1cnc2c(=O)[nH]c(N)nc21]

7. A compound of the formula

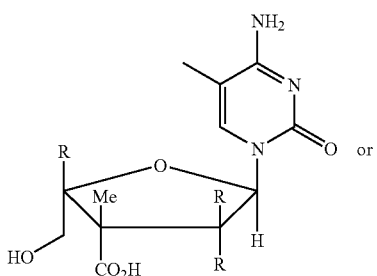
XXV

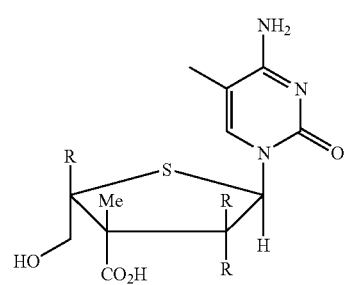
XXVI or pharmaceutically acceptable salts thereof, wherein R is —H.

8. A compound selected from the group consisting of

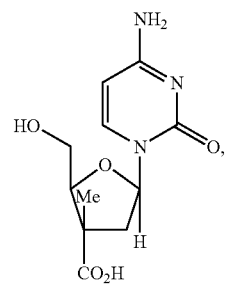
1

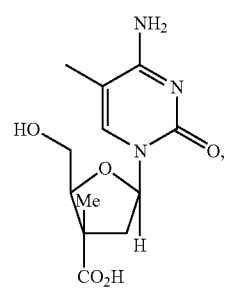
2

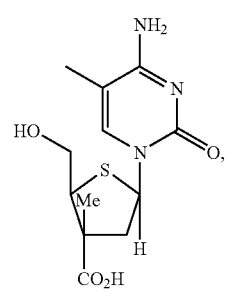
3

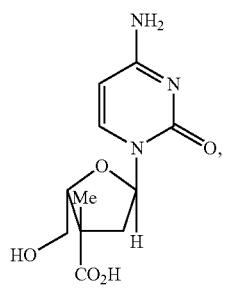
4
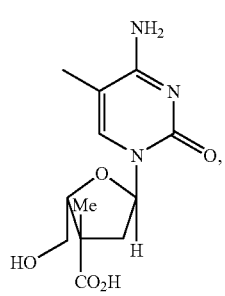
5
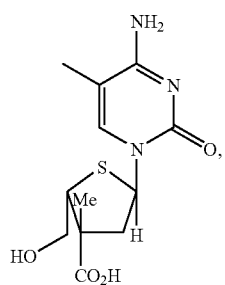
6
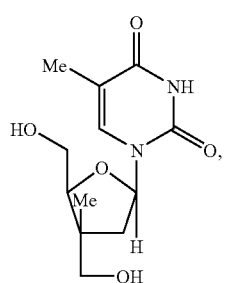
7
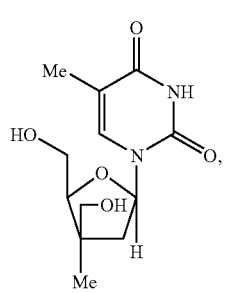
8
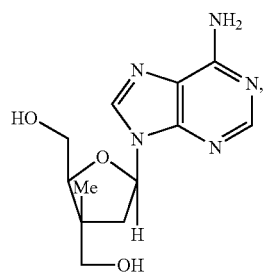
9
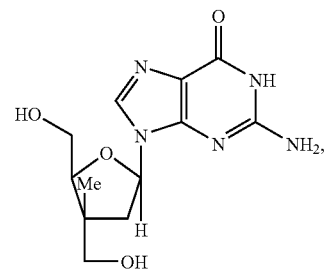
10
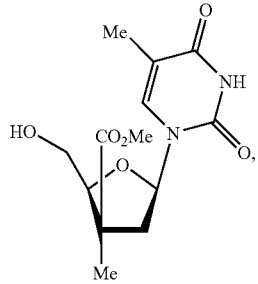
11
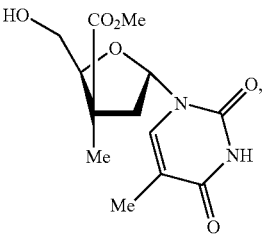
12
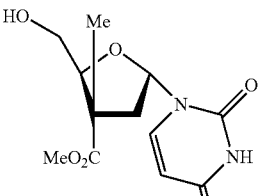
13
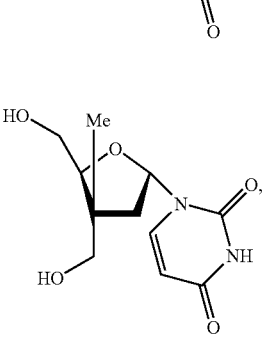
14

15
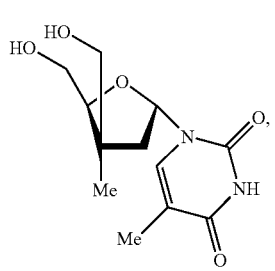
16
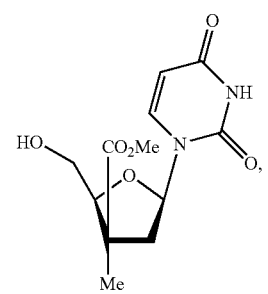
17
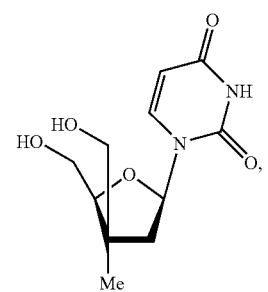
18
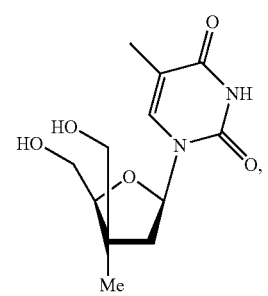
19
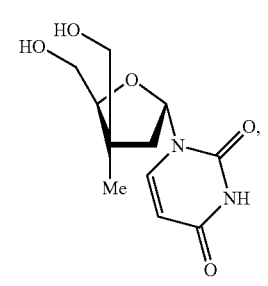
20
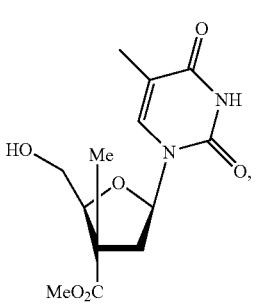
β/α 13:1
21
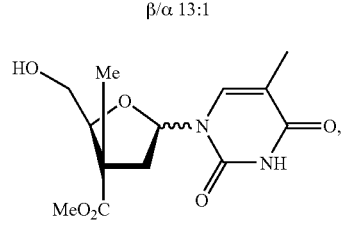
β/α 1:1
22
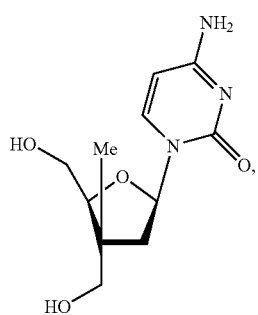
23
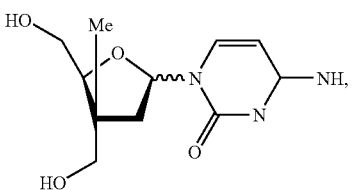
24
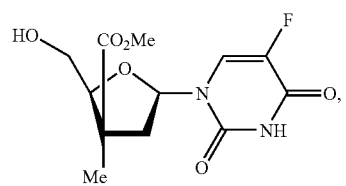
1:0
25
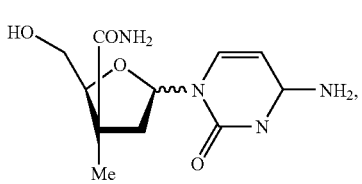

-continued

[Structures 26-38 depicting nucleoside analogs with various sugar and base modifications, including α and β anomers]

9. A pharmaceutical composition comprising a pharmaceutically acceptable carrier, excipient, or diluent and a compound according to claim 1 or a pharmaceutically acceptable salt thereof.

10. A method for inhibiting proliferation of a cell associate with a tumor relating to lung or adenocarcinoma state 2, comprising contacting the cell in which inhibition is desired with a compound selected from the group consisting of

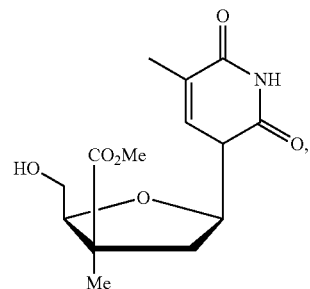

LCB-1000

(2S,3R,5R)-methyl 2-
(hydroxymethyl)-3-methyl-
5-(5-methyl-2,4-dioxo-3,4-
dihydropyrimidin-1(2H)-
yl)tetrahydrofuran-3-
carboxylate

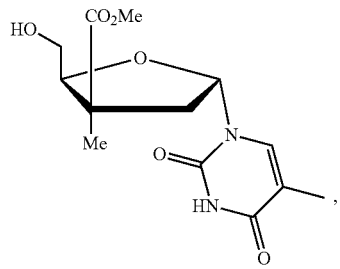

LCB-1001

(2S,3R,5S)-methyl 2-
(hydroxymethyl)-3-methyl-
5-(5-methyl-2,4-dioxo-3,4-
dihydropyrimidin-1(2H)-
yl)tetrahydrofuran-3-
carboxylate

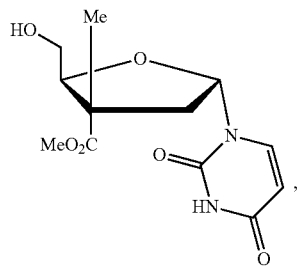

LCB-1002

(2S,3S,5S)-methyl 5-
(2,4-cioxo-3,4-
dihydropyrimidin-1(2H)-
yl)-2-(hydroxymethyl)-3-
methyltetrahydrofuran-
3-carboxylate -continued

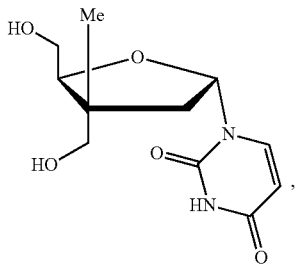

LCB-1003

1-((2S,4R,5S)-4,5-
bis(hydroxymethyl)-4-
methyltetrahydrofuran-
2-yl)pyrimidine-
2,4(1H,3H)-dione

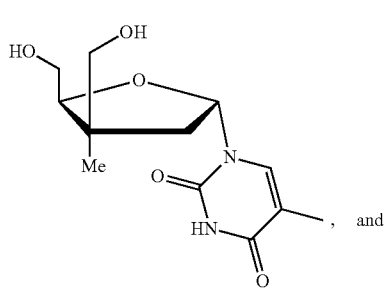

LCB-1004

1-((2S,4S,5S)-4,5-
bis(hydroxymethyl)-4-
methyltetrahydrofuran-2-yl)-
5-methylpyrimidine-
2,4(1H,3H)-dione , and

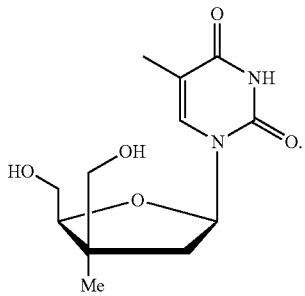

LCB-1007

1-((2R,4S,5S)-4,5-
bis(hydroxymethyl)-4-
methyltetrahydrofuran-
2-yl)-5-methylpyrimidine-
2,4(1H,3H)-dione

11. A method for inhibiting proliferation of a cell associated with a tumor relating to lung or adenocarcinoma stage 2 in a patient comprising administering to the patient a pharmaceutical composition comprising a compound selected from the group consisting of

LCB-1000

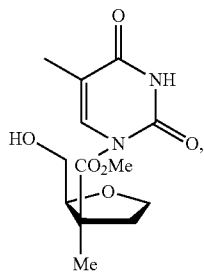

(2S, 3R, 5R)-methyl 2-
(hydroxymethyl)-3-methyl-
5-(5-methyl-2, 4-dioxo-3, 4-
dihydropryimidin-1(2H)-
yl)tetrahydrofuran-3-
carboxylate

LCB-1001

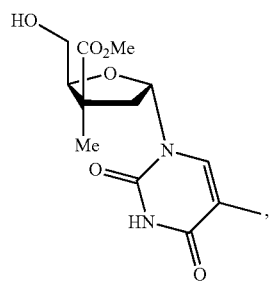

(2S, 3R, 5S)-methyl 2-
(hydroxymethyl)-3-methyl-
5-(5-methyl-2, 4-dioxo-3, 4-
dihydropryimidin-1(2H)-
yl)tetrahydrofuran-3-
carboxylate

LCB-1002

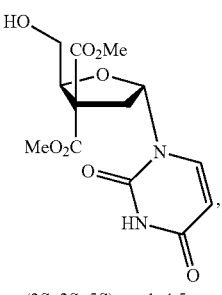

(2S, 3S, 5S)-methyl 5-
(2, 4-dioxo-3, 4-
dihydropyrimidin-1(2H)-
yl)-2-(hydroxymethyl)-3-
methyltetrahydrofuran-
3-carboxylate

LCB-1003

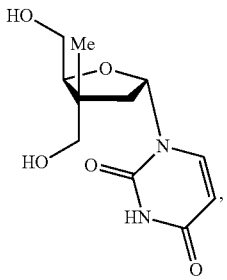

1-((2S, 4R, 5S)-4, 5-
bis(hydroxymethyl)-4-
methyltetrahydrofuran-
2-yl)pyrimidine-
2, 4(1H, 3H)-dione -continued

LCB-1004

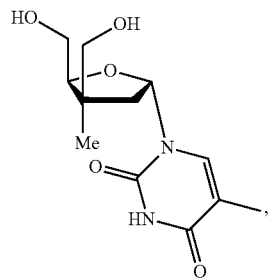

and 1-((2S, 4R, 5S)-4, 5-
bis(hydroxymethyl)-4-
methyltetrahydrofuran-2-yl)-
5-methylpyrimidine-
2, 4(1H, 3H)-dione

LCB-1007

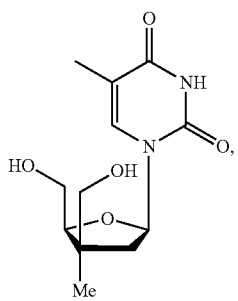

1-((2R, 4S, 5S)-4, 5-
bis(hydroxymethyl)-4-
methyltetrahydrofuran-
2-yl)-5-methylpyrimidine-
2, 4(1H, 3H)-dione and a pharmaceutically acceptable carrier, excipient or diluent.

12. A method for inhibiting proliferation of a cell associated with a tumor relating to plural effusion or mesothelioma stage 4, comprising contacting the cell in which inhibition is desired with a compound selected from the group consisting of

LCB-1000

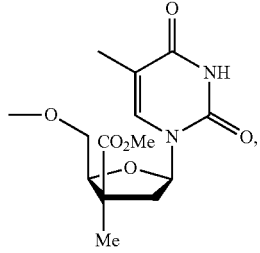

(2S, 3R, 5R)-methyl 2-
(hydroxymethyl)-3-methyl-
5-(5-methyl-2, 4-dioxo-3, 4-
dihydropryimidin-1(2H)-
yl)tetrahydrofuran-3-
carboxylate

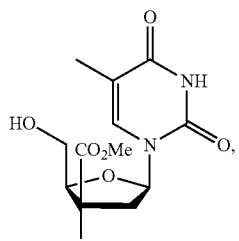

LCB-1000

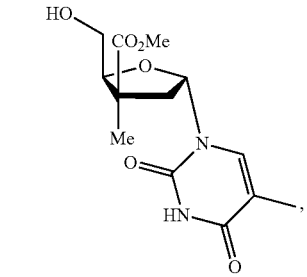

LCB-1001

(2S, 3R, 5R)-methyl 2-
(hydroxymethyl)-3-methyl-
5-(5-methyl-2, 4-dioxo-3, 4-
dihydropryimidin-1(2H)-
yl)tetrahydrofuran-3-
carboxylate

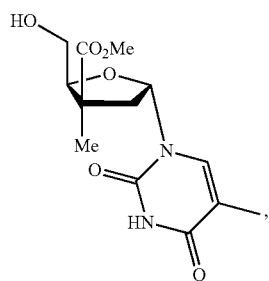

LCB-1001

(2S, 3R, 5S)-methyl 2-
(hydroxymethyl)-3-methyl-
5-(5-methyl-2, 4-dioxo-3, 4-
dihydropryimidin-1(2H)-
yl)tetrahydrofuran-3-
carboxylate

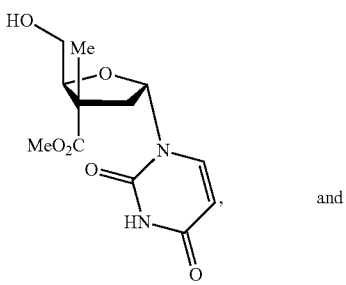

LCB-1002

(2S, 3R, 5S)-methyl 2-
(hydroxymethyl)-3-methyl-
5-(5-methyl-2, 4-dioxo-3, 4-
dihydropryimidin-1(2H)-
yl)tetrahydrofuran-3-
carboxylate and

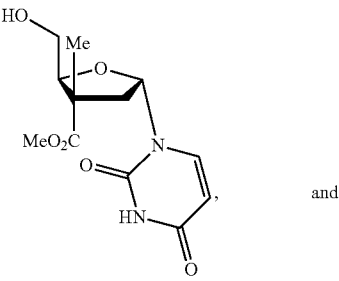

LCB-1002

(2S, 3S, 5S)-methyl 5-
(2, 4-dioxo-3, 4-
dihydropyrimidin-1(2H)-
yl)-2-(hydroxymethyl)-3-
methyltetrahydrofuran-
3-carboxylate and

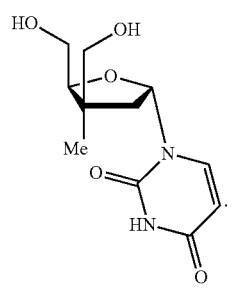

LCB-1004

1-((2S, 4S, 5S)-4, 5-
bis(hydroxymethyl)-4-
methyltetrahydrofuran-2-yl)-
5-methylpyrimidine-
2, 4(1H, 3H)- dione

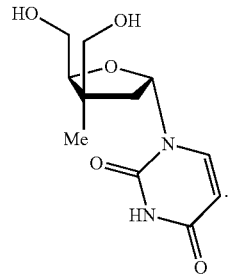

LCB-1004

1-((2S, 4S, 5S)-4, 5-
bis(hydroxymethyl)-4-
methyltetrahydrofuran-2-yl)-
5-methylpyrimidine-
2, 4(1H, 3H)- dione

13. A method for inhibiting proliferation of a cell associated with a tumor relating to plural effusion or mesothelioma stage 4, comprising contacting the cell in which inhibition is desired with pharmaceutical composition comprising a compound selected from the group consisting of and a pharmaceutically acceptable carrier, excipient or diluent.

14. A method for inhibiting proliferation of a cell associated with a tumor relating to brain cerebellum or malignant primitive neuroectodermal tumor, comprising contacting the cell in which inhibition is desired with a compound selected from the group consisting of

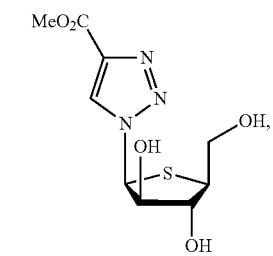

LCB-1013

L-methyl 1-
((2S, 3R, 4R, 5S)-3, 4-
dihydroxy-5-
(hydroxymethyl)tetrahydrot
hiophen-2-yl)-1H, 1, 2, 3-
triazole-4-carboxylate

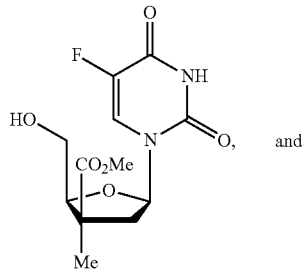

LCB-1015

(2S, 3R, 5R)-methyl 5-(5-
fluoro-2, 4- dioxo-3, 4-
dihydropyrimidin-1(2H)-
yl)-2-(hydroxymethyl)-3-
methyltetrahydrofuran-
3-carboxylate

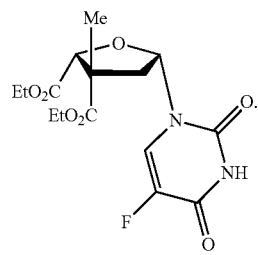

LCB-1024

(2R, 5S)-diethyl-5-(5-fluoro-
2, 4-dioxo-3, 4-
dihydropyrimidin-1(2H)-yl)-
3-methyltetrahydrofuran-2.3-
dicarboxylate 15. A method for inhibiting proliferation of a cell associated with a tumor, comprising contacting the cell in which inhibition is desired with a pharmaceutical composition comprising a compound selected from the group consisting of

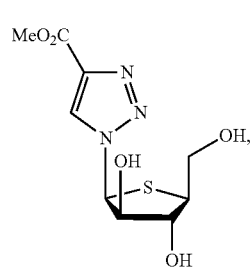

LCB-1013

L-methyl 1-
((2S, 3R, 4R, 5S)-3, 4-
dihydroxy-5-
(hydroxymethyl)tetrahydrot
hiophen-2-yl)-1H, 1, 2, 3-
triazole-4-carboxylate

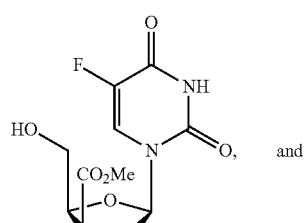

LCB-1015

(2S, 3R, 5R)-methyl 5-(5-
fluoro-2, 4- dioxo-3, 4-
dihydropyrimidin-1(2H)-
yl)-2-(hydroxymethyl)-3-
methyltetrahydrofuran-
3-carboxylate

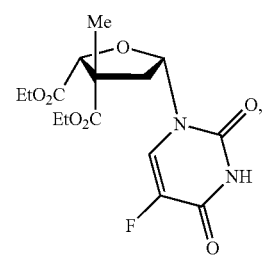

LCB-1024

(2R, 5S)-diethyl-5-(5-fluoro-
2, 4-dioxo-3, 4-
dihydropyrimidin-1(2H)-yl)-
3-methyltetrahydrofuran-2.3-
dicarboxylate and a pharmaceutically acceptable carrier, excipient or diluent.

16. A method for inhibiting proliferation of a cell associated with a tumor relating to mammary gland, breast derived from ascites or epithelial ductal carcinoma, comprising contacting the cell in which inhibition is desired with a compound selected from the group consisting of

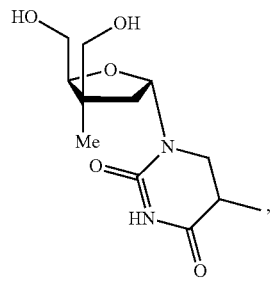

LCB-1004

1-((2S, 4S, 5S)-4, 5-
bis(hydroxymethyl)-4-
methyltetrahydrofuran-2-yl)-
5-methylpyrimidine-
2, 4(1H, 3H)-dione

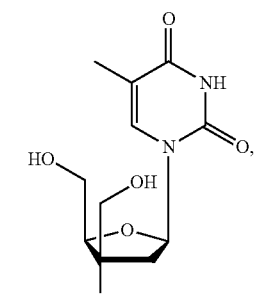

LCB-1007

1-((2R, 4S, 5S)-4, 5-
bis(hydroxymethyl)-4-
methyltetrahydrofuran-
2-yl)-5-methylpyrimidine-
2, 4(1H, 3H)-dione a mixture of LCB-1010 (β anomer) and LCB 1010 (α anomer) in the proportion β:α1/1

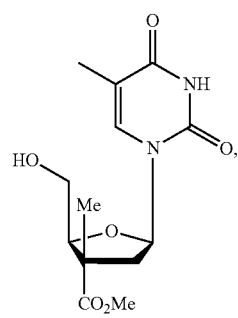

LCB-1010 (β anomer)

(2S, 3S, 5R)-methyl 2-
(hydroxymethyl)-3-methyl-
5-(5-methyl-2, 4-dioxo-3, 4-
dihydropyrimidin-1(2H)-
yl)tetrahydrofuran-3-
carboxylate

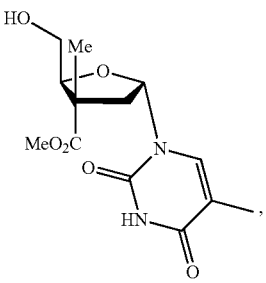

LCB-1010 (α anomer)

(2S, 3S, 5S)-methyl 2-
(hydroxymethyl)-3-methyl-
5-(5-methyl-2, 4-dioxo-3, 4-
dihydropyrimidin-1(2H)-
yl)tetrahydrofuran-3-
carboxylate

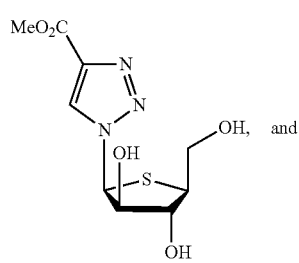

LCB-1013

L-methyl 1-
((2S, 3R, 4R, 5S)-3, 4-
dihydroxy-5-
(hydroxymethyl)tetrahydrot
hiophen-2-yl)-1H-1,2,3-
triazole-4-carboxylate

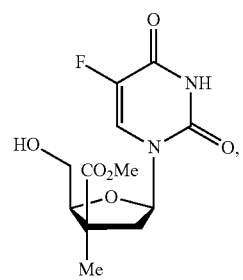

LCB-1015

(2S, 3R, 5R)-methyl 5-(5-
fluoro-2, 4-dioxo-3, 4-
dihydropyrimidin-1(2H)-
yl)-2-(hydroxymethyl)-3-
methyltetrahydrofuran-
3-carboxylate and a pharmaceutically acceptable carrier, excipient or diluent.

17. A method for inhibiting proliferation of a cell associated with a tumor relating to mammary gland, breast derived from ascites or epithelial ductal carcinoma, comprising contacting the cell in which inhibition is desired with a pharmaceutical composition comprising a compound selected from the group consisting of

LCB-1004

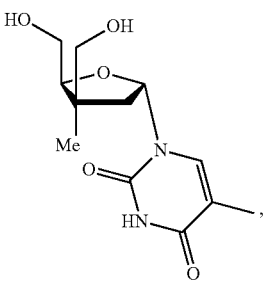

1-((2S, 4S, 5S)-4, 5-bis(hydroxymethyl)-4-methyltetrahydrofuran-2-yl)-5-methylpyrimidine-2,4(1H, 3H)-dione

LCB-1007

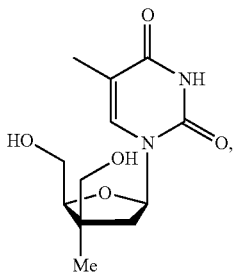

1-((2R, 4S, 5S)-4, 5-bis(hydroxymethyl)-4-methyltetrahydrofuran-2-yl)-5-methylpyrimidine-2, 4(1H, 3H)-dione a mixture of LCB-1010 (β anomer) and LCB 1010 (α anomer) in the proportion β:α 1/1

LCB-1010 (β anomer)

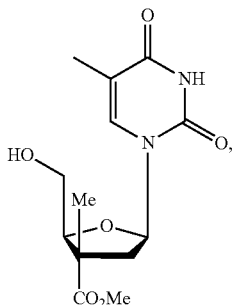

(2S, 3S, 5R)-methyl 2-(hydroxymethyl)-3-methyl-5-(5-methyl-2, 4-dioxo-3, 4-dihydropyrimidin-1(2H)-yl)tetrahydrofuran-3-carboxylate LCB-1010 (α anomer)

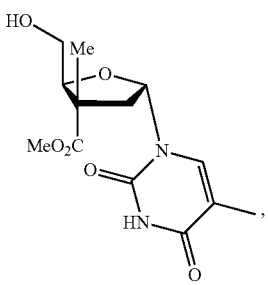

(2S, 3S, 5S)-methyl 2-(hydroxymethyl)-3-methyl-5-(5-methyl-2,4-dioxo-3,4-dihydropyrimidin-1(2H)-yl)tetrahydrofuran-3-carboxylate

LCB-1013

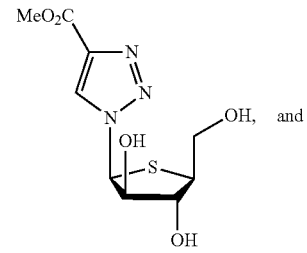

L-methyl 1-((2S, 3R, 4R, 5S)-3, 4-dihydroxy-5-(hydroxymethyl)tetrahydrothiophen-2-yl)-1H-1,2,3-triazole-4-carboxylate and

LCB-1015

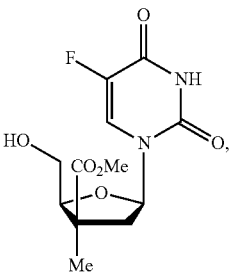

(2S, 3R, 5R)-methyl 5-(5-fluoro-2, 4-dioxo-3, 4-dihydropyrimidin-1(2H)-yl)-2-(hydroxymethyl)-3-methyltetrahydrofuran-3-carboxylate and a pharmaceutically acceptable carrier, excipient or diluent.

* * * * *